US 12,243,637 B2

(12) United States Patent
Brynolfsson et al.

(10) Patent No.: US 12,243,637 B2
(45) Date of Patent: *Mar. 4, 2025

(54) SYSTEMS AND METHODS FOR ARTIFICIAL INTELLIGENCE-BASED IMAGE ANALYSIS FOR DETECTION AND CHARACTERIZATION OF LESIONS

(71) Applicant: EXINI Diagnostics AB, Lund (SE)

(72) Inventors: Johan Martin Brynolfsson, Helsingborg (SE); Kerstin Elsa Maria Johnsson, Lund (SE); Hannicka Maria Eleonora Sahlstedt, Malmö (SE)

(73) Assignee: EXINI Diagnostics AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/209,676

(22) Filed: Jun. 14, 2023

(65) Prior Publication Data

US 2023/0420112 A1 Dec. 28, 2023

Related U.S. Application Data

(63) Continuation of application No. 17/008,411, filed on Aug. 31, 2020, now Pat. No. 11,721,428.

(Continued)

(51) Int. Cl.
*G16H 30/40* (2018.01)
*G06T 7/00* (2017.01)
(Continued)

(52) U.S. Cl.
CPC .......... *G16H 30/40* (2018.01); *G06T 7/0012* (2013.01); *G06T 7/11* (2017.01); *G16H 50/20* (2018.01);
(Continued)

(58) Field of Classification Search
CPC ........ G16H 50/30; G16H 10/60; G16H 50/20; G16H 70/60; G16H 30/40; G16H 30/20;
(Continued)

(56) References Cited

U.S. PATENT DOCUMENTS

| 5,762,608 A | 6/1998 | Warne et al. |
| 6,944,330 B2 | 9/2005 | Novak et al. |

(Continued)

FOREIGN PATENT DOCUMENTS

| CN | 1200520 A | 12/1998 |
| CN | 1518719 A | 8/2004 |

(Continued)

OTHER PUBLICATIONS

Machine translation of JP-2017067489-A (Year: 2017).*
(Continued)

*Primary Examiner* — Aaron W Carter
*Assistant Examiner* — Courtney Joan Nelson
(74) *Attorney, Agent, or Firm* — Choate, Hall & Stewart LLP; William R. Haulbrook; Ronen Adato

(57) ABSTRACT

Presented herein are systems and methods that provide for improved detection and characterization of lesions within a subject via automated analysis of nuclear medicine images, such as positron emission tomography (PET) and single photon emission computed tomography (SPECT) images. In particular, in certain embodiments, the approaches described herein leverage artificial intelligence (AI) to detect regions of 3D nuclear medicine images corresponding to hotspots that represent potential cancerous lesions in the subject. The machine learning modules may be used not only to detect presence and locations of such regions within an image, but also to segment the region corresponding to the lesion and/or classify such hotspots based on the likelihood that they are indicative of a true, underlying cancerous lesion. This AI- (Continued)

based lesion detection, segmentation, and classification can provide a basis for further characterization of lesions, overall tumor burden, and estimation of disease severity and risk.

32 Claims, 18 Drawing Sheets
(3 of 18 Drawing Sheet(s) Filed in Color)

Related U.S. Application Data

(60) Provisional application No. 63/048,436, filed on Jul. 6, 2020.

(51) Int. Cl.
*G06T 7/11* (2017.01)
*G16H 50/20* (2018.01)
*G16H 50/30* (2018.01)

(52) U.S. Cl.
CPC ... *G16H 50/30* (2018.01); *G06T 2207/10072* (2013.01); *G06T 2207/30056* (2013.01); *G06T 2207/30096* (2013.01)

(58) Field of Classification Search
CPC ......... G06T 7/0012; G06T 2207/30096; G06T 2207/20081; G06T 2207/20084; G06T 2207/10104; G06T 2207/10108; G06T 7/10; G06T 2207/30056; G06T 2210/41; G06T 7/0014; G06T 7/174; G06T 15/00; G06T 2200/24; G06T 7/11; G06T 2207/10072; A61B 6/469; A61B 6/465; A61B 5/7425; A61B 8/08; A61B 8/085; A61B 8/483; A61B 8/5223; G06V 10/82; G06V 10/25; G06N 20/00
See application file for complete search history.

(56) References Cited

U.S. PATENT DOCUMENTS

| | | | |
|---|---|---|---|
| 7,450,747 B2 | 11/2008 | Jabri et al. |
| 7,751,605 B2 | 7/2010 | Gündel et al. |
| 7,876,938 B2 | 1/2011 | Huang et al. |
| 7,935,055 B2 | 5/2011 | Burckhardt |
| 7,970,194 B2 | 6/2011 | Kimura |
| 8,199,985 B2 | 6/2012 | Jakobsson et al. |
| 8,211,401 B2 | 7/2012 | Babich et al. |
| 8,467,856 B2 | 6/2013 | Renisch et al. |
| 8,538,166 B2 | 9/2013 | Gordon et al. |
| 8,606,349 B2 * | 12/2013 | Rousso ................ G01T 1/1642 424/9.1 |
| 8,705,887 B2 | 4/2014 | Ma et al. |
| 8,778,305 B2 | 7/2014 | Pomper et al. |
| 8,855,387 B2 | 10/2014 | Hamadeh et al. |
| 8,962,799 B2 | 2/2015 | Babich et al. |
| 8,995,736 B2 | 3/2015 | Kaufman et al. |
| 9,002,081 B2 | 4/2015 | Brown |
| 9,466,133 B2 | 10/2016 | Sowards-Emmerd et al. |
| 9,710,915 B2 | 7/2017 | Firouzian et al. |
| 9,721,340 B2 | 8/2017 | Gillies et al. |
| 10,058,393 B2 | 8/2018 | Bonutti et al. |
| 10,223,610 B1 | 3/2019 | Akselrod-Ballin et al. |
| 10,311,971 B2 | 6/2019 | Opfer et al. |
| 10,330,763 B2 | 6/2019 | James et al. |
| 10,339,653 B2 | 7/2019 | Gillies et al. |
| 10,340,044 B2 | 7/2019 | Yao et al. |
| 10,340,046 B2 | 7/2019 | Baker |
| RE47,609 E | 9/2019 | Hamadeh et al. |
| 10,492,723 B2 | 12/2019 | Madabhushi et al. |
| 10,600,184 B2 | 3/2020 | Golden et al. |
| 10,665,346 B2 | 5/2020 | Baker |
| 10,748,652 B2 | 8/2020 | Yao et al. |
| 10,762,993 B2 | 9/2020 | Baker |
| 10,818,386 B2 | 10/2020 | Yao et al. |
| 10,943,681 B2 | 3/2021 | Yao et al. |
| 10,973,486 B2 | 4/2021 | Sjöstrand et al. |
| 11,011,257 B2 | 5/2021 | Lints et al. |
| 11,094,066 B2 | 8/2021 | Nie et al. |
| 11,321,844 B2 | 5/2022 | Johnsson et al. |
| 11,386,988 B2 | 7/2022 | Johnsson et al. |
| 11,424,035 B2 | 8/2022 | Baker |
| 11,508,059 B2 | 11/2022 | Wang et al. |
| 11,534,125 B2 | 12/2022 | Sjöstrand et al. |
| 11,564,621 B2 | 1/2023 | Anand et al. |
| 11,657,508 B2 | 5/2023 | Richter et al. |
| 11,721,428 B2 | 8/2023 | Brynolfsson et al. |
| 11,894,141 B2 | 2/2024 | Baker |
| 11,900,597 B2 | 2/2024 | Anand et al. |
| 11,937,962 B2 | 3/2024 | Sjöstrand et al. |
| 11,941,817 B2 | 3/2024 | Richter et al. |
| 2003/0215120 A1 | 11/2003 | Uppaluri et al. |
| 2005/0065421 A1 | 3/2005 | Burckhardt |
| 2005/0281381 A1 | 12/2005 | Guendel |
| 2006/0062425 A1 | 3/2006 | Shen et al. |
| 2006/0064396 A1 | 3/2006 | Wei et al. |
| 2006/0078183 A1 | 4/2006 | deCharms |
| 2007/0081712 A1 * | 4/2007 | Huang ................ G06T 7/155 382/128 |
| 2007/0081713 A1 | 4/2007 | Jerebko |
| 2007/0100225 A1 | 5/2007 | Maschke |
| 2007/0115204 A1 | 5/2007 | Budz et al. |
| 2008/0027315 A1 | 1/2008 | McGinnis |
| 2009/0309874 A1 | 12/2009 | Salganicoff et al. |
| 2009/0311182 A1 | 12/2009 | Wang et al. |
| 2010/0215581 A1 | 8/2010 | Hoffmann |
| 2010/0266170 A1 | 10/2010 | Khamene et al. |
| 2010/0322488 A1 | 12/2010 | Virtue et al. |
| 2011/0063288 A1 | 3/2011 | Valadez |
| 2011/0255763 A1 | 10/2011 | Bogoni et al. |
| 2012/0123253 A1 | 5/2012 | Renisch et al. |
| 2013/0038707 A1 | 2/2013 | Cunningham et al. |
| 2013/0094704 A1 | 4/2013 | Hamadeh et al. |
| 2013/0129168 A1 | 5/2013 | Ross |
| 2013/0211231 A1 | 8/2013 | Sundarapandian et al. |
| 2013/0281841 A1 | 10/2013 | Everett et al. |
| 2014/0193336 A1 | 7/2014 | Rousso et al. |
| 2015/0003703 A1 | 1/2015 | Franz et al. |
| 2015/0110716 A1 | 4/2015 | Armor |
| 2015/0119704 A1 | 4/2015 | Roth et al. |
| 2015/0331995 A1 | 11/2015 | Zhao et al. |
| 2015/0356730 A1 | 12/2015 | Grove et al. |
| 2016/0203263 A1 | 7/2016 | Maier et al. |
| 2016/0275674 A1 | 9/2016 | Rivet-Sabourin et al. |
| 2016/0335395 A1 | 11/2016 | Wu et al. |
| 2017/0083682 A1 | 3/2017 | McNutt et al. |
| 2017/0112577 A1 | 4/2017 | Bonutti et al. |
| 2018/0144828 A1 | 5/2018 | Baker |
| 2018/0259608 A1 | 9/2018 | Golden et al. |
| 2018/0360402 A1 | 12/2018 | Carmi |
| 2019/0038239 A1 | 2/2019 | Flohr et al. |
| 2019/0105009 A1 | 4/2019 | Siemionow et al. |
| 2019/0209116 A1 | 7/2019 | Sjostrand et al. |
| 2019/0388049 A1 | 12/2019 | Gupta et al. |
| 2020/0027559 A1 | 1/2020 | Baker |
| 2020/0051238 A1 | 2/2020 | El Harouni et al. |
| 2020/0074634 A1 | 3/2020 | Kecskemethy et al. |
| 2020/0085382 A1 | 3/2020 | Taerum et al. |
| 2020/0126666 A1 | 4/2020 | Baker |
| 2020/0170604 A1 | 6/2020 | Yildirim et al. |
| 2020/0193594 A1 | 6/2020 | Georgescu et al. |
| 2020/0193603 A1 | 6/2020 | Golden et al. |
| 2020/0245960 A1 | 8/2020 | Richter et al. |
| 2020/0311919 A1 | 10/2020 | Grimmer et al. |
| 2020/0315455 A1 | 10/2020 | Lee et al. |
| 2020/0337658 A1 | 10/2020 | Sjostrand et al. |
| 2020/0342600 A1 | 10/2020 | Sjostrand et al. |
| 2020/0352518 A1 | 11/2020 | Lyman et al. |
| 2020/0357117 A1 | 11/2020 | Lyman et al. |
| 2020/0357118 A1 | 11/2020 | Yao et al. |
| 2020/0357521 A1 | 11/2020 | Baker |
| 2020/0410672 A1 | 12/2020 | Katscher et al. |
| 2021/0032206 A1 | 2/2021 | Neumaier et al. |

(56) References Cited

U.S. PATENT DOCUMENTS

| | | |
|---|---|---|
| 2021/0082547 A1 | 3/2021 | Yao et al. |
| 2021/0093249 A1 | 4/2021 | Anand et al. |
| 2021/0183485 A1 | 6/2021 | Yao et al. |
| 2021/0233633 A1 | 7/2021 | Lints et al. |
| 2021/0334974 A1 | 10/2021 | Johnsson et al. |
| 2021/0335480 A1 | 10/2021 | Johnsson et al. |
| 2022/0005586 A1 | 1/2022 | Brynolfsson et al. |
| 2022/0375612 A1 | 11/2022 | Baker |
| 2022/0398724 A1 | 12/2022 | Anand et al. |
| 2023/0115732 A1 | 4/2023 | Brynolfsson et al. |
| 2023/0148980 A1 | 5/2023 | Sjöstrand et al. |
| 2023/0316530 A1 | 10/2023 | Richter et al. |
| 2023/0351586 A1 | 11/2023 | Brynolfsson et al. |
| 2023/0410985 A1 | 12/2023 | Brynolfsson et al. |
| 2024/0029252 A1 | 1/2024 | Ichinose et al. |
| 2024/0127437 A1 | 4/2024 | Anand et al. |
| 2024/0169546 A1 | 5/2024 | Richter et al. |
| 2024/0186010 A1 | 6/2024 | Baker |
| 2024/0285246 A1 | 8/2024 | Sjöstrand et al. |
| 2024/0285248 A1 | 8/2024 | Sjöstrand et al. |
| 2024/0354940 A1 | 10/2024 | Sjöstrand et al. |

FOREIGN PATENT DOCUMENTS

| | | | |
|---|---|---|---|
| CN | 101528267 A | 9/2009 | |
| CN | 101639937 A | 2/2010 | |
| CN | 102096804 A | 6/2011 | |
| CN | 102361594 A | 2/2012 | |
| CN | 102438529 A | 5/2012 | |
| CN | 102947840 A | 2/2013 | |
| CN | 103607954 A | 2/2014 | |
| CN | 106127819 A | 11/2016 | |
| CN | 106558045 A | 4/2017 | |
| CN | 107563378 A | 1/2018 | |
| CN | 107644421 A | 1/2018 | |
| CN | 114219787 A | 3/2022 | |
| EP | 1426903 A2 | 6/2004 | |
| EP | 1508872 A1 | 2/2005 | |
| EP | 2816525 A1 | 12/2014 | |
| EP | 3043318 A1 | 7/2016 | |
| GB | 2457577 A | 8/2009 | |
| JP | 2010-029481 A | 2/2010 | |
| JP | 2011-067594 A | 4/2011 | |
| JP | 2014-006130 A | 1/2014 | |
| JP | 2015-513083 A | 4/2015 | |
| JP | 6013042 B2 | 10/2016 | |
| JP | 2017-500537 A | 1/2017 | |
| JP | 2017067489 A * | 4/2017 | |
| JP | 6170284 B2 | 7/2017 | |
| JP | 2017-198697 A | 11/2017 | |
| SE | 524500 C2 | 8/2004 | |
| TW | 201201847 A | 1/2012 | |
| WO | WO-99/05503 A2 | 2/1999 | |
| WO | WO-2007/062135 A2 | 5/2007 | |
| WO | WO-2009/084995 A1 | 7/2009 | |
| WO | WO-2010/071999 A1 | 7/2010 | |
| WO | WO-2011/077303 A1 | 6/2011 | |
| WO | WO-2011/091378 A1 | 7/2011 | |
| WO | WO-2011/095580 A1 | 8/2011 | |
| WO | WO-2013/126147 A2 | 8/2013 | |
| WO | WO-2015/058151 A2 | 4/2015 | |
| WO | WO-2016087592 A1 * | 6/2016 | ....... G01N 33/57415 |
| WO | WO-2018/014475 A1 | 1/2018 | |
| WO | WO-2018/015953 A1 | 1/2018 | |
| WO | WO-2018081354 A1 * | 5/2018 | ............ A61B 6/037 |
| WO | WO-2019/005722 A1 | 1/2019 | |
| WO | WO-2019/103912 A2 | 5/2019 | |
| WO | WO-2019136349 A2 * | 7/2019 | ............ A61B 6/032 |
| WO | WO-2020/144134 A1 | 7/2020 | |
| WO | WO-2020/146032 A1 | 7/2020 | |
| WO | WO-2020/190821 A1 | 9/2020 | |
| WO | WO-2020/219619 A1 | 10/2020 | |
| WO | WO-2020/219620 A1 | 10/2020 | |
| WO | WO-2021/061315 A1 | 4/2021 | |
| WO | WO-2022/008374 A1 | 1/2022 | |
| WO | WO-2022/215530 A1 | 10/2022 | |
| WO | WO-2023/057411 A9 | 7/2023 | |
| WO | WO-2023/239829 A2 | 12/2023 | |
| WO | WO-2024/173297 A1 | 8/2024 | |
| WO | WO-2024/211651 A1 | 10/2024 | |

OTHER PUBLICATIONS

Partin, A.W. et al., Combination of prostate-specific antigen, clinical stage, and Gleason score to predict pathological stage of localized prostate cancer. A multi-institutional update, JAMA, 277(18):1445-1451 (1997).

Partin, A.W. et al., The use of prostate specific antigen, clinical stage and Gleason score to predict pathological stage in men with localized prostate cancer, J. Urol., 150(1):110-114 (1993).

Poulakis, V. et al., Preoperative neural network using combined magnetic resonance imaging variables, prostate specific antigen, and Gleason score to predict prostate cancer recurrence after radical prostatectomy, Eur. Urol., 46(5):571-578 (2004).

Ali, A. et al., The Automated Bone Scan Index as a Predictor of Response to Prostate Radiotherapy in Men with Newly Diagnosed Metastatic Prostate Cancer: An Exploratory Analysis of Stampede's "M1|RT Comparison", European Urology Oncology 3:412-419, (2020).

American College of Radiology (ACR) and the Society for Pediatric Radiology (SPR), ACR-SPR Practice Parameter For The Performance Of Skeletal Scintigraphy (Bone Scan), Resolution 28, (2013-Revused2017), available from: <http://www.acr.org>, 9 pages (2017).

Anand, A. et al., A Pre-Analytical Validation Study of Automated Bone Scan Index: Effect on Accuracy and Reproducibility Due to the Procedural Variabilities in Bone Scan Image Acquisition. J Nucl Med. pp. 1865-1871, (2016).

Anand, A. et al., Analytic Validation of the Automated Bone Scan Index as an Imaging Biomarker to Standardize Quantitative Changes in Bone Scans of Patients with Metastatic Prostate Cancer, J. Nucl. Med., 57(1):41-45 (2016).

Anand, A. et al., Automated Bone Scan Index as a quantitative imaging biomarker in metastatic castration-resistant prostate cancer patients being treated with enzalutamide, EJNMMI Research, 6:23, 7 pages (2016).

Anand, A. et al., Translating Prostate Cancer Working Group 2 (PCWG2) Progression Criteria into a Quantitative Response Biomarker in Metastatic Castration Resistant Prostate Cancer (mCRPC), ASCO GU Conference, Poster, 1 page, presented Feb. 16, 2017.

Anand, A. et al., Translating Prostate Cancer Working Group 2 (PCWG2) progression criteria into a quantitative response biomarker in metastatic castration-resistant prostate cancer (mCRPC), Journal of Clinical Oncology, 35(6):170 (2017).

Armstrong, A. et al., Assessment of the bone scan index in a randomized placebo-controlled trial of tasquinimod in men with metastatic castration-resistant prostate cancer (mCRPC), Urologic Oncology: Seminars and Original Investigations, 32:1308-1316 (2014).

Armstrong, A. et al., Development and validation of a prognostic model for overall survival in chemotherapy-naive men with metastatic castration-resistant prostate cancer (mCRPC) from the phase 3 prevail clinical trial, Journal of Clinical Oncology, 35(Suppl. 6):Abstract 138, 5 pages, (2017).

Armstrong, A. J. et al., Phase 3 Assessment of the Automated Bone Scan Index as a Prognostic Imaging Biomarker of Overall Survival in Men with Metastatic Castration-Resistant Prostate Cancer: A Secondary Analysis of a Randomized Clinical Trial. JAMA Oncology 4:944-951, (2018).

Armstrong, A. J. et al., Phase 3 prognostic analysis of the automated bone scan index (aBSI) in men with bone-metastatic castration-resistant prostate cancer (CRPC), Meeting Library ASC University, 11 pages (2017).

Bai, P. et. al., Body region localization in whole-body low-dose CT images of PET/CT scans using virtual landmarks, Medical Physics Wiley USA, 46(3): 1286-1299 (2019).

(56) References Cited

OTHER PUBLICATIONS

Belal, S. et al., Association of PET Index quantifying skeletal uptake in NaF PET/CT images with overall survival in prostate cancer patients, ASCO GU 2017, Poster 178, 1 page, presented Feb. 16, 2017.

Belal, S. et al., PET Index quantifying skeletal uptake in NaF PET/CT images with overall survival in prostate cancer patients, ASCO GU 2017, Abstract, 1 page, (Feb. 13, 2017).

Belal, S. L. et al., 3D skeletal uptake of $^{18}$F sodium fluoride in PET/CT images is associate with overall survival in patients with prostate cancer, EJNMMI Research, 7(15):1-8 (2017).

Belal, S.L. et al., Automated evaluation of normal uptake in different skeletal parts in 18F-sodium fluoride (NaF) PET/CT using a new convolutional neural network method, EJNMMI, EANM '17, 44(Suppl 2):S119-S956, Abstract EP-0116 (2017).

Bombardieri, E. et al., Bone scintigraphy: procedure guidelines for tumour imaging, Eur J. Nucl. Med. Mol. Imaging, 30:BP99-BP106, (2003).

Brynolfsson, J., et al., Deep Learning based urinary bladder segmentation using 18FDCFPyL (PyL-PSMA) PET/CT images, EPS-145, European Association of Nuclear Medicine, (2020), <http://link.springer.com/article/10.1007/s00259-020-04988-4>. pp. S1 and S403-S404, Retrieved Sep. 18, 2020.

Brynolfsson, J., et al., Deep Learning-Enabled comprehensive detection and quantification of 18FDCFPyL (PyL-PSMA) PET/CT, OP-548, European Association of Nuclear Medicine, (2020), <http://link.springer.com/article/10.1007/s00259-020-04988-4>. pp. S1 and S273, Retrieved Sep. 18, 2020.

Bushberg, J. T. et al., Essential Physics of Medical Imaging, Essential Physics of Medical Imaging, 19.3: p. 581 (table 15-3), p. 713 paragraph 6, section 19.3 and p. 720, (2011).

Capobianco, N. et al., Whole-body uptake classification and prostate cancer staging in $^{68}$Ga-PSMA-11 PET/CT using dual-tracer learning, European Journal of Nuclear Medicine and Molecular Imaging, (2021), <https:/doi.org/10.1007/s00259-021-05473-2> 10 pages. Retrieved on Apr. 18, 2021.

Ceci, F. et al., E-PSMA: the EANM standardized reporting guidelines v1.0 for PSMA-PET, European Journal of Nuclear Medicine and Molecular Imaging, 48:1626-1638, (2021).

Cha, K. H., et al. Urinary bladder segmentation in CT urography using deep-learning convolutional neural network and level sets, Medical physics, 43(4):1882-1896, (2016).

Christ, P.F. et al., Automatic Liver and Tumor Segmentation of CT and MRI Volumes Using Cascaded Fully Convolutional Neural Networks, Arxiv.org, Cornell University Library, 20 pages, (2017).

Ciernik, I. F., et al. 3D-segmentation of the 18F-choline PET signal for target volume definition in radiation therapy of the prostate, Technology in cancer research & treatment 6(1):23-30, (2007).

Dennis, E. et al., Bone Scan Index: A Quantitative Treatment Response Biomarker for Castration-Resistant Metastatic Prostate Cancer, Journal of Clinical Oncology, 30(5):519-524 (2012).

Dertat, A., Applied Deep Learning—Part 4: Convolutional Neural Networks, Towards Data Science,<http://towardsdatascience.com/applied-deep-learning-part-4-convolutional-neural-networks-584bc134c1e2> 26 pages, (2017).

Eiber, M. et al., Prostate Cancer Molecular Imaging Standardized Evaluation (PROMISE): Proposed miTNM Classification for the Interpretation of PSMA-Ligand PET/CT, The Journal of Nuclear Medicine, 59(3):469-478, (2018).

Fendler, W.P. et al., $^{68}$Ga-PSMA PET/CT: Joint EANM and SNMMI procedure guideline for prostate cancer imaging: version 1.0, Eur J Nucl Med Mol Imaging, DOI 10.1007/s00259-017-3670-z, 11 pages, (2017).

Gafita, A. et al., Novel Framework for Treatment Response Evaluation Using PSMA PET/CT in Patients with Metastatic Castration-Resistant Prostate Cancer (RECIP 1.0): An International Multicenter Study, J. Nucl. Med., 63(11):1651-1658 (2022).

GE Healthcare, SPECT/CT Cameras, 2 pages, retrieved Oct. 25, 2017: <http://www3.gehealthcare.com.sg/en-gb/products/categories/nuclear_medicine/spect-ct_cameras>.

Giesel, F. L. et al., F-18 labelled PSMA-1007: biodistribution, radiation dosimetry and histopathological validation of tumor lesions in prostate cancer patients, Eur. J. Nucl. Med. Mol. Imaging, 44:678-688 (2017).

Gjertsson, K., et al., A Novel Automated Deep Learning Algorithm for Segmentation of the Skeleton in Low-Dose CT for [(18)F] DCFPyL PET/CT Hybrid Imaging in Patients with Metastatic Prostate Cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0823, p. S765.

Gjertsson, K., Segmentation in Skeletal Scintigraphy Images using Convolutional Neural Networks, Master's Theses in Mathematical Sciences, pp. 39-58, (2017), <https://lup.lub.lu.se/student-papers/search/publication/8916406>.

Goffin, K. E. et al., Phase 2 study of 99mTc-trofolastat SPECT/CT to identify and localize prostate cancer in intermediate- and high-risk patients undergoing radical prostatectomy and extended pelvic lymph node dissection, J. Nucl. Med., 27 pages (2017).

Gorthi, S. et al., Segmentation of Head and Neck Lymph Node Regions for Radiotherapy Planning Using Active Contour-Based Atlas Registration, IEEE Journal of Selected Topics in Signal Processing, 3(1):135-147 (2009).

Grahovac, M. et al., Machine learning predictive performance evaluation of conventional and fuzzy radiomics in clinical cancer imaging cohorts, Eur. J. Med. Mol. Imaging, 50(6):1607-1620 (2023).

Guimond, A. et al., Average Brain Models: A Convergence Study, Computer Vision and Image Understanding, 77:192-210 (2000).

Hajnal, J. et al., 4.4 Intensity, Size, and Skew Correction; 7.1 Introduction; 7.2 Methods; 7.3 Image Interpretation—General, In: Medical Image Registration, CRC Press LLC, 80-81:144-148 (2001).

Hiller, S. M. et al., 99mTc-Labeled Small-Molecule Inhibitors of Prostate-Specific Membrane Antigen for Molecular Imaging of Prostate Cancer, Journal of Nuclear Medicine, 54(8):1369-1376 (2013) retrieved Oct. 25, 2017: <http://jnm.snmjournals.org/content/54/8/1369.full>.

Horikoshi, H. et al., Computer-aided diagnosis system for bone scintigrams from Japanese patients: importance of training database, Annals of Nuclear Medicine, 26(8):622-626 (2012).

Huang, J.-H. et al., A Set of Image Processing Algorithms for Computer-Aided Diagnosis in Nuclear Medicine Whole Body Bone Scan Images, IEEE Transactions on Nuclear Science, 54(3):514-522 (2007).

Im, HJ, et al., et al., Current Methods to Define Metabolic Tumor Volume in Positron Emission Tomography: Which One is Better?, Nucl. Med. Mol. Imaging, 52(1):5-15, (2018).

Inoue, T., What cancers can be understood and not known by "PET"?—Effects of PET scanning by site, Medical Note Interview, 4 pages, (2015), retrieved from the internet at: https://medicalnote.jp/contents/150715-000003-CYJIZE.

International Search Report, International Application No. PCT/EP2021/068337, 7 pages, (mailed Dec. 9, 2021).

Johnsson, K. et al., Analytical performance of aPromise: automated anatomic contextualization, detection, and quantification of [18F]DCFPyL (PSMA) imaging for standardized reporting, European Journal of Nuclear Medicin and Molecular Imaging, 11 pages, Aug. 31, 2021, doi: 10.1007/s00259-021-05497-8. Epub ahead of print. PMID: 34463809.

Johnsson, K., et al., miPSMA Index: Comprehensive and Automated Quantification of 18F-DCFPyL (PyL-PSMA) PET/CT for Prostate Cancer Staging, J Nucl Med., 61: (Supplement 1): 1435, 5 pages, (2020).

Kaboteh R. et al., Progression of bone metastases in patients with prostate cancer—automated detection of new lesions and calculation of bone scan index, EJNMMI Research, 3:64, 6 pages, (2013).

Kaboteh, R. et al., Convolutional neural network based quantification of choline uptake in PET/CT studies is associated with overall survival in patents with prostate cancer, EJNMMI, EANM '17, 44(Suppl 2):S119-S956, Abstract EP-0642 (2017).

Kawakami, K. et al., Introduction of bone scintigraphy diagnosis support software "Bonenavi" (Topics), Journal of Nuclear Medicine (Japanese), 63:41-51 (2011).

(56) References Cited

OTHER PUBLICATIONS

Kawakami, K., Evaluation of bone metastasis by bone scintigraphy diagnostic support software Bonenavi, Communication of the Imaging Group of the JSRT, 36(1):74-77 (2013).
Kertesz, H. et al., Implementation of a Spatially-Variant and Tissue-Dependent Positron Range Correction for PET/CT Imaging, Front. Physiol., 13:818463 (2022).
Kertesz, H. et al., Positron range in combination with point-spread-function correction: an evaluation of different implementations for [124I]-PET imaging, ENJMMI Phys., 9(1):56 (2022).
Khurshid, Z. et al., Role of textural heterogeneity parameters in patient selection for 177Lu-PSMA therapy via response prediction, Oncotarget., 9(70):33312-33321 (2018).
Kiess, et al., Prostate-specific membrane antigen and a target for cancer imaging and therapy, The Quarterly Journal of Nuclear Medicine and Molecular Imaging, 59(3):241-268 (2015).
Kikuchi, A. et al., Automated segmentation of the skeleton in whole-body bone scans: influence of difference in atlas, Nuclear Medicine Communications, 33(9):947-953 (2012).
Kinahan, P.E. et al., PET/CT Standardized Update Values (SUVs) in Clinical Practice and Assessing Response to Therapy, Semin Ultrasound CT MR 31(6):496-505 (2010) retrieved Oct. 25, 2017: <https://www.ncbi.nlm.nih.gov/pmc/articles/PMC3026294/>.
Knutsson, H., and Andersson, M., Morphons: Segmentation using Elastic Canvas and Paint on Priors, IEEE International Conference on Image Processing (ICIP 2005), Genova, Italy, 4 pages (2005).
Kopka, K. et al., Glu-Ureido-Based Inhibitors of Prostate-Specific Membrane Antigen: Lessons Learned During the Development of a Novel Class of Low-Molecular-Weight Theranostic Radiotracers, The Journal of Nuclear Medicine, 58(9)(Suppl. 2):17S-26S, (2017).
Krajnc, D. et al., Automated data preparation for in vivo tumor characterization with machine learning, Front. Oncol., 12:1017911 (2022).
Lin, T.Y. et al., Feature Pyramid Networks for object detection, FAIR, 10 pages, (2016), <https://arxiv.org/abs/1612.03144v1>.
Litjens, G. et al., A survey on deep learning in medical image analysis, Medical Image Analysis, 42:60-88, (2017).
Liu, L. et al., Computer-Aided Detection of Prostate Cancer with MRI: Technology and Applications, Acad Radiol. Author manuscript, 50 pp. 2016.
Ma, L. et al., Automatic segmentation of the prostate on CT images using deep learning and multi-atlas fusion, Proc. of SPIE vol. 10133:1013320-1-1013320-9 (2017).
Ma, L. et al., Combining Population and Patient-Specific Characteristics for Prostate Segmentation on 3D CT Images, Proc of SPIE 9784:978427-1-8 (2016).
Ma, L. et al., Random Walk Based Segmentation for the Prostate on 3D Transrectal Ultrasound Images, Proc SPIE Int Soc Opt Eng. Author manuscript, 13 pages (2016).
Matsubara, N. et al., A Phase II, Randomized, Open-Label, Multiarm Study of TAS-115 for Castration-Resistant Prostate Cancer Patients With Bone Metastases, Clinical Genitourinary Cancer, 000(xxx):1-10, (2021).
Mayo Clinic Staff, Choline C-11 Pet scan, Overview, Mayo Clinic, 4 pages (2017), retrieved Oct. 25, 2017: <https://www.mayoclinic.org/tests-procedures/choline-c-11-pet-scan/home/ovc-20156994>.
Meyer, A., et al., Deep learning algorithm improves identification of men with low-risk prostate cancer using PSMA targeted 99mTc-MIP-1404 SPECT/CT, Journal of Clinical Oncology, 37:(15), (2019).
Nakajima, K. et al., Enhanced diagnostic accuracy for quantitative bone scan using an artificial neural network system: a Japanese multi-center database project, EJNMMI Research, 3:83, 9 pages, (2013).
National Cancer Institute, NCI Drug Dictionary: gallium Ga 68-labeled PSMA-11, 1 page, retrieved Oct. 25, 2017: <https://www.cancer.gov/publications/dictionaries/cancer-drug?cdrid=766400>.
National Cancer Institute, NCI Drug Dictionary: technetium Tc 99m methylene diphosphonate, 1 page, retrieved Oct. 25, 2017: <https://www.cancer.gov/publications/dictionaries/cancer-drug?cdrid=537722>.
Nickols, N. et al., aPROMISE: A Novel Automated-PROMISE platform to Standardize Evaluation of Tumor Burden in 18F-DCFPyL (PSMA) images of Veterans with Prostate Cancer, Journal of Nuclear Medicine, 26 pages, May 28, 2021, doi: 10.2967/jnumed.120.261863.
Nickols, N.G., et. al., A deep learning algorithm to predict coexisting metastatic disease using intraprostatic [F18]DCFPYL PSMA image alone in veterans with prostate cancer, Journal of Clinical Oncology 38, (Supplement 6), 2020.
Nogi, S. et al., Metastatic bone tumor quantified by computer-assisted diagnosis system of bone scintigraphy, Nuclear Medicine in Clinic, 45(3):35-37 (2012).
Ohlsson, M., et al., Automated decision support for bone scintigraphy, Computer-based medical systems, pp. 1-6, (2009).
Papp, L. et al., Glioma Survival Prediction with Combined Analysis of In Vivo 11C-MET Pet Features, Ex Vivo Features, and Patient Features by Supervised Machine Learning, J. Nucl. Med., 59(6):892-899 (2018).
Papp, L. et al., Optimized Feature Extraction for Radiomics Analysis of 18F-FDG PET Imaging, J. Nucl. Med., 60(6):864-872 (2019).
Papp, L. et al., Supervised machine learning enables non-invasive lesion characterization in primary prostate cancer with [68Ga]Ga-PSMA-11 PET/MRI, Eur. J. Nucl. Mol. Imaging, 48(6):1795-1805 (2021).
Partial Search Report and Provisional Opinion, International Application No. PCT/EP2021/068337, 8 pages, mailed Oct. 18, 2021.
Paschalis, A. et al., Prostate-specific Membrane Antigen Heterogeneity and DNA Repair Defects in Prostate Cancer, European Urology, 76(4):469-478, (2019).
Perera, M. et al., Sensitivity, Specificity, and Predictors of Positive 68Ga-Prostate-specific Membrane Antigen Positron Emission Tomography in Advanced Prostate Cancer: A Systematic Review and Meta-analysis, European Urology, 70(6):926-937 (2016).
Polymeri, E. et al., Analytical validation of an automated method for segmentation of the prostate gland in CT images, EJNMMI, EANM '17, 44(Suppl 2):S119-S956, Abstract EP-0641 (2017).
Polymeri, E., et al., Deep learning-based quantification of PET/CT prostate gland uptake: association with overall survival, Clinical Physiology Functional Imaging, DOI: 10.1111/cpf.12611, 40(2):106-113, (2019).
Pouliot, F., et al., Prospective evaluation of a Novel Deep Learning Algorithm (PSMA-AI) in the assessment of 99mTc-MIP-1404 SPECT/CT in patients with low or intermediate risk prostate cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0804, p. S765.
Radiologyinfo.Org for Patients, Computed Tomography (CT), 2 pages, retrieved Oct. 25, 2017: < https://www.radiologyinfo.org/en/submenu.cfm?pg=ctscan>.
Ren, S., et al., Faster R-CNN: Towards Real-Time Object Detection with Region Proposal Networks, 14 pages. (2015), <http://image-net.org/challenges/LSVRC/2015/results>.
Ronneberger, O., et al., U-Net: Convolutional Networks for Biomedical Image Segmentation, Springer International Publishing, pp. 234-241, (2015), <http://lmb.informatik.uni-freiburg.de/>. Published online on Nov. 18, 2015.
Rowe, S. P. et al., PET Imaging of prostate-specific membrane antigen in prostate cancer: current state of the art and future challenges, Prostate Cancer and Prostatic Diseases, pp. 1-8 (2016).
Rowe, S. P. et al., PSMA-Based [18F]DCFPyL PET/CT Is Superior to Conventional Imaging for Lesion Detection in Patients with Metastatic Prostate Cancer, Mol Imaging Biol, 18:411-419, (2016).
Sabbatini, P. et al., Prognostic Significance of Extent of Disease in Bone in Patients With Androgen-Independent Prostate Cancer, Journal of Clinical Oncology, 17(3):948-957 (1999).
Sadik, M. et al., 3D prostate gland uptake of 18F-choline - association with overall survival in patients with hormone-naïve prostate cancer, The Journal of Nuclear Medicine, 58(Suppl. 1): Abstract 544, 2 pages, (2017).
Sadik, M. et al., A new computer-based decision-support system for the interpretation of bone scans, Nuclear Medicine Communications, 27(5):417-423 (2006).

(56) References Cited

OTHER PUBLICATIONS

Sadik, M. et al., Automated 3D segmentation of the prostate gland in CT images - a first step towards objective measurements of prostate uptake in PET and SPECT images, Journal of Nuclear Medicine, 58(1):1074, (2017).
Sadik, M. et al., Automated quantification of reference levels in liver and mediastinum (blood pool) for the Deauville therapy response classification using FDG-PET/CT in lymphoma patients, Ejnmmi, Eanm '17, 44(Suppl 2):S119-S956, Abstract EP-0770 (2017).
Sadik, M. et al., Computer-assisted interpretation of planar whole-body bone scans, Journal Nuclear Medicine, 49(12): 1958-65, 2008.
Sadik, M. et al., Convolutional neural networks for segmentation of 49 selected bones in CT images show high reproducibility, Ejnmmi, Eanm '17, 44(Suppl 2):S119-S956, Abstract OP- 657 (2017).
Sadik, M. et al., Improved classifications of planar whole-body bone scans using a computer- assisted diagnosis system: a multicenter, multiple-reader, multiple-case study, Journal of Nuclear Medicine, 50(3): 368-75, 2009.
Sadik, M. et al., Variability in reference levels for Deauville classifications applied to lymphoma patients examined with 18F-FDG-PET/CT, Ejnmmi, Eanm '17, 44(Suppl 2):S119- S956, Abstract EP-0771 (2017).
Sajn, L. et al., Computerized segmentation of whole-body bone scintigrams and its use in automated diagnostics, Computer Methods and Programs in Biomedicine, 80:47-55 (2005).
Salerno, J. et al., Multiparametric magnetic resonance imaging for pre-treatment local staging of prostate cancer: A Cancer Care Ontario clinical practice guideline, Canadian Urological Association Journal, 10(9-10):332-339 (2016).
Santos-Cuevas, C. et al. 99mTc-labeled PSMA inhibitor: Biokinetics and radiation dosimetry in healthy subjects and imaging of prostate cancer tumors in patients, Nuclear Medicine and Biology 52:1-6, (2017).
Seifert, R. et al., Second Version of the Prostate Cancer Molecular Imaging Standardized Evaluation Framework Including Response Evaluation for Clinical Trials (Promise V2), Eur. Urol., 83(5):405-412 (2023).
Shi, F. et al., Deep learning empowered volume delineation of whole-body organs-at-risk for accelerated radiotherapy, Nat. Commun., 13(1):6566 (2022).
Sjöstrand K. et al., Statistical regularization of deformation fields for atlas-based segmentation of bone scintigraphy images, MICCAI 5761:664-671 (2009).
Sjöstrand, K., et. al., Automated detection and quantification of Prostatic PSMA uptake in SPECT/CT using a Deep Learning Algorithm for Segmentation of Pelvic Anatomy, The Journal of Nuclear Medicine, 59(1):p. 30, (2018).
Sjostrand, K., et al., Automated Assessment of Prostatic PSMA Expression in SPECT/CT using Deep Convolutional Neural Networks - A Prospectively Planned Retrospective Analysis of Phase 3 Study MIP-1404-3301, The Journal of Nuclear Medicine, 60 (Supplement 1): Abstract 401, 1 page, (2019).
Sluimer, I. et al., Toward Automated Segmentation of the Pathological Lung in Ct, IEEE Transactions on Medical Imaging, 24(8):1025-1038 (2005).
Teng, C. et al., Head and neck lymph node region delineation using a hybrid image registration method, 3rd IEEE International Symposium on Biomedical Imaging: Nano to Macro, 4 pages, (2006).
Tian, Z. et al., A fully automatic multi-atlas based segmentation method for prostate MR images, Proc SPIE Int Soc Opt Eng. Author manuscript, 12 pages (2015).
Tian, Z. et al., A supervoxel-based segmentation method for prostate MR images, Med. Phys., 44(2):558-569 (2017).
Tian, Z. et al., Deep convolutional neural network for prostate MR segmentation, Proc. of Spie 10135:101351L-1-101351L-6 12 pages, (2017).
Tian, Z., et al., Superpixel-based Segmentation for 3D Prostate MR Images, IEEE Trans Med Imaging, Author manuscript, pp. 558-569, (2016).
Trägardh, E., et al., RECOMIA-a cloud-based platform for artificial intelligence research in nuclear medicine and radiology, EJNMMI Physics, <https://doi.org/10.1186/s40658-020- 00316-9>, 7:51, 12 pages, (2020).
Ulmert, D. et al., A Novel Automated Platform for Quantifying the Extent of Skeletal Tumour Involvement in Prostate Cancer Patients Using the Bone Scan Index, European Urology, 62(1):78-84 (2012).
US Food and Drug Administration, Clinical Trial Endpoints for the Approval of Cancer Drugs and Biologics, 21 pages, (2018).
Valladares, A. et al., A multi-modality physical phantom for mimicking tumor heterogeneity patterns in PET/CT and PET/MRI, Med. Phys., 49(9):5819-5829 (2022).
Wallis, J.W. et al., Three-dimensional display in nuclear medicine, IEEE Trans Med Imaging, 8(4):297-303, (1989).
Washino, H., Injectable for bone scintigraphy: Technetium hydroxymethylenediphosphonate (99mTc) injection solution (Revised Edition), 9 pages, (2007), retrieved from the internet at:https://rada.or.jp/database/home4/normal/ht- docs/member/synopsis/030292.html#:%7E:text=%E6%A6%82%E8%A6%81).
Wrangsjo, A. et al., Non-rigid Registration Using Morphons, Proceedings of the 14th Scandinavian Conference on Image Analysis (SCIA '05), pp. 501-510 (2005).
Written Opinion, International Application No. PCT/EP2021/068337, 13 pages, (mailed Dec. 9, 2021).
Yin, T.K., and Chiu, N.T., A Computer-Aided Diagnosis for Locating Abnormalities in Bone Scintigraphy by a Fuzzy System With a Three-Step Minimization Approach, IEEE Transactions on Medical Imaging, 23(5):639-654 (2004).
Guan, H. et al., Automatic Hot Spot Detection and Segmentation in Whole Body FDG-PET Images, IEEE International Conference on Image Processing, 4 pages, (2006).
Blue Earth Diagnostics, Posluma Highlights of Prescribing Information, 12 pages, (2023).
Emmett, L. et al., The Primary Score: Using Intraprostatic 68Ga-PSMA PET/CT Patterns to Optimize Prostate Cancer Diagnosis, J. Nucl. Med., 63(11):1644-1650 (2022).
Ghosh, P. and Mitchell, M., Prostate segmentation on pelvic CT images using a genetic algorithm, Proceedings of SPIE, vol. 6914, Medical Imaging 2008: Image Processing, 8 pages, (2008).
He, K. et al., Pelvic Organ Segmentation Using Distinctive Curve Guided Fully Convolutional Networks, IEEE Trans. Med. Imaging, 38(2):585-595 (2019).
Benitez, C.M. et al., Treatment Response Assessment According to Updated PROMISE Criteria in Patients with Metastatic Prostate Cancer Using an Automated Imaging Platform for Identification, Measurement, and Temporal Tracking of Disease, European Urology Oncology, 9 pages, (2024).
Defendant's Memorandum of Law in Support of Motion to Dismiss Second Amended Complaint (including Appendix A thereto), *Progenics Pharmaceuticals Inc. and Exini Diagnostics AB v. MIM Software Inc.*, Civil Action No. 1:24-cv-10437-PBS (D. Mass.), Jun. 17, 2024.
Defendant's Motion to Dismiss Second Amended Complaint and Request for Oral Argument, *Progenics Pharmaceuticals Inc. and Exini Diagnostics AB v. MIM Software Inc.*, Civil Action No. 1:24-cv-10437-PBS (D. Mass.), Jun. 17, 2024.
Defendant's Reply Memorandum in Support of Motion to Dismiss Second Amended Complaint, *Progenics Pharmaceuticals Inc. and Exini Diagnostics AB v. MIM Software Inc.*, Civil Action No. 1:24-cv-10437-PBS (D. Mass.), Jul. 26, 2024.
Plaintiffs' Opposition to Defendant's Motion to Dismiss Second Amended Complaint, *Progenics Pharmaceuticals Inc. and Exini Diagnostics AB v. MIM Software Inc.*, Civil Action No. 1:24-cv-10437-PBS (D. Mass.), Jul. 19, 2024.
Plaintiffs' Sur-Reply in Opposition to Defendant's Motion to Dismiss Second Amended Complaint (including Appendix A thereto), *Progenics Pharmaceuticals Inc. and Exini Diagnostics AB v. MIM Software Inc.*, Civil Action No. 1:24-cv-10437-PBS (D. Mass.), Aug. 6, 2024.
Second Amended Complaint, *Progenics Pharmaceuticals Inc. and Exini Diagnostics AB v. MIM Software Inc.*, Civil Action No. 1:24-cv-10437-PBS (D. Mass.), Apr. 5, 2024.

(56) References Cited

OTHER PUBLICATIONS

Chen, X. et al., TensorMask: A Foundation for Dense Object Segmentation, arXiv, 12 pages, (2019).
Chen, X. et al., TensorMask: A Foundation for Dense Object Segmentation, Proceedings of the IEEE/CVF International Conference on Computer Vision (ICCV), 10 pages, (2019).
De Brabandere, B. et al., Semantic Instance Segmentation with a Discriminative Loss Function, arXiv preprint, 10 pages, (2017).
Hatamizadeh, A. et al., UNETR: Transformers for 3D Medical Image Segmentation, Proceedings of the IEEE/CVF Winter Conference on Applications of Computer Vision (WACV), 11 pages, (2022).
Iandola, F.N. et al., SqueezeNet: AlexNet-level accuracy with 50x fewer parameters and <0.5MB model size, arXiv, 13 pages, (2016).
Milletari, F. et al., V-Net: Fully Convolutional Neural Networks for Volumetric Medical Image Segmentation, 2016 Fourth International Conference on 3D Vision (3DV), 11 pages, (2016).
Wan, H., Automated Contouring Using Neural Networks, Contour Protege AI White Paper, 3 pages, (2020), <https://go.mimsoftware.com/contour-protegeai-plus/white-paper>.

* cited by examiner

Quality control

Including lesions in the report requires approval of the image data. Do you approve the following statements?

- ☑ Image quality is acceptable
- ☑ PET and CT Images are correctly aligned
- ☑ Patient study data is correct
- ☑ Reference values (blood pool, liver) are acceptable
- ☑ Study is not a superscan

CREATE REPORT

SYSTEMS AND METHODS FOR ARTIFICIAL INTELLIGENCE-BASED IMAGE ANALYSIS FOR DETECTION AND CHARACTERIZATION OF LESIONS

CROSS-REFERENCE TO RELATED APPLICATION

This application is a continuation of U.S. application Ser. No. 17/008,411, filed Aug. 31, 2020 (now U.S. Pat. No. 11,721,428), which claims priority to and benefit of U.S. Provisional Application 63/048,436, filed Jul. 6, 2020, the content of each of which are hereby incorporated by reference in their entirety.

TECHNICAL FIELD

This invention relates generally to systems and methods for creation, analysis, and/or presentation of medical image data. More particularly, in certain embodiments, the invention relates to systems and methods for automated analysis of medical images to identify and/or characterize cancerous lesions.

BACKGROUND

Nuclear medicine imaging involves the use of radiolabeled compounds, referred to as radiopharmaceuticals. Radiopharmaceuticals are administered to patients and accumulate in various regions in the body in manner that depends on, and is therefore indicative of, biophysical and/or biochemical properties of tissue therein, such as those influenced by presence and/or state of disease, such as cancer. For example, certain radiopharmaceuticals, following administration to a patient, accumulate in regions of abnormal osteogenesis associated with malignant bone lesions, which are indicative of metastases. Other radiopharmaceuticals may bind to specific receptors, enzymes, and proteins in the body that are altered during evolution of disease. After administration to a patient, these molecules circulate in the blood until they find their intended target. The bound radiopharmaceutical remains at the site of disease, while the rest of the agent clears from the body.

Nuclear medicine imaging techniques capture images by detecting radiation emitted from the radioactive portion of the radiopharmaceutical. The accumulated radiopharmaceutical serves as a beacon so that an image may be obtained depicting the disease location and concentration using commonly available nuclear medicine modalities. Examples of nuclear medicine imaging modalities include bone scan imaging (also referred to as scintigraphy), single-photon emission computerized tomography (SPECT), and positron emission tomography (PET). Bone scan, SPECT, and PET imaging systems are found in most hospitals throughout the world. Choice of a particular imaging modality depends on and/or dictates the particular radiopharmaceutical used. For example, technetium 99m ($^{99m}Tc$) labeled compounds are compatible with bone scan imaging and SPECT imaging, while PET imaging often uses fluorinated compounds labeled with 18F. The compound $^{99m}Tc$ methylenediphosphonate ($^{99m}Tc$ MDP) is a popular radiopharmaceutical used for bone scan imaging in order to detect metastatic cancer. Radiolabeled prostate-specific membrane antigen (PSMA) targeting compounds such as $^{99m}Tc$ labeled 1404 and PyL™ (also referred to as [18F]DCFPyL) can be used with SPECT and PET imaging, respectively, and offer the potential for highly specific prostate cancer detection.

Accordingly, nuclear medicine imaging is a valuable technique for providing physicians with information that can be used to determine the presence and the extent of disease in a patient. The physician can use this information to provide a recommended course of treatment to the patient and to track the progression of disease.

For example, an oncologist may use nuclear medicine images from a study of a patient as input in her assessment of whether the patient has a particular disease, e.g., prostate cancer, what stage of the disease is evident, what the recommended course of treatment (if any) would be, whether surgical intervention is indicated, and likely prognosis. The oncologist may use a radiologist report in this assessment. A radiologist report is a technical evaluation of the nuclear medicine images prepared by a radiologist for a physician who requested the imaging study and includes, for example, the type of study performed, the clinical history, a comparison between images, the technique used to perform the study, the radiologist's observations and findings, as well as overall impressions and recommendations the radiologist may have based on the imaging study results. A signed radiologist report is sent to the physician ordering the study for the physician's review, followed by a discussion between the physician and patient about the results and recommendations for treatment.

Thus, the process involves having a radiologist perform an imaging study on the patient, analyzing the images obtained, creating a radiologist report, forwarding the report to the requesting physician, having the physician formulate an assessment and treatment recommendation, and having the physician communicate the results, recommendations, and risks to the patient. The process may also involve repeating the imaging study due to inconclusive results, or ordering further tests based on initial results. If an imaging study shows that the patient has a particular disease or condition (e.g., cancer), the physician discusses various treatment options, including surgery, as well as risks of doing nothing or adopting a watchful waiting or active surveillance approach, rather than having surgery.

Accordingly, the process of reviewing and analyzing multiple patient images, over time, plays a critical role in the diagnosis and treatment of cancer. There is a significant need for improved tools that facilitate and improve accuracy of image review and analysis for cancer diagnosis and treatment. Improving the toolkit utilized by physicians, radiologists, and other healthcare professionals in this manner provides for significant improvements in standard of care and patient experience.

SUMMARY OF THE INVENTION

Presented herein are systems and methods that provide for improved detection and characterization of lesions within a subject via automated analysis of nuclear medicine images, such as positron emission tomography (PET) and single photon emission computed tomography (SPECT) images. In particular, in certain embodiments, the approaches described herein leverage artificial intelligence (AI) techniques to detect regions of 3D nuclear medicine images that represent potential cancerous lesions in the subject. In certain embodiments, these regions correspond to localized regions of elevated intensity with relative to their surroundings—hotspots—due to increased uptake of radiopharmaceutical within lesions. The systems and methods described herein may use one or more machine learning modules not only to detect presence and locations of such hotspots within an image, but also to segment the region corresponding to the hotspot and/or classify hotspots based on the likelihood that they indeed correspond to a true, underlying cancerous lesion. These AI-based lesion detection, segmentation, and classification approaches can provide a basis for further characterization of lesions, overall tumor burden, and estimation of disease severity and risk.

For example, once image hotspots representing lesions are detected, segmented, and classified, lesion index values can be computed to provide a measure of radiopharmaceutical uptake within and/or a size (e.g., volume) of the underlying lesion. The computed lesion index values can, in turn, be aggregated to provide an overall estimate of tumor burden, disease severity, metastasis risk, and the like, for the subject. In certain embodiments, lesion index values are computed by comparing measures of intensities within segmented hotspot volumes to intensities of specific reference organs, such as liver and aorta portions. Using reference organs in this manner allows for lesion index values to be measured on a normalized scale that can be compared between images of different subjects. In certain embodiments, the approaches described herein include techniques for suppressing intensity bleed from multiple image regions that correspond to organs and tissue regions in which radiopharmaceutical accumulates at high-levels under normal circumstances, such as a kidney, liver, and a bladder (e.g., urinary bladder). Intensities in regions of nuclear medicine images corresponding to these organs are typically high even for normal, healthy subjects, and not necessarily indicative of cancer. Moreover, high radiopharmaceutical accumulation in these organs results in high levels of emitted radiation. The increased emitted radiation can scatter, resulting not just in high intensities within regions of nuclear medicine images corresponding to the organs themselves, but also at nearby outside voxels. This intensity bleed, into regions of an image outside and around regions corresponding to an organ associated with high uptake, can hinder detection of nearby lesions and cause inaccuracies in measuring uptake therein. Accordingly, correcting such intensity bleed effects improves accuracy of lesion detection and quantification.

In certain embodiments, the AI-based lesion detection technique described herein augment the functional information obtained from nuclear medicine images with anatomical information obtained from anatomical images, such as x-ray computed tomography (CT) images. For example, machine learning modules utilized in the approaches described herein may receive multiple channels of input, including a first channel corresponding to a portion of a functional, nuclear medicine, image (e.g., a PET image; e.g., a SPECT image), as well as additional channels corresponding to a portion of a co-aligned anatomical (e.g., CT) image and/or anatomical information derived therefrom. Adding anatomical context in this manner may improve accuracy of lesion detection approaches. Anatomical information may also be incorporated into lesion classification approaches applied following detection. For example, in addition to computing lesion index values based on intensities of detected hotspots, hotspots may also be assigned an anatomical label based on their location. For example, detected hotspots may be automatically assigned an label (e.g., an alphanumeric label) based on whether their locations correspond to locations within a prostate, pelvic lymph node, non-pelvic lymph node, bone, or a soft-tissue region outside the prostate and lymph nodes.

In certain embodiments, detected hotspots and associated information, such as computed lesion index values and anatomical labeling, are displayed with an interactive graphical user interface (GUI) so as to allow for review by a medical professional, such as a physician, radiologist, technician, etc. Medical professionals may thus use the GUI to review and confirm accuracy of detected hotspots, as well as corresponding index values and/or anatomical labeling. In certain embodiments, the GUI may also allow users to identify, and segment (e.g., manually) additional hotspots within medical images, thereby allowing a medical professional to identify additional potential lesions that he/she believes the automated detection process may have missed. Once identified, lesion index values and/or anatomical labeling may also be determined for these manually identified and segmented lesions. Once a user is satisfied with the set of detected hotspots and information computed therefrom, they may confirm their approval and generate a final, signed, report that can, for example, be reviewed and used to discuss outcomes and diagnosis with a patient, and assess prognosis and treatment options.

In this manner, the approaches described herein provide AI-based tools for lesion detection and analysis that can improve accuracy of and streamline assessment of disease (e.g., cancer) state and progression in a subject. This facilitates diagnosis, prognosis, and assessment of response to treatment, thereby improving patient outcomes.

In one aspect, the invention is directed to a method for automatically processing 3D images of a subject to identify and/or characterize (e.g., grade) cancerous lesions within the subject, the method comprising: (a) receiving (e.g., and/or accessing), by a processor of a computing device, a 3D functional image of the subject obtained using a functional imaging modality [e.g., positron emission tomography (PET); e.g., single-photon emission computed tomography (SPECT)][e.g., wherein the 3D functional image comprises a plurality of voxels, each representing a particular physical volume within the subject and having an intensity value (e.g., standard uptake value (SUV)) that represents detected radiation emitted from the particular physical volume, wherein at least a portion of the plurality of voxels of the 3D functional image represent physical volumes within the target tissue region]; (b) automatically detecting, by the processor, using a machine learning module [e.g., a pretrained machine learning module (e.g., having pre-determined (e.g., and fixed) parameters having been determined via a training procedure)], one or more hotspots within the 3D functional image, each hotspot corresponding to a local region of elevated intensity with respect to its surrounding and representing (e.g., indicative of) a potential cancerous lesion within the subject, thereby creating one or both of (i) and (ii) as follows: (i) a hotspot list [e.g., a list of coordinates (e.g., image coordinates; e.g., physical space coordinates); e.g., a mask identifying voxels of the 3D functional image corresponding to a location (e.g., a center of mass) of a detected hotspot] identifying, for each hotspot, a location of the hotspot, and (ii) a 3D hotspot map, identifying, for each hotspot, a corresponding 3D hotspot volume within the 3D functional image {e.g., wherein, the 3D hotspot map is a segmentation map (e.g., comprising one or more segmentation masks) identifying, for each hotspot, voxels within the 3D functional image corresponding to the 3D hotspot volume of each hotspot [e.g., wherein the 3D hotspot map is obtained via artificial intelligence-based segmentation of the functional image (e.g., using a machine-learning module that receives, as input, at least the 3D functional image and generates the 3D hotspot map as output, thereby segmenting hotspots)]; e.g., wherein the 3D hotspot map delineates, for each hotspot, a 3D boundary (e.g., an irregular boundary) of the hotspot (e.g., the 3D boundary enclosing the 3D hotspot volume, e.g., and distinguishing voxels of the 3D functional image that make up the 3D hotspot volume from other voxels of the 3D functional image)}; and (c) storing and/or providing, for display and/or further processing, the hotspot list and/or the 3D hotspot map.

In certain embodiments, the machine learning module receives, as input, at least a portion of the 3D functional image and automatically detects the one or more hotspots based at least in part on intensities of voxels of the received portion of the 3D functional image. In certain embodiments, the machine learning module receives, as input, a 3D segmentation map that identifies one or more volumes of interest (VOIs) within the 3D functional image, each VOI corresponding to a particular target tissue region and/or a particular anatomical region within the subject [e.g., a soft-tissue region (e.g., a prostate, a lymph node, a lung, a breast); e.g., one or more particular bones; e.g., an overall skeletal region].

In certain embodiments, the method comprises receiving (e.g., and/or accessing), by the processor, a 3D anatomical image of the subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject, and the machine learning module receives at least two channels of input, said input channels comprising a first input channel corresponding to at least a portion of the 3D anatomical image and a second input channel corresponding to at least a portion of the 3D functional image [e.g., wherein the machine learning module receives a PET image and a CT image as separate channels (e.g., separate channels representative of the same volume) (e.g., analogous to receipt by a machine learning module of two color channels (RGB) of a photographic color image)].

In certain embodiments, the machine learning module receives, as input, a 3D segmentation map that identifies, within the 3D functional image and/or the 3D anatomical image, one or more volumes of interest (VOIs), each VOI corresponding to a particular target tissue region and/or a particular anatomical region. In certain embodiments, the method comprises automatically segmenting, by the processor, the 3D anatomical image, thereby creating the 3D segmentation map.

In certain embodiments, the machine learning module is a region-specific machine learning module that receives, as input, a specific portion of the 3D functional image corresponding to one or more specific tissue regions and/or anatomical regions of the subject.

In certain embodiments, the machine learning module generates, as output, the hotspot list [e.g., wherein the machine learning module implements a machine learning algorithm (e.g., an artificial neural network (ANN)) trained to determine, based on intensities of voxels of at least a portion of the 3D functional image, one or more locations (e.g., 3D coordinates), each corresponding to a location of one of the one or more hotspots].

In certain embodiments, the machine learning module generates, as output, the 3D hotspot map [e.g., wherein the machine learning module implements a machine learning algorithm (e.g., an artificial neural network (ANN)) trained to segment the 3D functional image (e.g., based at least in part on intensities of voxels of the 3D functional image) to identify the 3D hotspot volumes of the 3D hotspot map (e.g., the 3D hotspot map delineating, for each hotspot, a 3D boundary (e.g., an irregular boundary) of the hotspot, thereby identifying the 3D hotspot volumes (e.g., enclosed by the 3D hotspot boundaries)); e.g., wherein the machine learning module implements a machine learning algorithm trained to determine, for each voxel of at least a portion of the 3D functional image, a hotspot likelihood value representing a likelihood that the voxel corresponds to a hotspot (e.g., and step (b) comprises performing one or more subsequent post-processing steps, such as thresholding, to identify the 3D hotspot volumes of the 3D hotspot map using the hotspot likelihood values (e.g., the 3D hotspot map delineating, for each hotspot, a 3D boundary (e.g., an irregular boundary) of the hotspot, thereby identifying the 3D hotspot volumes (e.g., enclosed by the 3D hotspot boundaries)))].

In certain embodiments, the method comprises: (d) determining, by the processor, for each hotspot of at least a portion of the hotspots, a lesion likelihood classification corresponding to a likelihood of the hotspot representing a lesion within the subject [e.g., a binary classification indicative of whether the hotspot is a true lesion or not; e.g., a likelihood value on a scale (e.g., a floating point value ranging from zero to one) representing a likelihood of the hotspot representing a true lesion].

In certain embodiments, step (d) comprises using a second machine learning module to determine, for each hotspot of the portion, the lesion likelihood classification [e.g., wherein the machine learning module implements a machine learning algorithm trained to detect hotspots (e.g., to generate, as output, the hotspot list and/or the 3D hotspot map) and to determine, for each hotspot, the lesion likelihood classification for the hotpot]. In certain embodiments, step (d) comprises using a second machine learning module (e.g., a hotspot classification module) to determine the lesion likelihood classification for each hotspot [e.g., based at least in part on one or more members selected from the group consisting of: intensities of the 3D functional image, the hotspot list, the 3D hotspot map, intensities of a 3D anatomical image, and a 3D segmentation map; e.g., wherein the second machine learning module receives one or more channels of input corresponding to one or more members selected from the group consisting of intensities of the 3D functional image, the hotspot list, the 3D hotspot map, intensities of a 3D anatomical image, and a 3D segmentation map].

In certain embodiments, the method comprises determining, by the processor, for each hotspot, a set of one or more hotspot features and using the set of the one or more hotspot features as input to the second machine learning module.

In certain embodiments, the method comprises: (e) selecting, by the processor, based at least in part on the lesion likelihood classifications for the hotspots, a subset of the one or more hotspots corresponding to hotspots having a high likelihood of corresponding to cancerous lesions (e.g., for inclusion in a report; e.g., for use in computing one or more risk index values for the subject).

In certain embodiments, the method comprises: (f) [e.g., prior to step (b)] adjusting intensities of voxels of the 3D functional image, by the processor, to correct for intensity bleed (e.g., cross-talk) from one or more high-intensity volumes of the 3D functional image, each of the one or more high-intensity volumes corresponding to a high-uptake tissue region within the subject associated with high radiopharmaceutical uptake under normal circumstances (e.g., not necessarily indicative of cancer). In certain embodiments, step (f) comprises correcting for intensity bleed from a plurality of high-intensity volumes one at a time, in a sequential fashion [e.g., first adjusting intensities of voxels of the 3D functional image to correct for intensity bleed from a first high-intensity volume to generate a first corrected image, then adjusting intensities of voxels of the first corrected image to correct for intensity bleed from a second high-intensity volume, and so on]. In certain embodiments, the one or more high-intensity volumes correspond to one or more high-uptake tissue regions selected from the group consisting of a kidney, a liver, and a bladder (e.g., a urinary bladder).

In certain embodiments, the method comprises: (g) determining, by the processor, for each of at least a portion of the one or more hotspots, a corresponding lesion index indicative of a level of radiopharmaceutical uptake within and/or size (e.g., volume) of an underlying lesion to which the hotspot corresponds. In certain embodiments, step (g) comprises comparing an intensity (intensities) (e.g., corresponding to standard uptake values (SUVs)) of one or more voxels associated with the hotspot (e.g., at and/or about a location of the hotspot; e.g., within a volume of the hotspot) with one or more reference values, each reference value associated with a particular reference tissue region (e.g., a liver; e.g., an aorta portion) within the subject and determined based on intensities (e.g., SUV values) of a reference volume corresponding to the reference tissue region [e.g., as an average (e.g., a robust average, such as a mean of values in an interquartile range)]. In certain embodiments, the one or more reference values comprise one or more members selected from the group consisting of an aorta reference value associated with an aorta portion of the subject and a liver reference value associated with a liver of the subject.

In certain embodiments, for at least one particular reference value associated with a particular reference tissue region, determining the particular reference value comprises fitting intensities of voxels [e.g., fitting an distribution of intensities of voxels (e.g., fitting a histogram of voxel intensities)] within a particular reference volume corresponding to the particular reference tissue region to a multi-component mixture model (e.g., a two-component Gaussian model)[e.g., and identifying one or more minor peaks in a distribution of voxel intensities, said minor peaks corresponding to voxels associated with anomalous uptake, and excluding those voxels from the reference value determination (e.g., thereby accounting for effects of abnormally low radiopharmaceutical uptake in certain portions of reference tissue regions, such as portions of the liver)].

In certain embodiments, the method comprises using the determined lesion index values compute (e.g., automatically, by the processor) an overall risk index for the subject, indicative of a caner status and/or risk for the subject.

In certain embodiments, the method comprises determining, by the processor (e.g., automatically), for each hotspot, an anatomical classification corresponding to a particular anatomical region and/or group of anatomical regions within the subject in which the potential cancerous lesion that the hotspot represents is determined [e.g., by the processor (e.g., based on a received and/or determined 3D segmentation map)] to be located [e.g., within a prostate, a pelvic lymph node, a non-pelvic lymph node, a bone (e.g., a bone metastatic region), and a soft tissue region not situated in prostate or lymph node].

In certain embodiments, the method comprise: (h) causing, by the processor, for display within a graphical user interface (GUI), graphical representation of at least a portion of the one or more hotspots for review by a user. In certain embodiments, the method comprises: (i) receiving, by the processor, via the GUI, a user selection of a subset of the one or more hotspots confirmed via user review as likely to represent underlying cancerous lesions within the subject.

In certain embodiments, the 3D functional image comprises a PET or SPECT image obtained following administration of an agent (e.g., a radiopharmaceutical; e.g., an imaging agent) to the subject. In certain embodiments, the agent comprises a PSMA binding agent. In certain embodiments, the agent comprises [18F]DCFPyL. In certain embodiments, the agent comprises $^{99m}$Tc.

In certain embodiments, the machine learning module implements a neural network [e.g., an artificial neural network (ANN); e.g., a convolutional neural network (CNN)].

In certain embodiments, the processor is a processor of a cloud-based system.

In another aspect, the invention is directed to a method for automatically processing 3D images of a subject to identify and/or characterize (e.g., grade) cancerous lesions within the subject, the method comprising: (a) receiving (e.g., and/or accessing), by a processor of a computing device, a 3D functional image of the subject obtained using a functional imaging modality [e.g., positron emission tomography (PET); e.g., single-photon emission computed tomography (SPECT)][e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (b) receiving (e.g., and/or accessing), by the processor, a 3D anatomical image of the subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject; (c) automatically detecting, by the processor, using a machine learning module, one or more hotspots within the 3D functional image, each hotspot corresponding to a local region of elevated intensity with respect to its surrounding and representing (e.g., indicative of) a potential cancerous lesion within the subject, thereby creating one or both of (i) and (ii) as follows: (i) a hotspot list identifying, for each hotspot, a location of the hotspot, and (ii) a 3D hotspot map, identifying, for each hotspot, a corresponding 3D hotspot volume within the 3D functional image {e.g., wherein, the 3D hotspot map is a segmentation map (e.g., comprising one or more segmentation masks) identifying, for each hotspot, voxels within the 3D functional image corresponding to the 3D hotspot volume of each hotspot [e.g., wherein the 3D hotspot map is obtained via artificial intelligence-based segmentation of the functional image (e.g., using a machine-learning module that receives, as input, at least the 3D functional image and generates the 3D hotspot map as output, thereby segmenting hotspots)]; e.g., wherein the 3D hotspot map delineates, for each hotspot, a 3D boundary (e.g., an irregular boundary) of the hotspot (e.g., the 3D boundary enclosing the 3D hotspot volume, e.g., and distinguishing voxels of the 3D functional image that make up the 3D hotspot volume from other voxels of the 3D functional image)}, wherein the machine learning module receives at least two channels of input, said input channels comprising a first input channel corresponding to at least a portion of the 3D anatomical image and a second input channel corresponding to at least a portion of the 3D functional image [e.g., wherein the machine learning module receives a PET image and a CT image as separate channels (e.g., separate channels representative of the same volume) (e.g., analogous to receipt by a machine learning module of two color channels (RGB) of a photographic color image)] and/or anatomical information derived therefrom [e.g., a 3D segmentation map that identifies, within the 3D functional image, one or more volumes of interest (VOIs), each VOI corresponding to a particular target tissue region and/or a particular anatomical region]; and (d) storing and/or providing for display and/or further processing, the hotspot list and/or the 3D hotspot map.

In another aspect, the invention is directed to a method for automatically processing 3D images of a subject to identify and/or characterize (e.g., grade) cancerous lesions within the subject, the method comprising: (a) receiving (e.g., and/or accessing), by a processor of a computing device, a 3D functional image of the subject obtained using a functional imaging modality [e.g., positron emission tomography (PET); e.g., single-photon emission computed tomography (SPECT)][e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (b) automatically detecting, by the processor, using a first machine learning module, one or more hotspots within the 3D functional image, each hotspot corresponding to a local region of elevated intensity with respect to its surrounding and representing (e.g., indicative of) a potential cancerous lesion within the subject, thereby creating a hotspot list identifying, for each hotspot, a location of the hotspot [e.g., wherein the machine learning module implements a machine learning algorithm (e.g., an artificial neural network (ANN)) trained to determine, based on intensities of voxels of at least a portion of the 3D functional image, one or more locations (e.g., 3D coordinates), each corresponding to a location of one of the one or more hotspots]; (c) automatically determining, by the processor, using a second machine learning module and the hotspot list, for each of the one or more hotspots, a corresponding 3D hotspot volume within the 3D functional image, thereby creating a 3D hotspot map [e.g., wherein the second machine learning module implements a machine learning algorithm (e.g., an artificial neural network (ANN)) trained to segment the 3D functional image based at least in part on the hotspot list along with intensities of voxels of the 3D functional image to identify the 3D hotspot volumes of the 3D hotspot map; e.g., wherein the machine learning module implements a machine learning algorithm trained to determine, for each voxel of at least a portion of the 3D functional image, a hotspot likelihood value representing a likelihood that the voxel corresponds to a hotspot (e.g., and step (b) comprises performing one or more subsequent post-processing steps, such as thresholding, to identify the 3D hotspot volumes of the 3D hotspot map using the hotspot likelihood values][e.g., wherein, the 3D hotspot map is a segmentation map (e.g., comprising one or more segmentation masks) generated using (e.g., based on and/or corresponding to output from) the second machine learning module, the 3D hotspot map identifying, for each hotspot, voxels within the 3D functional image corresponding to the 3D hotspot volume of each hotspot); e.g., wherein the 3D hotspot map delineates, for each hotspot, a 3D boundary (e.g., an irregular boundary) of the hotspot (e.g., the 3D boundary enclosing the 3D hotspot volume, e.g., and distinguishing voxels of the 3D functional image that make up the 3D hotspot volume from other voxels of the 3D functional image)]; and (d) storing and/or providing for display and/or further processing, the hotspot list and/or the 3D hotspot map.

In certain embodiments, the method comprises: (e) determining, by the processor, for each hotspot of at least a portion of the hotspots, a lesion likelihood classification corresponding to a likelihood of the hotspot representing a lesion within the subject. In certain embodiments, step (e) comprises using a third machine learning module (e.g., a hotspot classification module) to determine the lesion likelihood classification for each hotspot [e.g., based at least in part on one or more members selected from the group consisting of intensities of the 3D functional image, the hotspot list, the 3D hotspot map, intensities of a 3D anatomical image, and a 3D segmentation map; e.g., wherein the third machine learning module receives one or more channels of input corresponding to one or more members selected from the group consisting of intensities of the 3D functional image, the hotspot list, the 3D hotspot map, intensities of a 3D anatomical image, and a 3D segmentation map].

In certain embodiments, the method comprises: (f) selecting, by the processor, based at least in part on the lesion likelihood classifications for the hotspots, a subset of the one or more hotspots corresponding to hotspots having a high likelihood of corresponding to cancerous lesions (e.g., for inclusion in a report; e.g., for use in computing one or more risk index values for the subject).

In another aspect, the invention is directed to a method of measuring intensity values within a reference volume corresponding to a reference tissue region (e.g., a liver volume associated with a liver of a subject) so as to avoid impact from tissue regions associated with low (e.g., abnormally low) radiopharmaceutical uptake (e.g., due to tumors without tracer uptake), the method comprising: (a) receiving (e.g., and/or accessing), by a processor of a computing device, the 3D functional image of a subject, said 3D functional image obtained using a functional imaging modality [e.g., positron emission tomography (PET); e.g., single-photon emission computed tomography (SPECT)] [e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (b) identifying, by the processor, the reference volume within the 3D functional image; (c) fitting, by the processor, a multi-component mixture model (e.g., a two-component Gaussian mixture model) to intensities of voxels within the reference volume [e.g., fitting the multi-component mixture model to a distribution (e.g., a histogram) of intensities of voxels within the reference volume]; (d) identifying, by the processor, a major mode of the multi-component model; (e) determining, by the processor, a measure of (e.g., a mean, a maximum, a mode, a median, etc.) intensities corresponding to the major mode, thereby determining a reference intensity value corresponding to a measure of intensity of voxels that are (i) within the reference tissue volume and (ii) associated with the major mode (e.g., and excluding, from the reference value calculation, voxels having intensities associated with minor modes) (e.g., thereby avoiding impact from tissue regions associated with low radiopharmaceutical uptake); (f) detecting, by the processor, within the functional image, one or more hotspots corresponding potential cancerous lesions; and (g) determining, by the processes or, for each hotspot of at least a portion of the detected hotspots, a lesion index value, using at least the reference intensity value [e.g., the lesion index value based on (i) a measure of intensities of voxels corresponding to the detected hotspot and (ii) the reference intensity value].

In another aspect, the invention is directed to a method of correcting for intensity bleed (e.g., cross-talk) from due to high-uptake tissue regions within the subject that are associated with high radiopharmaceutical uptake under normal circumstances (e.g., and not necessarily indicative of cancer), the method comprising: (a) receiving (e.g., and/or accessing), by a processor of a computing device, the 3D functional image of the subject, said 3D functional image obtained using a functional imaging modality [e.g., positron emission tomography (PET); e.g., single-photon emission computed tomography (SPECT)][e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (b) identifying, by the processor, a high-intensity volume within the 3D functional image, said high intensity volume corresponding to a particular high-uptake tissue region (e.g., a kidney; e.g., a liver; e.g., a bladder) in which high radiopharmaceutical uptake occurs under normal circumstances; (c) identifying, by the processor, based on the identified high-intensity volume, a suppression volume within the 3D functional image, said suppression volume corresponding to a volume lying outside and within a predetermined decay distance from a boundary of the identified high intensity volume; (d) determining, by the processor, a background image corresponding to the 3D functional image with intensities of voxels within the high-intensity volume replaced with interpolated values determined based on intensities of voxels of the 3D functional image within the suppression volume; (e) determining, by the processor, an estimation image by subtracting intensities of voxels of the background image from intensities of voxels from the 3D functional image (e.g., performing a voxel-by-voxel subtraction); (f) determining, by the processor, a suppression map by: extrapolating intensities of voxels of the estimation image corresponding to the high-intensity volume to locations of voxels within the suppression volume to determine intensities of voxels of the suppression map corresponding to the suppression volume; and setting intensities of voxels of the suppression map corresponding to locations outside the suppression volume to zero; and (g) adjusting, by the processor, intensities of voxels of the 3D functional image based on the suppression map (e.g., by subtracting intensities of voxels of the suppression map from intensities of voxels of the 3D functional image), thereby correcting for intensity bleed from the high-intensity volume.

In certain embodiments, the method comprises performing steps (b) through (g) for each of a plurality of high-intensity volumes in a sequential manner, thereby correcting for intensity bleed from each of the plurality of high-intensity volumes.

In certain embodiments, the plurality of high-intensity volumes comprise one or more members selected from the group consisting of a kidney, a liver, and a bladder (e.g., a urinary bladder).

In another aspect, the invention is directed to a method for automatically processing 3D images of a subject to identify and/or characterize (e.g., grade) cancerous lesions within the subject, the method comprising: (a) receiving (e.g., and/or accessing), by a processor of a computing device, a 3D functional image of the subject obtained using a functional imaging modality [e.g., positron emission tomography (PET); e.g., single-photon emission computed tomography (SPECT)][e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (b) automatically detecting, by the processor, one or more hotspots within the 3D functional image, each hotspot corresponding to a local region of elevated intensity with respect to its surrounding and representing (e.g., indicative of) a potential cancerous lesion within the subject; (c) causing, by the processor, rendering of a graphical representation of the one or more hotspots for display within an interactive graphical user interface (GUI) (e.g., a quality control and reporting GUI); (d) receiving, by the processor, via the interactive GUI, a user selection of a final hotspot set comprising at least a portion (e.g., up to all) of the one or more automatically detected hotspots (e.g., for inclusion in a report); and (e) storing and/or providing for display and/or further processing, the final hotspot set.

In certain embodiments, the method comprises: (f) receiving, by the processor, via the GUI, a user selection of one or more additional, user-identified, hotspots for inclusion in the final hotspot set; and (g) updating, by the processor, the final hotspot set to include the one or more additional user-identified hotspots.

In certain embodiments, step (b) comprises using one or more machine learning modules.

In another aspect, the invention is directed to a method for automatically processing 3D images of a subject to identify and characterize (e.g., grade) cancerous lesions within the subject, the method comprising: (a) receiving (e.g., and/or accessing), by a processor of a computing device, a 3D functional image of the subject obtained using a functional imaging modality [e.g., positron emission tomography (PET); e.g., single-photon emission computed tomography (SPECT)][e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (b) automatically detecting, by the processor, one or more hotspots within the 3D functional image, each hotspot corresponding to a local region of elevated intensity with respect to its surrounding and representing (e.g., indicative of) a potential cancerous lesion within the subject; (c) automatically determining, by the processor, for each of at least a portion of the one or more hotspots, an anatomical classification corresponding to a particular anatomical region and/or group of anatomical regions within the subject in which the potential cancerous lesion that the hotspot represents is determined [e.g., by the processor (e.g., based on a received and/or determined 3D segmentation map)] to be located [e.g., within a prostate, a pelvic lymph node, a non-pelvic lymph node, a bone (e.g., a bone metastatic region), and a soft tissue region not situated in prostate or lymph node]; and (d) storing and/or providing for display and/or further processing, an identification of the one or more hotspots along with, for each hotspot, the anatomical classification corresponding to the hotspot.

In certain embodiments, step (b) comprises using one or more machine learning modules.

In another aspect, the invention is directed to a system for automatically processing 3D images of a subject to identify and/or characterize (e.g., grade) cancerous lesions within the subject, the system comprising: a processor of a computing device; and a memory having instructions stored thereon, wherein the instructions, when executed by the processor, cause the processor to: (a) receive (e.g., and/or access) a 3D functional image of the subject obtained using a functional imaging modality [e.g., positron emission tomography (PET); e.g., single-photon emission computed tomography (SPECT)][e.g., wherein the 3D functional image comprises a plurality of voxels, each representing a particular physical volume within the subject and having an intensity value (e.g., standard uptake value (SUV)) that represents detected radiation emitted from the particular physical volume, wherein at least a portion of the plurality of voxels of the 3D functional image represent physical volumes within the target tissue region]; (b) automatically detect, using a machine learning module [e.g., a pre-trained machine learning module (e.g., having pre-determined (e.g., and fixed) parameters having been determined via a training procedure)], one or more hotspots within the 3D functional image, each hotspot corresponding to a local region of elevated intensity with respect to its surrounding and representing (e.g., indicative of) a potential cancerous lesion within the subject, thereby creating one or both of (i) and (ii) as follows: (i) a hotspot list [e.g., a list of coordinates (e.g., image coordinates; e.g., physical space coordinates); e.g., a mask identifying voxels of the 3D functional image, each voxel corresponding to a location (e.g., a center of mass) of a detected hotspot] identifying, for each hotspot, a location of the hotspot, and (ii) a 3D hotspot map, identifying, for each hotspot, a corresponding 3D hotspot volume within the 3D functional image {e.g., wherein, the 3D hotspot map is a segmentation map (e.g., comprising one or more segmentation masks) identifying, for each hotspot, voxels within the 3D functional image corresponding to the 3D hotspot volume of each hotspot [e.g., wherein the 3D hotspot map is obtained via artificial intelligence-based segmentation of the functional image (e.g., using a machine-learning module that receives, as input, at least the 3D functional image and generates the 3D hotspot map as output, thereby segmenting hotspots)]; e.g., wherein the 3D hotspot map delineates, for each hotspot, a 3D boundary (e.g., an irregular boundary) of the hotspot (e.g., the 3D boundary enclosing the 3D hotspot volume, e.g., and distinguishing voxels of the 3D functional image that make up the 3D hotspot volume from other voxels of the 3D functional image)}; and (c) store and/or provide, for display and/or further processing, the hotspot list and/or the 3D hotspot map.

In certain embodiments, the machine learning module receives, as input, at least a portion of the 3D functional image and automatically detects the one or more hotspots based at least in part on intensities of voxels of the received portion of the 3D functional image.

In certain embodiments, the machine learning module receives, as input, a 3D segmentation map that identifies one or more volumes of interest (VOIs) within the 3D functional image, each VOI corresponding to a particular target tissue region and/or a particular anatomical region within the subject [e.g., a soft-tissue region (e.g., a prostate, a lymph node, a lung, a breast); e.g., one or more particular bones; e.g., an overall skeletal region].

In certain embodiments, the instructions cause the processor to: receive (e.g., and/or access) a 3D anatomical image of the subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject, and the machine learning module receives at least two channels of input, said input channels comprising a first input channel corresponding to at least a portion of the 3D anatomical image and a second input channel corresponding to at least a portion of the 3D functional image [e.g., wherein the machine learning module receives a PET image and a CT image as separate channels (e.g., separate channels representative of the same volume) (e.g., analogous to receipt by a machine learning module of two color channels (RGB) of a photographic color image)].

In certain embodiments, the machine learning module receives, as input, a 3D segmentation map that identifies, within the 3D functional image and/or the 3D anatomical image, one or more volumes of interest (VOIs), each VOI corresponding to a particular target tissue region and/or a particular anatomical region.

In certain embodiments, the instructions cause the processor to automatically segment the 3D anatomical image, thereby creating the 3D segmentation map.

In certain embodiments, the machine learning module is a region-specific machine learning module that receives, as input, a specific portion of the 3D functional image corresponding to one or more specific tissue regions and/or anatomical regions of the subject.

In certain embodiments, the machine learning module generates, as output, the hotspot list [e.g., wherein the machine learning module implements a machine learning algorithm (e.g., an artificial neural network (ANN)) trained to determine, based on intensities of voxels of at least a portion of the 3D functional image, one or more locations (e.g., 3D coordinates), each corresponding to a location of one of the one or more hotspots].

In certain embodiments, the machine learning module generates, as output, the 3D hotspot map [e.g., wherein the machine learning module implements a machine learning algorithm (e.g., an artificial neural network (ANN)) trained to segment the 3D functional image (e.g., based at least in part on intensities of voxels of the 3D functional image) to identify the 3D hotspot volumes of the 3D hotspot map (e.g., the 3D hotspot map delineating, for each hotspot, a 3D boundary (e.g., an irregular boundary) of the hotspot, thereby identifying the 3D hotspot volumes (e.g., enclosed by the 3D hotspot boundaries)); e.g., wherein the machine learning module implements a machine learning algorithm trained to determine, for each voxel of at least a portion of the 3D functional image, a hotspot likelihood value representing a likelihood that the voxel corresponds to a hotspot (e.g., and step (b) comprises performing one or more subsequent post-processing steps, such as thresholding, to identify the 3D hotspot volumes of the 3D hotspot map using the hotspot likelihood values (e.g., the 3D hotspot map delineating, for each hotspot, a 3D boundary (e.g., an irregular boundary) of the hotspot, thereby identifying the 3D hotspot volumes (e.g., enclosed by the 3D hotspot boundaries)))].

In certain embodiments, the instructions cause the processor to: (d) determine, for each hotspot of at least a portion of the hotspots, a lesion likelihood classification corresponding to a likelihood of the hotspot representing a lesion within the subject [e.g., a binary classification indicative of whether the hotspot is a true lesion or not; e.g., a likelihood value on a scale (e.g., a floating point value ranging from zero to one) representing a likelihood of the hotspot representing a true lesion].

In certain embodiments, at step (d) the instructions cause the processor to use the machine learning module to determine, for each hotspot of the portion, the lesion likelihood classification [e.g., wherein the machine learning module implements a machine learning algorithm trained to detect hotspots (e.g., to generate, as output, the hotspot list and/or the 3D hotspot map) and to determine, for each hotspot, the lesion likelihood classification for the hotpot].

In certain embodiments, at step (d) the instructions cause the processor to use a second machine learning module (e.g., a hotspot classification module) to determine the lesion likelihood classification for each hotspot [e.g., based at least in part on one or more members selected from the group consisting of intensities of the 3D functional image, the hotspot list, the 3D hotspot map, intensities of a 3D anatomical image, and a 3D segmentation map; e.g., wherein the second machine learning module receives one or more channels of input corresponding to one or more members selected from the group consisting of: intensities of the 3D functional image, the hotspot list, the 3D hotspot map, intensities of a 3D anatomical image, and a 3D segmentation map].

In certain embodiments, the instructions cause the processor to determine, for each hotspot, a set of one or more hotspot features and using the set of the one or more hotspot features as input to the second machine learning module.

In certain embodiments, 55 to 58, wherein the instructions cause the processor to: (e) select, based at least in part on the lesion likelihood classifications for the hotspots, a subset of the one or more hotspots corresponding to hotspots having a high likelihood of corresponding to cancerous lesions (e.g., for inclusion in a report; e.g., for use in computing one or more risk index values for the subject).

In certain embodiments, the instructions cause the processor to: (f) [e.g., prior to step (b)]adjust intensities of voxels of the 3D functional image, by the processor, to correct for intensity bleed (e.g., cross-talk) from one or more high-intensity volumes of the 3D functional image, each of the one or more high-intensity volumes corresponding to a high-uptake tissue region within the subject associated with high radiopharmaceutical uptake under normal circumstances (e.g., not necessarily indicative of cancer).

In certain embodiments, at step (f) the instructions cause the processor to correct for intensity bleed from a plurality of high-intensity volumes one at a time, in a sequential fashion [e.g., first adjusting intensities of voxels of the 3D functional image to correct for intensity bleed from a first high-intensity volume to generate a first corrected image, then adjusting intensities of voxels of the first corrected image to correct for intensity bleed from a second high-intensity volume, and so on].

In certain embodiments, the one or more high-intensity volumes correspond to one or more high-uptake tissue regions selected from the group consisting of a kidney, a liver, and a bladder (e.g., a urinary bladder).

In certain embodiments, the instructions cause the processor to: (g) determine, for each of at least a portion of the one or more hotspots, a corresponding lesion index indicative of a level of radiopharmaceutical uptake within and/or size (e.g., volume) of an underlying lesion to which the hotspot corresponds.

In certain embodiments, at step (g) the instructions cause the processor to compare an intensity (intensities) (e.g., corresponding to standard uptake values (SUVs)) of one or more voxels associated with the hotspot (e.g., at and/or about a location of the hotspot; e.g., within a volume of the hotspot) with one or more reference values, each reference value associated with a particular reference tissue region (e.g., a liver; e.g., an aorta portion) within the subject and determined based on intensities (e.g., SUV values) of a reference volume corresponding to the reference tissue region [e.g., as an average (e.g., a robust average, such as a mean of values in an interquartile range)].

In certain embodiments, the one or more reference values comprise one or more members selected from the group consisting of an aorta reference value associated with an aorta portion of the subject and a liver reference value associated with a liver of the subject.

In certain embodiments, for at least one particular reference value associated with a particular reference tissue region, the instructions cause the processor to determine the particular reference value by fitting intensities of voxels [e.g., by fitting an distribution of intensities of voxels (e.g., fitting a histogram of voxel intensities)] within a particular reference volume corresponding to the particular reference tissue region to a multi-component mixture model (e.g., a two-component Gaussian model)[e.g., and identifying one or more minor peaks in a distribution of voxel intensities, said minor peaks corresponding to voxels associated with anomalous uptake, and excluding, from the reference value determination, those voxels from the reference value determination (e.g., thereby accounting for effects of abnormally low radiopharmaceutical uptake in certain portions of reference tissue regions, such as portions of the liver)].

In certain embodiments, the instructions cause the processor to use the determined lesion index values compute (e.g., automatically) an overall risk index for the subject, indicative of a caner status and/or risk for the subject.

In certain embodiments, the instructions cause the processor to determine (e.g., automatically), for each hotspot, an anatomical classification corresponding to a particular anatomical region and/or group of anatomical regions within the subject in which the potential cancerous lesion that the hotspot represents is determined [e.g., by the processor (e.g., based on a received and/or determined 3D segmentation map)] to be located [e.g., within a prostate, a pelvic lymph node, a non-pelvic lymph node, a bone (e.g., a bone metastatic region), and a soft tissue region not situated in prostate or lymph node].

In certain embodiments, the instructions cause the processor to: (h) causing, for display within a graphical user interface (GUI), rendering of a graphical representation of at least a portion of the one or more hotspots for review by a user.

In certain embodiments, the instructions cause the processor to: (i) receiving, via the GUI, a user selection of a subset of the one or more hotspots confirmed via user review as likely to represent underlying cancerous lesions within the subject.

In certain embodiments, the 3D functional image comprises a PET or SPECT image obtained following administration of an agent (e.g., a radiopharmaceutical; e.g., an imaging agent) to the subject. In certain embodiments, the agent comprises a PSMA binding agent. In certain embodiments, the agent comprises [18F]DCFPyL. In certain embodiments, the agent comprises $^{99m}$Tc.

In certain embodiments, the machine learning module implements a neural network [e.g., an artificial neural network (ANN); e.g., a convolutional neural network (CNN)].

In certain embodiments, the processor is a processor of a cloud-based system.

In another aspect, the invention is directed to a system for automatically processing 3D images of a subject to identify and/or characterize (e.g., grade) cancerous lesions within the subject, the system comprising: a processor of a computing device; and a memory having instructions stored thereon, wherein the instructions, when executed by the processor, cause the processor to: (a) receive (e.g., and/or access) a 3D functional image of the subject obtained using a functional imaging modality [e.g., positron emission tomography (PET); e.g., single-photon emission computed tomography (SPECT)] [e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (b) receive (e.g., and/or access) a 3D anatomical image of the subject obtained using an anatomical imaging modality [e.g., x-ray computed tomography (CT); e.g., magnetic resonance imaging (MRI); e.g., ultra-sound], wherein the 3D anatomical image comprises a graphical representation of tissue (e.g., soft-tissue and/or bone) within the subject; (c) automatically detect, using a machine learning module, one or more hotspots within the 3D functional image, each hotspot corresponding to a local region of elevated intensity with respect to its surrounding and representing (e.g., indicative of) a potential cancerous lesion within the subject, thereby creating one or both of (i) and (ii) as follows: (i) a hotspot list identifying, for each hotspot, a location of the hotspot, and (ii) a 3D hotspot map, identifying, for each hotspot, a corresponding 3D hotspot volume within the 3D functional image {e.g., wherein, the 3D hotspot map is a segmentation map (e.g., comprising one or more segmentation masks) identifying, for each hotspot, voxels within the 3D functional image corresponding to the 3D hotspot volume of each hotspot [e.g., wherein the 3D hotspot map is obtained via artificial intelligence-based segmentation of the functional image (e.g., using a machine-learning module that receives, as input, at least the 3D functional image and generates the 3D hotspot map as output, thereby segmenting hotspots)]; e.g., wherein the 3D hotspot map delineates, for each hotspot, a 3D boundary (e.g., an irregular boundary) of the hotspot (e.g., the 3D boundary enclosing the 3D hotspot volume, e.g., and distinguishing voxels of the 3D functional image that make up the 3D hotspot volume from other voxels of the 3D functional image)}, wherein the machine learning module receives at least two channels of input, said input channels comprising a first input channel corresponding to at least a portion of the 3D anatomical image and a second input channel corresponding to at least a portion of the 3D functional image [e.g., wherein the machine learning module receives a PET image and a CT image as separate channels (e.g., separate channels representative of the same volume) (e.g., analogous to receipt by a machine learning module of two color channels (RGB) of a photographic color image)] and/or anatomical information derived therefrom [e.g., a 3D segmentation map that identifies, within the 3D functional image, one or more volumes of interest (VOIs), each VOI corresponding to a particular target tissue region and/or a particular anatomical region]; and (d) store and/or provide, for display and/or further processing, the hotspot list and/or the 3D hotspot map.

In another aspect, the invention is directed to a system for automatically processing 3D images of a subject to identify and/or characterize (e.g., grade) cancerous lesions within the subject, the system comprising: a processor of a computing device; and a memory having instructions stored thereon, wherein the instructions, when executed by the processor, cause the processor to: (a) receive (e.g., and/or access) a 3D functional image of the subject obtained using a functional imaging modality [e.g., positron emission tomography (PET); e.g., single-photon emission computed tomography (SPECT)][e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (b) automatically detect, using a first machine learning module, one or more hotspots within the 3D functional image, each hotspot corresponding to a local region of elevated intensity with respect to its surrounding and representing (e.g., indicative of) a potential cancerous lesion within the subject, thereby creating a hotspot list identifying, for each hotspot, a location of the hotspot [e.g., wherein the machine learning module implements a machine learning algorithm (e.g., an artificial neural network (ANN)) trained to determine, based on intensities of voxels of at least a portion of the 3D functional image, one or more locations (e.g., 3D coordinates), each corresponding to a location of one of the one or more hotspots]; (c) automatically determine, using a second machine learning module and the hotspot list, for each of the one or more hotspots, a corresponding 3D hotspot volume within the 3D functional image, thereby creating a 3D hotspot map [e.g., wherein the second machine learning module implements a machine learning algorithm (e.g., an artificial neural network (ANN)) trained to segment the 3D functional image based at least in part on the hotspot list along with intensities of voxels of the 3D functional image to identify the 3D hotspot volumes of the 3D hotspot map; e.g., wherein the machine learning module implements a machine learning algorithm trained to determine, for each voxel of at least a portion of the 3D functional image, a hotspot likelihood value representing a likelihood that the voxel corresponds to a hotspot (e.g., and step (b) comprises performing one or more subsequent post-processing steps, such as thresholding, to identify the 3D hotspot volumes of the 3D hotspot map using the hotspot likelihood values] [e.g., wherein, the 3D hotspot map is a segmentation map (e.g., comprising one or more segmentation masks) generated using (e.g., based on and/or corresponding to output from) the second machine learning module, the 3D hotspot map identifying, for each hotspot, voxels within the 3D functional image corresponding to the 3D hotspot volume of each hotspot); e.g., wherein the 3D hotspot map delineates, for each hotspot, a 3D boundary (e.g., an irregular boundary) of the hotspot (e.g., the 3D boundary enclosing the 3D hotspot volume, e.g., and distinguishing voxels of the 3D functional image that make up the 3D hotspot volume from other voxels of the 3D functional image)]; and (d) store and/or provide, for display and/or further processing, the hotspot list and/or the 3D hotspot map.

In certain embodiments, the instructions cause the processor to: (e) determine, for each hotspot of at least a portion of the hotspots, a lesion likelihood classification corresponding to a likelihood of the hotspot representing a lesion within the subject.

In certain embodiments, at step (e) the instructions cause the processor to use a third machine learning module (e.g., a hotspot classification module) to determine the lesion likelihood classification for each hotspot [e.g., based at least in part on one or more members selected from the group consisting of intensities of the 3D functional image, the hotspot list, the 3D hotspot map, intensities of a 3D anatomical image, and a 3D segmentation map; e.g., wherein the third machine learning module receives one or more channels of input corresponding to one or more members selected from the group consisting of intensities of the 3D functional image, the hotspot list, the 3D hotspot map, intensities of a 3D anatomical image, and a 3D segmentation map].

In certain embodiments, the instructions cause the processor to: (f) select, based at least in part on the lesion likelihood classifications for the hotspots, a subset of the one or more hotspots corresponding to hotspots having a high likelihood of corresponding to cancerous lesions (e.g., for inclusion in a report; e.g., for use in computing one or more risk index values for the subject).

In another aspect, the invention is directed to a system for measuring intensity values within a reference volume corresponding to a reference tissue region (e.g., a liver volume associated with a liver of a subject) so as to avoid impact from tissue regions associated with low (e.g., abnormally low) radiopharmaceutical uptake (e.g., due to tumors without tracer uptake), the system comprising: a processor of a computing device; and a memory having instructions stored thereon, wherein the instructions, when executed by the processor, cause the processor to: (a) receive (e.g., and/or access) a 3D functional image of a subject, said 3D functional image obtained using a functional imaging modality [e.g., positron emission tomography (PET); e.g., single-photon emission computed tomography (SPECT)] [e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (b) identify the reference volume within the 3D functional image; (c) fit a multi-component mixture model (e.g., a two-component Gaussian mixture model) to intensities of voxels within the reference volume [e.g., fitting the multi-component mixture model to a distribution (e.g., a histogram) of intensities of voxels within the reference volume]; (d) identify a major mode of the multi-component model; (e) determine a measure of (e.g., a mean, a maximum, a mode, a median, etc.) intensities corresponding to the major mode, thereby determining a reference intensity value corresponding to a measure of intensity of voxels that are (i) within the reference tissue volume and (ii) associated with the major mode, (e.g., and excluding, from the reference value calculation, voxels having intensities associated with minor modes) (e.g., thereby avoiding impact from tissue regions associated with low radiopharmaceutical uptake); (f) detect, within the 3D functional image, one or more hotspots corresponding potential cancerous lesions; and (g) determine, for each hotspot of at least a portion of the detected hotspots, a lesion index value, using at least the reference intensity value [e.g., the lesion index value based on (i) a measure of intensities of voxels corresponding to the detected hotspot and (ii) the reference intensity value]. In another aspect, the invention is directed to a system for correcting for intensity bleed (e.g., cross-talk) from due to high-uptake tissue regions within the subject that are associated with high radiopharmaceutical uptake under normal circumstances (e.g., and not necessarily indicative of cancer), the method comprising: (a) receive (e.g., and/or access) a 3D functional image of the subject, said 3D functional image obtained using a functional imaging modality [e.g., positron emission tomography (PET); e.g., single-photon emission computed tomography (SPECT)][e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (b) identify a high-intensity volume within the 3D functional image, said high intensity volume corresponding to a particular high-uptake tissue region (e.g., a kidney; e.g., a liver; e.g., a bladder) in which high radiopharmaceutical uptake occurs under normal circumstances; (c) identify, based on the identified high-intensity volume, a suppression volume within the 3D functional image, said suppression volume corresponding to a volume lying outside and within a predetermined decay distance from a boundary of the identified high intensity volume; (d) determine a background image corresponding to the 3D functional image with intensities of voxels within the high-intensity volume replaced with interpolated values determined based on intensities of voxels of the 3D functional image within the suppression volume; (e) determine an estimation image by subtracting intensities of voxels of the background image from intensities of voxels from the 3D functional image (e.g., performing a voxel-by-voxel subtraction); (f) determine a suppression map by: extrapolating intensities of voxels of the estimation image corresponding to the high-intensity volume to locations of voxels within the suppression volume to determine intensities of voxels of the suppression map corresponding to the suppression volume; and setting intensities of voxels of the suppression map corresponding to locations outside the suppression volume to zero; and (g) adjust intensities of voxels of the 3D functional image based on the suppression map (e.g., by subtracting intensities of voxels of the suppression map from intensities of voxels of the 3D functional image), thereby correcting for intensity bleed from the high-intensity volume.

In certain embodiments, the instructions cause the processor to perform steps (b) through (g) for each of a plurality of high-intensity volumes in a sequential manner, thereby correcting for intensity bleed from each of the plurality of high-intensity volumes.

In certain embodiments, the plurality of high-intensity volumes comprise one or more members selected from the group consisting of a kidney, a liver, and a bladder (e.g., a urinary bladder).

In another aspect, the invention is directed to a system for automatically processing 3D images of a subject to identify and/or characterize (e.g., grade) cancerous lesions within the subject, the system comprising: a processor of a computing device; and a memory having instructions stored thereon, wherein the instructions, when executed by the processor, cause the processor to: (a) receive (e.g., and/or access), a 3D functional image of the subject obtained using a functional imaging modality [e.g., positron emission tomography (PET); e.g., single-photon emission computed tomography (SPECT)] [e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (b) automatically detect one or more hotspots within the 3D functional image, each hotspot corresponding to a local region of elevated intensity with respect to its surrounding and representing (e.g., indicative of) a potential cancerous lesion within the subject; (c) cause rendering of a graphical representation of the one or more hotspots for display within an interactive graphical user interface (GUI) (e.g., a quality control and reporting GUI); (d) receive, via the interactive GUI, a user selection of a final hotspot set comprising at least a portion (e.g., up to all) of the one or more automatically detected hotspots (e.g., for inclusion in a report); and (e) store and/or provide, for display and/or further processing, the final hotspot set.

In certain embodiments, the instructions cause the processor to: (f) receive, via the GUI, a user selection of one or more additional, user-identified, hotspots for inclusion in the final hotspot set; and (g) update, the final hotspot set to include the one or more additional user-identified hotspots.

In certain embodiments, at step (b) the instructions cause the processor to use one or more machine learning modules.

In another aspect, the invention is directed to a system for automatically processing 3D images of a subject to identify and characterize (e.g., grade) cancerous lesions within the subject, the system comprising: a processor of a computing device; and a memory having instructions stored thereon, wherein the instructions, when executed by the processor, cause the processor to: (a) receive (e.g., and/or access) a 3D functional image of the subject obtained using a functional imaging modality [e.g., positron emission tomography (PET); e.g., single-photon emission computed tomography (SPECT)] [e.g., wherein the 3D functional image comprises a plurality of voxels, each representing a particular physical volume within the subject and having an intensity value that represents detected radiation emitted from the particular physical volume, wherein at least a portion of the plurality of voxels of the 3D functional image represent physical volumes within the target tissue region]; (b) automatically detect one or more hotspots within the 3D functional image, each hotspot corresponding to a local region of elevated intensity with respect to its surrounding and representing (e.g., indicative of) a potential cancerous lesion within the subject; (c) automatically determine, for each of at least a portion of the one or more hotspots, an anatomical classification corresponding to a particular anatomical region and/or group of anatomical regions within the subject in which the potential cancerous lesion that the hotspot represents is determined [e.g., by the processor (e.g., based on a received and/or determined 3D segmentation map)] to be located [e.g., within a prostate, a pelvic lymph node, a non-pelvic lymph node, a bone (e.g., a bone metastatic region), and a soft tissue region not situated in prostate or lymph node]; and (d) store and/or provide, for display and/or further processing, an identification of the one or more hotspots along with, for each hotspot, the anatomical classification corresponding to the hotspot.

In certain embodiments, the instructions cause the processor to perform step (b) using one or more machine learning modules.

Features of embodiments described with respect to one aspect of the invention may be applied with respect to another aspect of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other objects, aspects, features, and advantages of the present disclosure will become more apparent and better understood by referring to the following description taken in conjunction with the accompanying drawings, in which:

FIG. 6F is a screenshot of a portion of a GUI showing a quality control checklist, according to an illustrative embodiment.

FIG. 6G is a screenshot of a report generated by a user, using an embodiment of the automated lesion detection tools described herein, according to an illustrative embodiment.

DETAILED DESCRIPTION

Figure 1A:
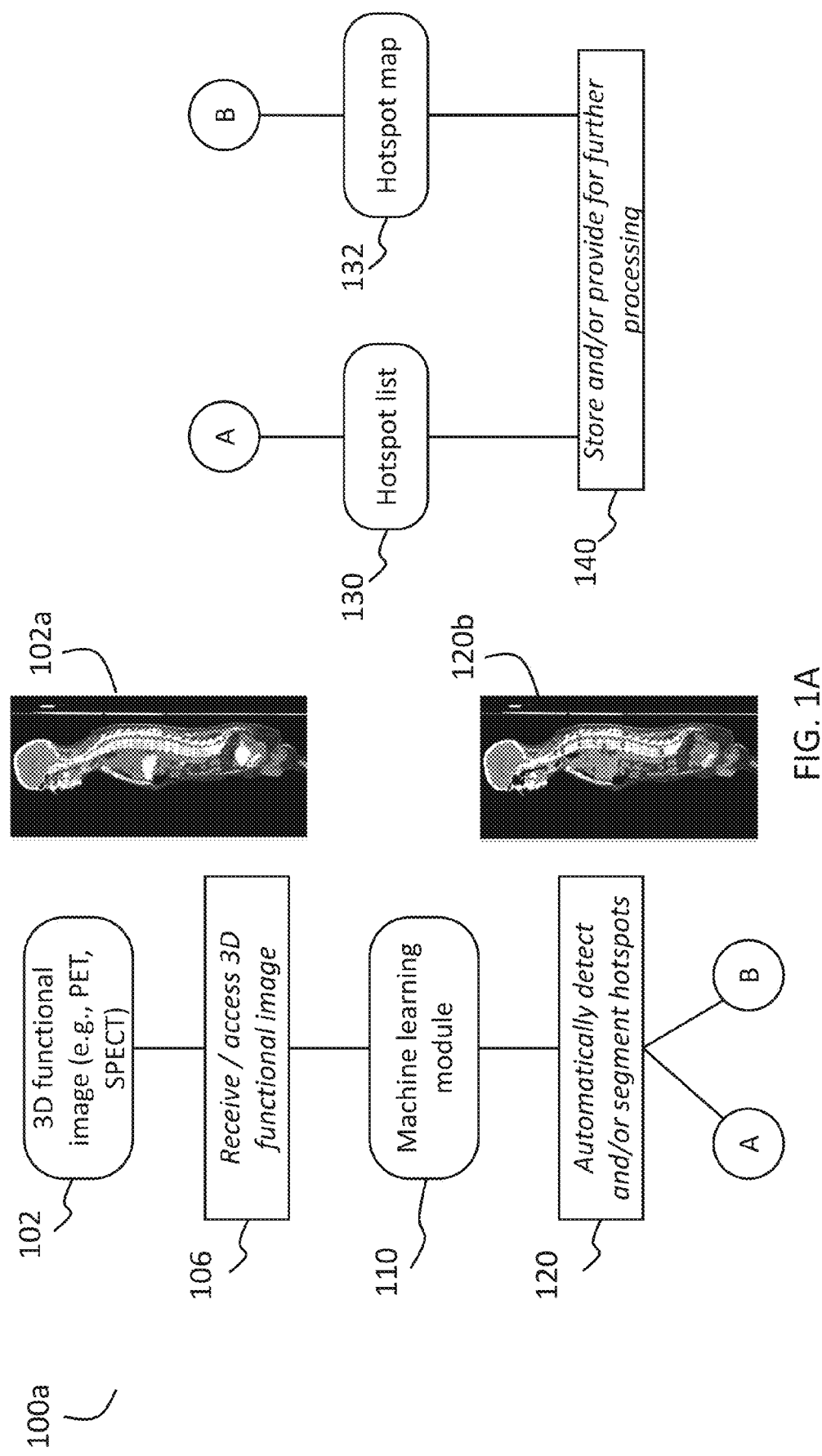
FIG. 1A is a block flow diagram of an example process for artificial intelligence (AI)-based lesion detection, according to an illustrative embodiment.

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Headers are provided for the convenience of the reader—the presence and/or placement of a header is not intended to limit the scope of the subject matter described herein.

A. Nuclear Medicine Images

Nuclear medicine images are obtained using a nuclear imaging modality such as bone scan imaging, Positron Emission Tomography (PET) imaging, and Single-Photon Emission Tomography (SPECT) imaging.

As used herein, an "image"—for example, a 3-D image of mammal—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method.

As used herein, "3-D" or "three-dimensional" with reference to an "image" means conveying information about three dimensions. A 3-D image may be rendered as a dataset in three dimensions and/or may be displayed as a set of two-dimensional representations, or as a three-dimensional representation.

In certain embodiments, nuclear medicine images use imaging agents comprising radiopharmaceuticals. Nuclear medicine images are obtained following administration of a radiopharmaceutical to a patient (e.g., a human subject), and provide information regarding the distribution of the radiopharmaceutical within the patient. Radiopharmaceuticals are compounds that comprise a radionuclide.

As used herein, "administering" an agent means introducing a substance (e.g., an imaging agent) into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments As used herein, "radionuclide" refers to a moiety comprising a radioactive isotope of at least one element. Exemplary suitable radionuclides include but are not limited to those described herein. In some embodiments, a radionuclide is one used in positron emission tomography (PET). In some embodiments, a radionuclide is one used in single-photon emission computed tomography (SPECT). In some embodiments, a non-limiting list of radionuclides includes $^{99m}$Tc, $^{111}$In, $^{64}$Cu, $^{67}$Ga, $^{68}$Ga, $^{186}$Re, $^{188}$Re, $^{153}$Sm, $^{177}$Lu, $^{67}$Cu, $^{123}$I, $^{124}$I, $^{125}$I, $^{126}$I, $^{131}$I, $^{11}$C, $^{13}$N, $^{15}$O, $^{18}$F, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{105}$Rh, $^{111}$Ag, $^{89}$Zr, $^{225}$Ac, $^{82}$Rb, $^{75}$Br, $^{76}$Br, $^{77}$Br, $^{80}$Br, $^{80m}$Br, $^{82}$Br, $^{83}$Br, $^{211}$At and $^{192}$Ir.

As used herein, the term "radiopharmaceutical" refers to a compound comprising a radionuclide. In certain embodiments, radiopharmaceuticals are used for diagnostic and/or therapeutic purposes. In certain embodiments, radiopharmaceuticals include small molecules that are labeled with one or more radionuclide(s), antibodies that are labeled with one or more radionuclide(s), and antigen-binding portions of antibodies that are labeled with one or more radionuclide(s).

Nuclear medicine images (e.g., PET scans; e.g., SPECT scans; e.g., whole-body bone scans; e.g. composite PET-CT images; e.g., composite SPECT-CT images) detect radiation emitted from the radionuclides of radiopharmaceuticals to form an image. The distribution of a particular radiopharmaceutical within a patient may be determined by biological mechanisms such as blood flow or perfusion, as well as by specific enzymatic or receptor binding interactions. Different radiopharmaceuticals may be designed to take advantage of different biological mechanisms and/or particular specific enzymatic or receptor binding interactions and thus, when administered to a patient, selectively concentrate within particular types of tissue and/or regions within the patient. Greater amounts of radiation are emitted from regions within the patient that have higher concentrations of radiopharmaceutical than other regions, such that these regions appear brighter in nuclear medicine images. Accordingly, intensity variations within a nuclear medicine image can be used to map the distribution of radiopharmaceutical within the patient. This mapped distribution of radiopharmaceutical within the patient can be used to, for example, infer the presence of cancerous tissue within various regions of the patient's body.

For example, upon administration to a patient, technetium 99m methylenediphosphonate ($^{99m}$Tc MDP) selectively accumulates within the skeletal region of the patient, in particular at sites with abnormal osteogenesis associated with malignant bone lesions. The selective concentration of radiopharmaceutical at these sites produces identifiable hotspots—localized regions of high intensity in nuclear medicine images. Accordingly, presence of malignant bone lesions associated with metastatic prostate cancer can be inferred by identifying such hotspots within a whole-body scan of the patient. As described in the following, risk indices that correlate with patient overall survival and other prognostic metrics indicative of disease state, progression, treatment efficacy, and the like, can be computed based on automated analysis of intensity variations in whole-body scans obtained following administration of $^{99m}$Tc MDP to a patient. In certain embodiments, other radiopharmaceuticals can also be used in a similar fashion to $^{99m}$Tc MDP.

In certain embodiments, the particular radiopharmaceutical used depends on the particular nuclear medicine imaging modality used. For example 18F sodium fluoride (NaF) also accumulates in bone lesions, similar to $^{99m}$Tc MDP, but can be used with PET imaging. In certain embodiments, PET imaging may also utilize a radioactive form of the vitamin choline, which is readily absorbed by prostate cancer cells.

In certain embodiments, radiopharmaceuticals that selectively bind to particular proteins or receptors of interest—particularly those whose expression is increased in cancerous tissue may be used. Such proteins or receptors of interest include, but are not limited to tumor antigens, such as CEA, which is expressed in colorectal carcinomas, Her2/neu, which is expressed in multiple cancers, BRCA 1 and BRCA 2, expressed in breast and ovarian cancers; and TRP-1 and -2, expressed in melanoma.

For example, human prostate-specific membrane antigen (PSMA) is upregulated in prostate cancer, including metastatic disease. PSMA is expressed by virtually all prostate cancers and its expression is further increased in poorly differentiated, metastatic and hormone refractory carcinomas. Accordingly, radiopharmaceuticals corresponding to PSMA binding agents (e.g., compounds that a high affinity to PSMA) labelled with one or more radionuclide(s) can be used to obtain nuclear medicine images of a patient from which the presence and/or state of prostate cancer within a variety of regions (e.g., including, but not limited to skeletal regions) of the patient can be assessed. In certain embodiments, nuclear medicine images obtained using PSMA binding agents are used to identify the presence of cancerous tissue within the prostate, when the disease is in a localized state. In certain embodiments, nuclear medicine images obtained using radiopharmaceuticals comprising PSMA binding agents are used to identify the presence of cancerous tissue within a variety of regions that include not only the prostate, but also other organs and tissue regions such as lungs, lymph nodes, and bones, as is relevant when the disease is metastatic.

In particular, upon administration to a patient, radionuclide labelled PSMA binding agents selectively accumulate within cancerous tissue, based on their affinity to PSMA. In a similar manner to that described above with regard to $^{99m}$Tc MDP, the selective concentration of radionuclide labelled PSMA binding agents at particular sites within the patient produces detectable hotspots in nuclear medicine images. As PSMA binding agents concentrate within a variety of cancerous tissues and regions of the body expressing PSMA, localized cancer within a prostate of the patient and/or metastatic cancer in various regions of the patient's body can be detected, and evaluated. Risk indices that correlate with patient overall survival and other prognostic metrics indicative of disease state, progression, treatment efficacy, and the like, can be computed based on automated analysis of intensity variations in nuclear medicine images obtained following administration of a PSMA binding agent radiopharmaceutical to a patient.

A variety of radionuclide labelled PSMA binding agents may be used as radiopharmaceutical imaging agents for nuclear medicine imaging to detect and evaluate prostate cancer. In certain embodiments, the particular radionuclide labelled PSMA binding agent that is used depends on factors such as the particular imaging modality (e.g., PET; e.g., SPECT) and the particular regions (e.g., organs) of the patient to be imaged. For example, certain radionuclide labelled PSMA binding agents are suited for PET imaging, while others are suited for SPECT imaging. For example, certain radionuclide labelled PSMA binding agents facilitate imaging a prostate of the patient, and are used primarily when the disease is localized, while others facilitate imaging organs and regions throughout the patient's body, and are useful for evaluating metastatic prostate cancer.

A variety of PSMA binding agents and radionuclide labelled versions thereof are described in U.S. Pat. Nos. 8,778,305, 8,211,401, and 8,962,799, each of which are incorporated herein by reference in their entireties. Several PSMA binding agents and radionuclide labelled versions thereof are also described in PCT Application PCT/US2017/058418, filed Oct. 26, 2017 (PCT publication WO 2018/081354), the content of which is incorporated herein by reference in its entirety. Section C, below, describes several example PSMA binding agents and radionuclide labelled versions thereof, as well.

B. Automated Lesion Detection and Analysis i. Automated Lesion Detection

In certain embodiments, the systems and methods described herein utilize machine learning techniques for automated image segmentation and detection of hotspots corresponding to and indicative of possible cancerous lesions within a subject.

In certain embodiments, the systems and methods described herein may be implemented in a cloud-based platform, for example as described in PCT/US2017/058418, filed Oct. 26, 2017 (PCT publication WO 2018/081354), the content of which is hereby incorporated by reference in its entirety.

In certain embodiments, as described herein, machine learning modules implement one or more machine learning techniques, such as random forest classifiers, artificial neural networks (ANNs), convolutional neural networks (CNNs), and the like. In certain embodiments, machine learning modules implementing machine learning techniques are trained, for example using manually segmented and/or labeled images, to identify and/or classify portions of images. Such training may be used to determine various parameters of machine learning algorithms implemented by a machine learning module, such as weights associated with layers in neural networks. In certain embodiments, once a machine learning module is trained, e.g., to accomplish a specific task such as identifying certain target regions within images, values of determined parameters are fixed and the (e.g., unchanging, static) machine learning module is used to process new data (e.g., different from the training data) and accomplish its trained task without further updates to its parameters (e.g., the machine learning module does not receive feedback and/or update). In certain embodiments, machine learning modules may receive feedback, e.g., based on user review of accuracy, and such feedback may be used as additional training data, to dynamically update the machine learning module. In some embodiments, the trained machine learning module is a classification algorithm with adjustable and/or fixed (e.g., locked) parameters, e.g., a random forest classifier.

In certain embodiments, machine learning techniques are used to automatically segment anatomical structures in anatomical images, such as CT, MRI, ultra-sound, etc. images, in order to identify volumes of interest corresponding to specific target tissue regions such as specific organs (e.g., a prostate, lymph node regions, a kidney, a liver, a bladder, an aorta portion) as well as bones. In this manner, machine learning modules may be used to generate segmentation masks and/or segmentation maps (e.g., comprising a plurality of segmentation masks, each corresponding to and identifying a particular target tissue region) that can be mapped to (e.g., projected onto) functional images, such as PET or SPECT images, to provide anatomical context for evaluating intensity fluctuations therein. Approaches for segmenting images and using the obtained anatomical context for analysis of nuclear medicine images are described, for example, in further detail in PCT/US2019/012486, filed Jan. 7, 2019 (PCT publication WO 2019/136349) and PCT/EP2020/050132, filed Jan. 6, 2020 (PCT publication WO 2020/144134), the contents of each of which is hereby incorporated by reference in their entirety.

In certain embodiments, potential lesions are detected as regions of locally high intensity in functional images, such as PET images. These localized regions of elevated intensity, also referred to as hotspots, can be detected using image processing techniques not necessarily involving machine learning, such as filtering and thresholding, and segmented using approaches such as the fast marching method. Anatomical information established from the segmentation of anatomical images allows for anatomical labeling of detected hotspots representing potential lesions. Anatomical context may also be useful in allowing different detection and segmentation techniques to be used for hotspot detection in different anatomical regions, which can increase sensitivity and performance.

In certain embodiments, automatically detected hotspots may be presented to a user via an interactive graphical user interface (GUI). In certain embodiments, to account for target lesions detected by the user (e.g., physician), but that are missed or poorly segmented by the system, a manual segmentation tool is included in the GUI, allowing the user to manually "paint" regions of images that they perceive as corresponding to lesions of any shape and size. These manually segmented lesions may then be included, along with selected automatically detected target lesions, in subsequently generated reports.

ii. AI-Based Lesion Detection

In certain embodiments, the systems and methods described herein utilize one or more machine learning modules to analyze intensities of 3D functional images and detect hotspot representing potential lesions. For example, by collecting a dataset of PET/CT images in which hotspots that represent lesions have been manually detected and segmented, training material for AI-based lesion detection algorithms can be obtained. These manually labeled images can be used to train one or more machine learning algorithms to automatically analyze functional images (e.g., PET images) to accurately detect and segment hotspots corresponding to cancerous lesions.

FIG. 1A shows an example process 100a for automated lesion detection and/or segmentation using machine learning modules that implement machine learning algorithms, such as ANNs, CNNs, and the like. As shown in FIG. 1A, a 3D functional image 102, such as a PET or SPECT image, is received 106 and used as input to a machine learning module 110. FIG. 1A shows an example PET image, obtained using PyL™ as a radiopharmaceutical 102a. The PET image 102a is shown overlaid on a CT image (e.g., as a PET/CT image), but the machine learning module 110 may receive the PET (e.g., or other functional image) itself (e.g., not including the CT, or other anatomical image) as input. In certain embodiments, as described below, an anatomical image may also be received as input. The machine learning module automatically detects and/or segments hotspots 120 determined (by the machine learning module) to represent potential cancerous lesions. An example image showing hotspots appearing in a PET image 120b is shown in FIG. 1A as well. Accordingly, the machine learning module generates, as output, one or both of (i) a hotspot list 130 and (ii) a hotspot map 132.

In certain embodiments, the hotspot list identifies locations (e.g., centers of mass) of the detected hotspots. In certain embodiments, the hotspot map is identifies 3D volumes and/or delineates 3D boundaries of detected hotspots, as determined via image segmentation performed by the machine learning module 110. The hotspot list and/or hotspot map may be stored and/or provided (e.g., to other software modules) for display and/or further processing 140.

In certain embodiments, machine learning-based lesion detection algorithms may be trained on, and utilize, not only functional image information (e.g., from a PET image), but also anatomical information. For example, in certain embodiments, one or more machine learning modules used for lesion detection and segmentation may be trained on, and receive as input, two channels—a first channel corresponding to a portion of a PET image, and a second channel corresponding to a portion of a CT image. In certain embodiments, information derived from an anatomical (e.g., CT) image may also be used as input to machine learning modules for lesion detection and/or segmentation. For example, in certain embodiments, 3D segmentation maps identifying various tissue regions within an anatomical and/or functional image can also be used to provide anatomical context.

Figure 1B:
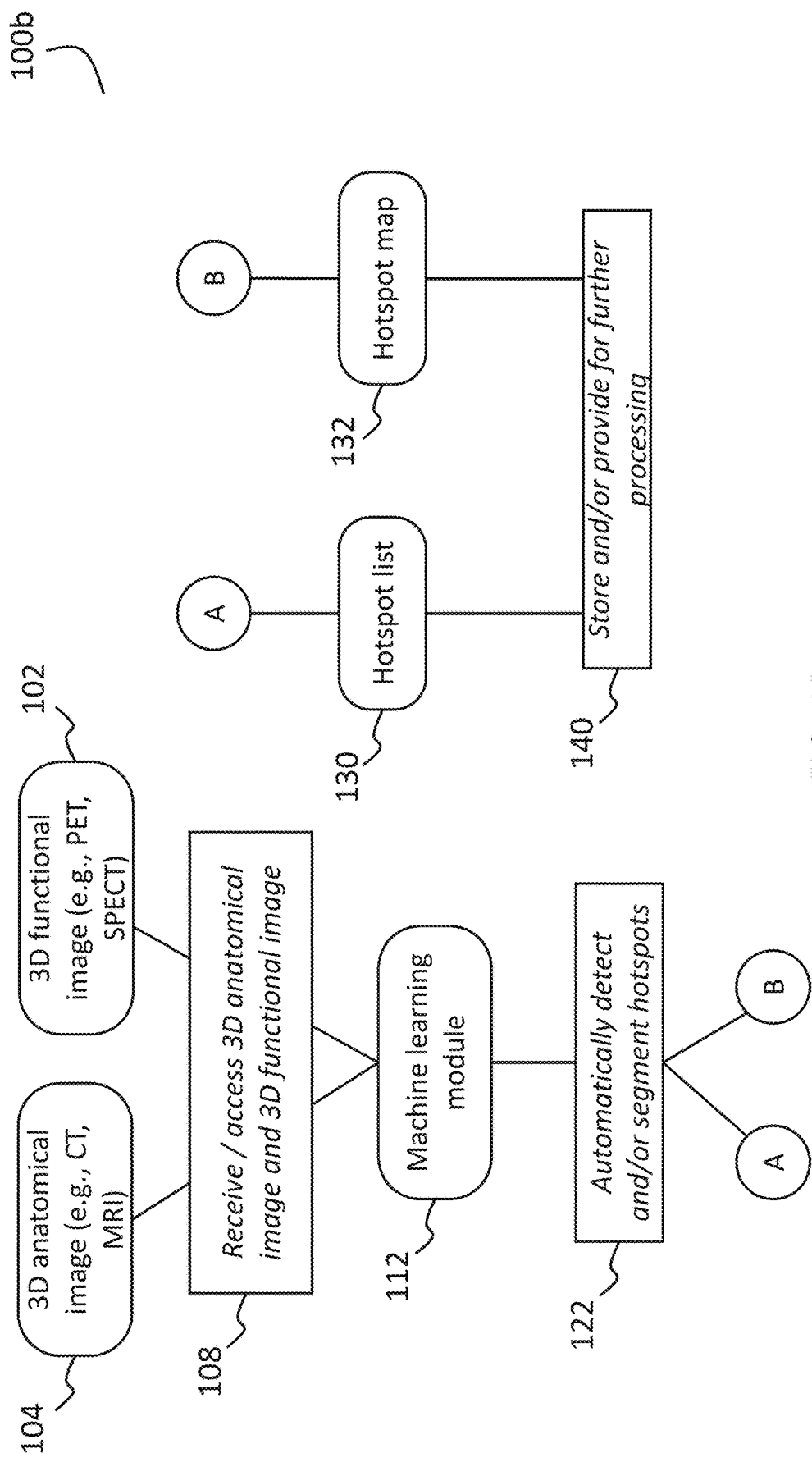
FIG. 1B is a block flow diagram of an example process for AI-based lesion detection, according to an illustrative embodiment.

FIG. 1B shows an example process 100b in which both a 3D anatomical image 104, such as a CT or MR image, and a 3D functional image 102 are received 108 and used as input to a machine learning module 112 that performs hotspot detection and/or segmentation 122 based on information (e.g., voxel intensities) from both the 3D anatomical image 104 and the 3D functional image 102 as described herein. A hotspot list 130 and/or hotspot map 132 may be generated as output from the machine learning module, and stored/provided for further processing (e.g., graphical rendering for display, subsequent operations by other software modules, etc.) 140.

In certain embodiments, automated lesion detection and analysis (e.g., for inclusion in a report) includes three tasks: (i) detection of hotspots corresponding to lesions, (ii) segmentation of detected hotspots (e.g., to identify, within a functional image, a 3D volume corresponding to each lesion), and (iii) classification of detected hotspots as having high or low probability of corresponding to a true lesion within the subject (e.g., and thus appropriate for inclusion in a radiologist report or not). In certain embodiments, one or more machine learning modules may be used to accomplish these three tasks, e.g., one by one (e.g., in sequence) or in combination. For example, in certain embodiments, a first machine learning module is trained to detect hotspots and identify hotspot locations, a second machine learning module is trained to segment hotspots, and a third machine learning module is trained to classify detected hotspots, for example using information obtained from the other two machine learning modules.

Figure 1C:
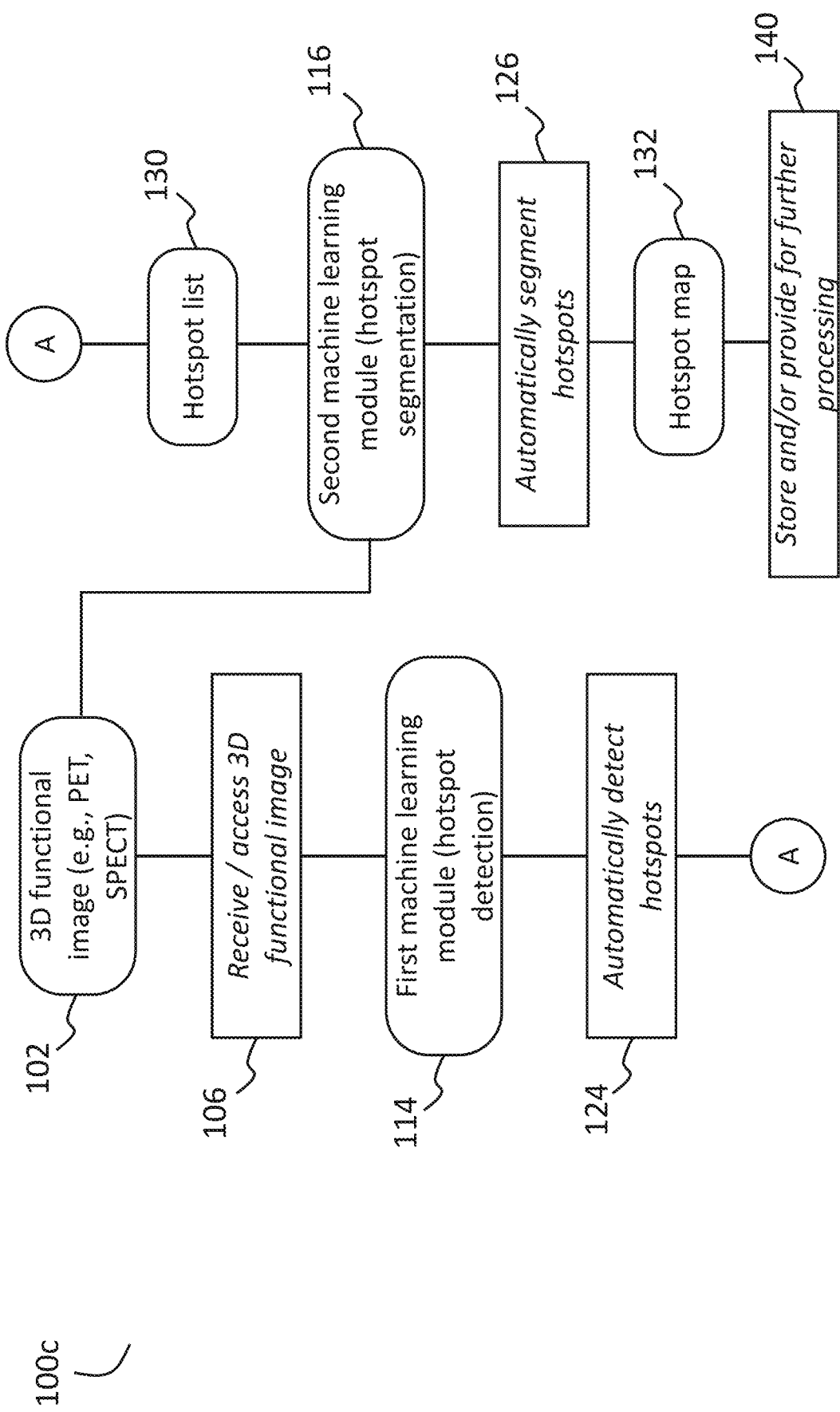
FIG. 1C is a block flow diagram of an example process for AI-based lesion detection, according to an illustrative embodiment.

For example, as shown in the example process 100c of FIG. 1C, a 3D functional image 102 may be received 106 and used as input to a first machine learning module 114 that performs automated hotspot detection. The first machine learning module 114 automatically detects one or more hotspots 124 in the 3D functional image and generates a hotspot list 130 as output. A second machine learning module 116 may receive the hotspot list 130 as input along with the 3D functional image, and perform automated hotspot segmentation, 126 to generate a hotspot map 132. As previously described, the hotspot map 132, as well as the hotspot list 130, may be stored and/or provided for further processing 140.

In certain embodiments, a single machine learning module is trained to directly segment hotspots within images (e.g., 3D functional images; e.g., to generate a 3D hotspot map identifying volumes corresponding to detected hotspots), thereby combining the first two steps of detection and segmentation of hotspots. A second machine learning module may then be used to classify detected hotspots, for example based on the segmented hotspots determined previously. In certain embodiments, a single machine learning module may be trained to accomplish all three tasks—detection, segmentation, and classification—in a single step.

iii. Lesion Index Values

In certain embodiments, lesion index values are calculated for detected hotspots to provide a measure of, for example, relative uptake within and/or size of the corresponding physical lesion. In certain embodiments, lesion index values are computed for a particular hotspot based (i) on a measure of intensity for the hotspot and (ii) reference values corresponding to measures of intensity within one or more reference volumes, each corresponding to a particular reference tissue region. For example, in certain embodiments, reference values include an aorta reference value that measures intensity within an aorta volume corresponding to a portion of an aorta and a liver reference value that measures intensity within a liver volume corresponding to a liver of the subject. In certain embodiments, intensities of voxels of a nuclear medicine image, for example a PET image, represent standard uptake values (SUVs) (e.g., having been calibrated for injected radiopharmaceutical dose and/or patient weight), and measures of hotspot intensity and/or measures reference values are SUV values. Use of such reference values in computing lesion index values is described in further detail, for example, in PCT/EP2020/050132, filed Jan. 6, 2020, the contents of which is hereby incorporated by reference in its entirety.

In certain embodiments, a segmentation mask is used to identify a particular reference volume in, for example a PET image. For a particular reference volume, a segmentation mask identifying the reference volume may be obtained via segmentation of an anatomical, e.g., CT, image. To identify voxels of the reference volume to be used for computation of the corresponding reference value, the mask may be eroded a fixed distance (e.g., at least one voxel), to create a reference organ mask that identifies a reference volume corresponding to a physical region entirely within the reference tissue region. For example, erosion distances of 3 mm and 9 mm have been used for aorta and liver reference volumes, respectively. Additional mask refinement may also be performed (e.g., to select a specific, desired, set of voxels for use in computing the reference value), for example as described below with respect to the liver reference volume.

Various measures of intensity within reference volumes may be used. For example, in certain embodiments, a robust average of voxels inside the reference volume (e.g., as defined by the reference volume segmentation mask, following erosion) may be determined as a mean of values in an interquartile range of voxel intensities ($IQR_{mean}$). Other measures, such as a peak, a maximum, a median, etc. may also be determined. In certain embodiments, an aorta reference value is determined as a robust average of SUV from voxels inside the aorta mask. The robust average is computed as the mean of the values in the interquartile range, $IQR_{mean}$.

In certain embodiments, a subset of voxels within a reference volume is selected in order to avoid impact from reference tissue regions that may have abnormally low radiopharmaceutical uptake. Although the automated segmentation techniques described and referenced herein can provide an accurate outline (e.g., identification) of regions of images corresponding to specific tissue regions, there are often areas of abnormally low uptake in the liver which should be excluded from the reference value calculation. For example, liver reference value (e.g., a liver SUV value) is computed so as to avoid impact from regions in the liver with very low tracer (radiopharmaceutical) activity, that might appear e.g., due to tumors without tracer uptake. In certain embodiments, to account for effects of abnormally low uptake in reference tissue regions the reference value calculation for the liver analyzes a histogram of intensities of voxels corresponding to the liver (e.g., voxels within an identified liver reference volume) and removes (e.g., excludes) intensities if they form a second histogram peak of lower intensities, thereby only including intensities associated with a higher intensity value peak.

Figure 2A:
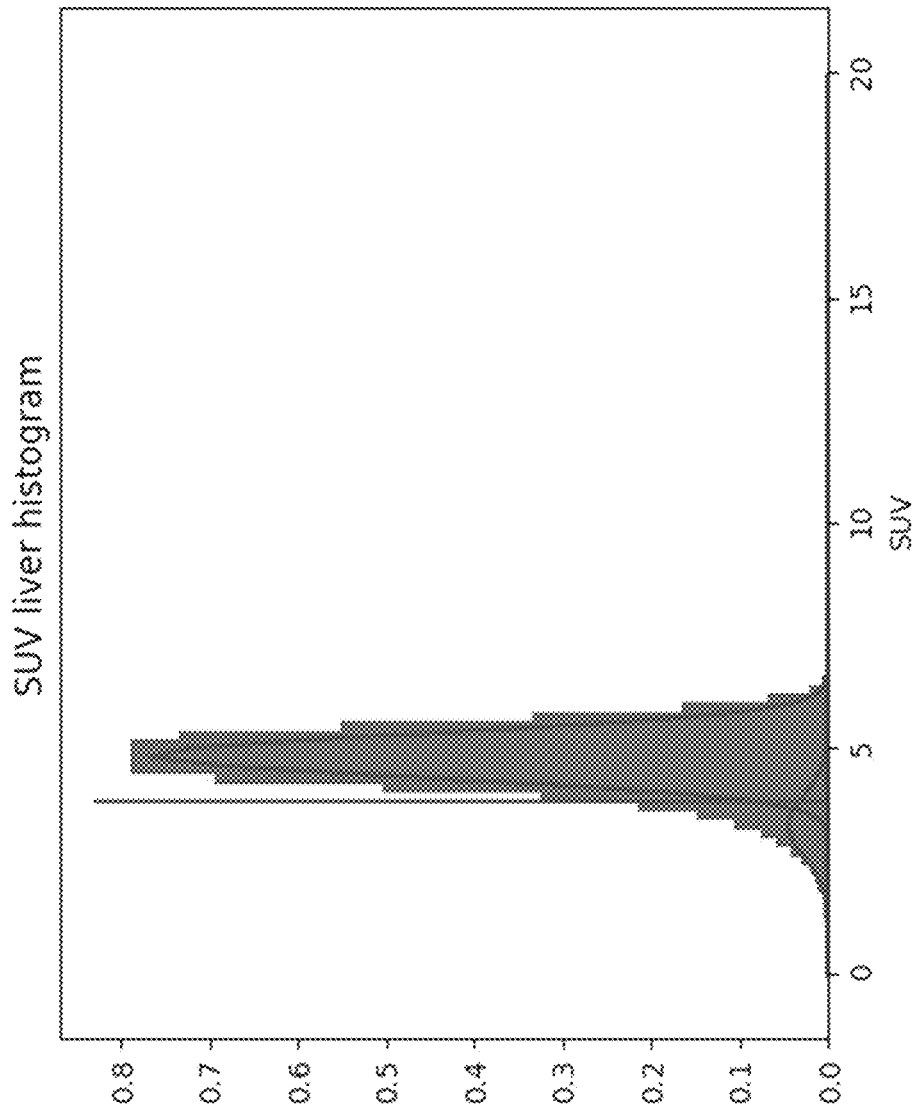
FIG. 2A is a graph showing a histogram of liver SUV values overlaid with a two-component Gaussian mixture model, according to an illustrative embodiment.

For example, for the liver, the reference SUV may be computed as a mean SUV of a major mode in a two-component Gaussian Mixture Model fitted to a histogram of SUV's of voxels within the liver reference volume (e.g., as identified by a liver segmentation mask, e.g., following the above-described erosion procedure). In certain embodiments, if the minor component has a larger mean SUV than the major component, and the minor component has at least 0.33 of the weight, an error is thrown and no reference value for the liver is determined. In certain embodiments, if the minor component has a larger mean than the major peak, the liver reference mask is kept as it is. Otherwise a separation SUV threshold is computed, defined by that the probability to belong to the major component for a SUV that is at the threshold or is larger is the same as the probability to belong to the minor component for a SUV that is at the separation threshold or is smaller. The reference liver mask is then refined by removing voxels with SUV smaller than the separation threshold. A liver reference value may then be determined as a measure of intensity (e.g., SUV) values of voxels identified by the liver reference mask, for example as described herein with respect to the aorta reference. FIG. 2A illustrates an example liver reference computation, showing a histogram of liver SUV values with Gaussian mixture components shown in red and the separation threshold marked in green.

Figure 2B:
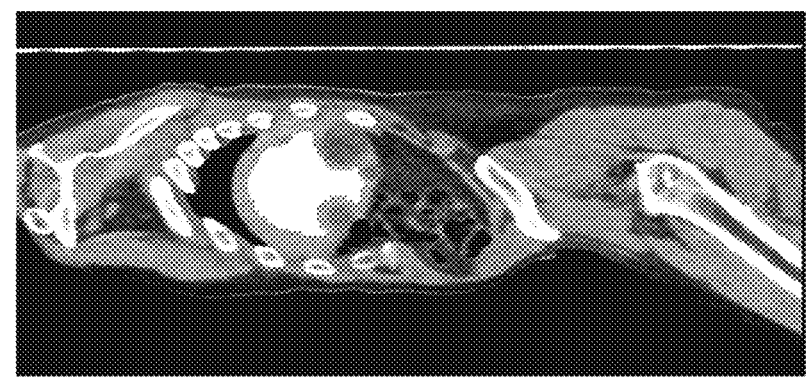
FIG. 2B is a PET image overlaid on a CT images showing a portion of a liver volume used for calculation of a liver reference value, according to an illustrative embodiment.
Figure 2B:
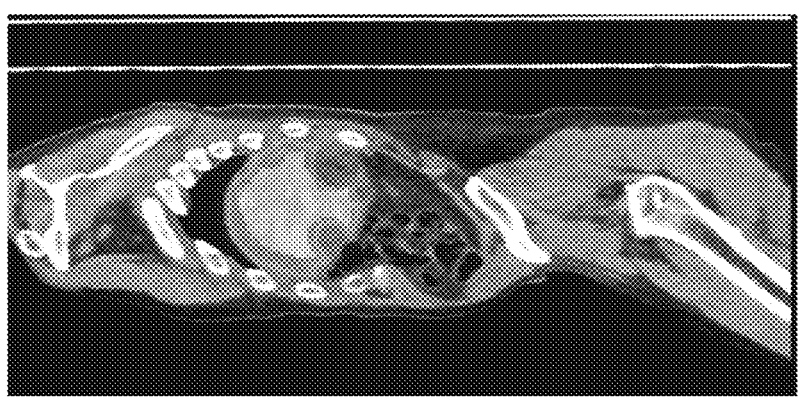

FIG. 2B shows the resulting portion of the liver volume used to calculate the liver reference value, with voxels corresponding to the lower value peak excluded from the reference value calculation. As shown in the figure, lower intensity areas towards the bottom of the liver have been excluded, as well as regions close to the liver edge.

Figure 2C:
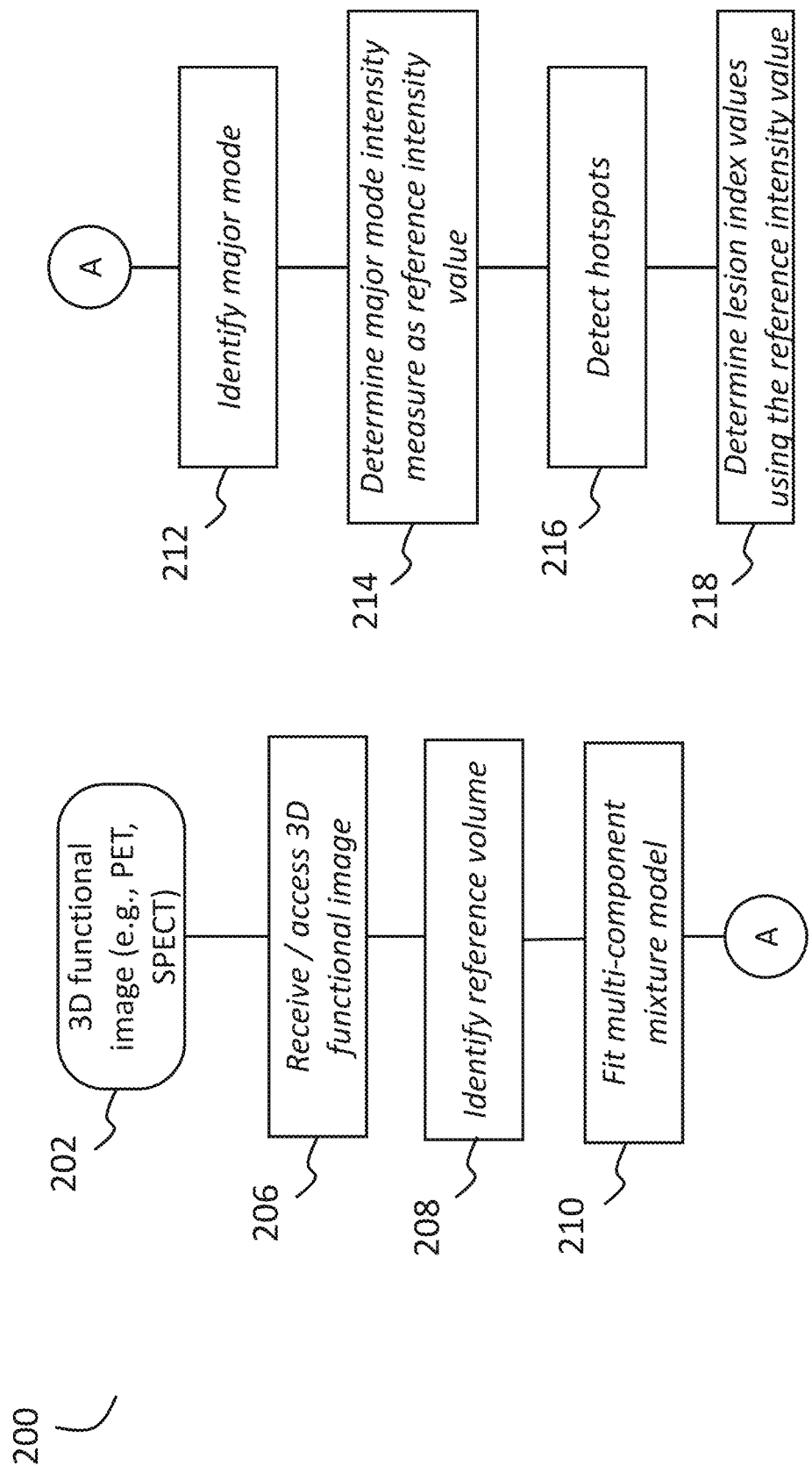
FIG. 2C is a block flow diagram of an example process for computing reference intensity values that avoids/reduces impact from tissue regions associated with low radiopharmaceutical uptake, according to an illustrative embodiment.

FIG. 2C shows an example process 200 where a multi-component mixture model is used to avoid impact from regions with low tracer uptake, as described herein with respect to liver reference volume computation. The process shown in FIG. 2C and described herein with regard to the liver may also be applied, similarly, to computation of intensity measures of other organs and tissue regions of interest as well, such as an aorta (e.g., aorta portion, such as the thoracic aorta portion or abdominal aorta portion), a parotid gland, a gluteal muscle. As shown, in FIG. 2C and described herein, in a first step, a 3D functional image 202 is received, and a reference volume corresponding to a specific reference tissue region (e.g., liver, aorta, parotid gland) is identified therein 208. A multi-component mixture model 210 is then fit to a distribution intensities (e.g., a histogram of intensities) of (e.g., within) the reference volume, and a major mode of the mixture model is identified 212. A measure of intensities associated with the major mode (e.g., and excluding contributions from intensities associated with other, minor, modes) is determined 214 and used as the reference intensity value for the identified reference volume. In certain embodiments, hotspots are detected 216 and the reference intensity value determined in this manner can be used to determine lesion index values for the detected hotspots 218, for example via approaches such as those described in PCT/US2019/012486, filed Jan. 7, 2019 and PCT/EP2020/050132, filed Jan. 6, 2020, the content of each of which is hereby incorporated by reference in its entirety.

iv. Suppression of Intensity Bleed Associated with Normal Uptake in High-Uptake Organs In certain embodiments, intensities of voxels of a functional image are adjusted in order to suppress/correct for intensity bleed associated with certain organs in which high-uptake occurs under normal circumstances. This approach may be used, for example, for organs such as a kidney, a liver, and a urinary bladder. In certain embodiments, correcting for intensity bleed associated with multiple organs is performed one organ at a time, in a step-wise fashion. For example, in certain embodiments, first kidney uptake is suppressed, then liver uptake, then urinary bladder uptake. Accordingly, the input to liver suppression is an image where kidney uptake has been corrected for (e.g., and input to bladder suppression is an image wherein kidney and liver uptake have been corrected for).

Figure 3:
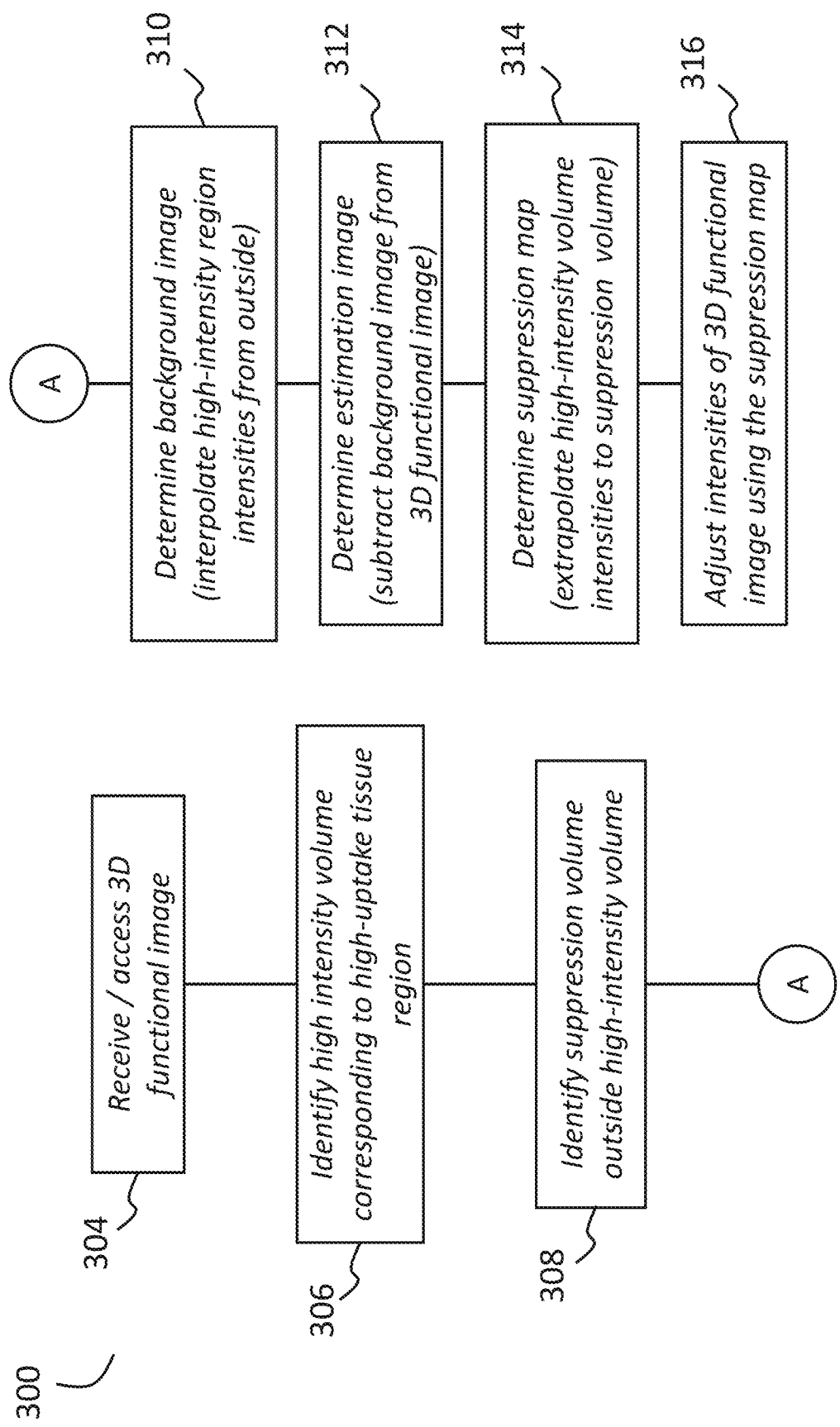
FIG. 3 is a block flow diagram of an example process for correcting for intensity bleed from one or more tissue regions associated with high radiopharmaceutical uptake, according to an illustrative embodiment.

FIG. 3 shows an example process 300 for correcting intensity blead from a high-uptake tissue region. As shown in FIG. 3, a 3D functional image is received 304 and a high intensity volume corresponding to the high-uptake tissue region is identified 306. In another step, a suppression volume outside the high-intensity volume is identified 308. In certain embodiments, as described herein, the suppression volume may be determined as a volume enclosing regions outside of, but within a pre-determined distance from, the high-intensity volume. In another step, a background image is determined 310, for example by assigning voxels within the high-intensity volume intensities determined based on intensities outside the high-intensity volume (e.g., within the suppression volume), e.g., via interpolation (e.g., using convolution). In another step, an estimation image is determined 312 by subtracting the background image from the 3D functional image (e.g., via a voxel-by-voxel intensity subtraction). In another step, a suppression map is determined 314. As described herein, in certain embodiments, the suppression map is determined using the estimation image, by extrapolating intensity values of voxels within the high-intensity volume to locations outside the high intensity volume. In certain embodiments, intensities are only extrapolated to locations within the suppression volume, and intensities of voxels outside the suppression volume are set to 0. The suppression map is then used to adjust intensities of the 3D functional image 316, for example by subtracting the suppression map from the 3D functional image (e.g., performing a voxel-by-voxel intensity subtraction).

An example approach for suppression/correction of intensity bleed from a particular organ (in certain embodiments, kidneys are treated together) for a PET/CT composite image is as follows:

1. The projected CT organ mask segmentation is adjusted to high-intensity regions of the PET image, in order to handle PET/CT misalignment. If the PET-adjusted organ mask is less than 10 pixels, no suppression is made for this organ.
2. A "background image" is computed, replacing all high uptake with interpolated background uptake within the decay distance from the PET-adjusted organ mask. This is done using convolution with Gaussian kernels.
3. Intensities that should be accounted for when estimating suppression are computed as the difference between the input PET and the background image. This "estimation image" has high intensities inside the given organ and zero intensity at locations farther than the decay distance from the given organ.
4. A suppression map is estimated from the estimation image using an exponential model. The suppression map is only non-zero in the region within the decay distance of the PET-adjusted organ segmentation.
5. The suppression map is subtracted from the original PET image.

As described above, these five steps may be repeated, for each of a set of multiple organs, in a sequential fashion.

v. Anatomical Labeling of Detected Lesions

Figure 4:
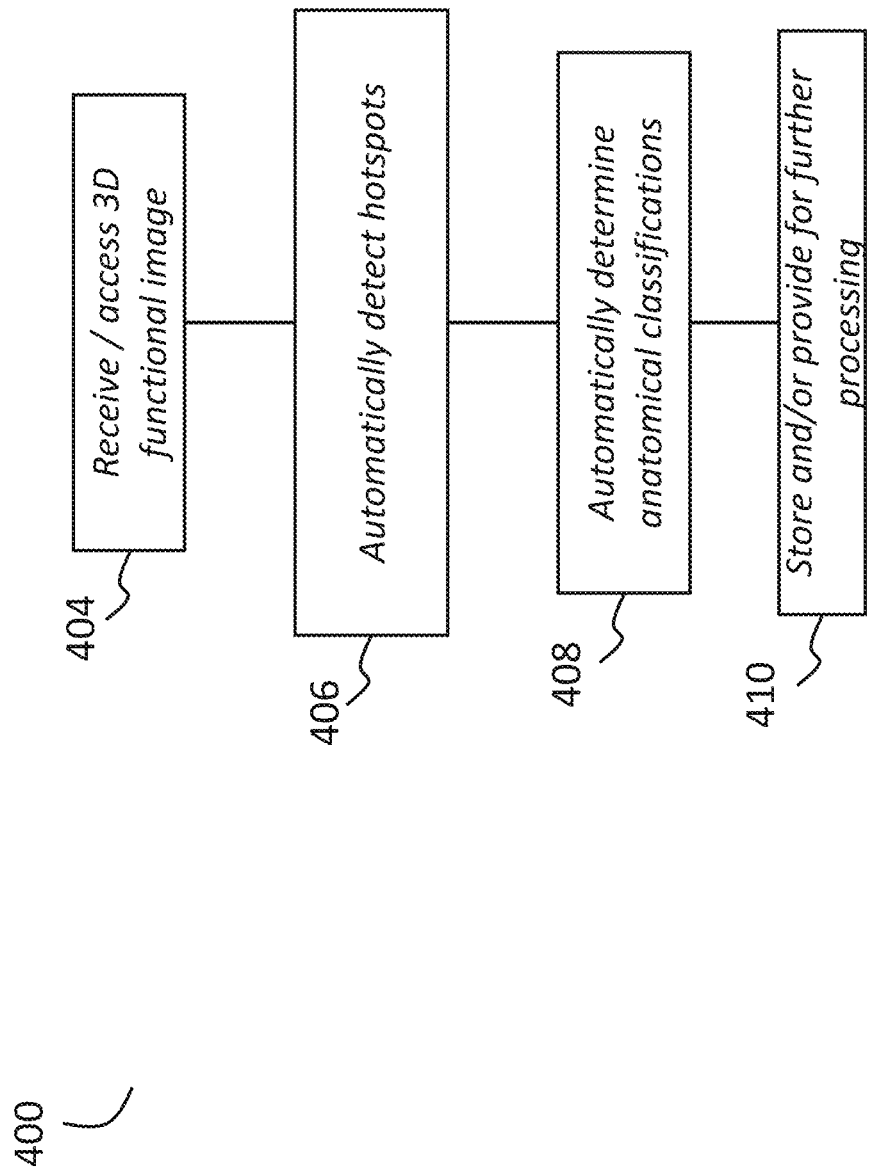
FIG. 4 is block flow diagram of an example process for anatomically labeling hotspots corresponding to detected lesions, according to an illustrative embodiment.

In certain embodiments, detected hotspots are (e.g., automatically) assigned anatomical labels that identify particular anatomical regions and/or groups of regions in which the lesions that they represent are determined to be located. For example, as shown in the example process 400 of FIG. 4, a 3D functional image may be received 404 an used to automatically detect hotspots 406, for example via any of the approaches described herein. Once hotspots are detected, anatomical classifications for each hotspot can be automatically determined 408 and each hotspot labeled with the determined anatomical classification. Automated anatomical labeling may, for example, be performed using automatically determined locations of detected hotspots along with anatomical information provided by, for example, a 3D segmentation map identifying image regions corresponding to particular tissue regions and/or an anatomical image. The hotspots and anatomical labeling of each may be stored and/or provided for further processing 410.

For example, detected hotspots may be automatically classified into one of five classes as follows:

T (prostate tumor)
N (pelvic lymph node)
Ma (non-pelvic lymph)
Mb (bone metastasis)
Mc (soft tissue metastasis not situated in prostate or lymphe node)

Table 1, below, lists tissue regions associated with each of the five classes. Hotspots corresponding to locations within any of the tissue regions associated with a particular class may, accordingly, be automatically assigned to that class.

TABLE 1

List of Tissue Regions Corresponding to Five Classes in a Lesion Anatomical Labeling Approach

| Bone Mb | Lymph nodes Ma | Pelvic lymph nodes N | Prostate T | Soft tissue Mc |
|---|---|---|---|---|
| Skull | Cervical | Template right | Prostate | Brain |
| Thorax | Supraclavicular | Template left | | Neck |
| Vertebrae lumbar | Axillary | Presacral | | Lung |
| | Mediastinal | Other, pelvic | | Esophageal |
| Vertebrae thoracic | Hilar | | | Liver |
| | Mesenteric | | | Gallbladder |
| Pelvis | Elbow | | | Spleen |
| Extremities | Popliteal | | | Pancreas |
| | Peri-/para-aortic | | | Adrenal |
| | Other, non-pelvic | | | Kidney |
| | | | | Bladder |
| | | | | Skin |
| | | | | Muscle |
| | | | | Other | vi. Graphical User Interface and Quality Control and Reporting

In certain embodiments, detected hotspots and associated information, such as computed lesion index values and anatomical labeling are displayed with an interactive graphical user interface (GUI) so as to allow for review by a medical professional, such as a physician, radiologist, technician, etc. Medical professionals may thus use the GUI to review and confirm accuracy of detected hotspots, as well as corresponding index values and/or anatomical labeling. In certain embodiments, the GUI may also allow users to identify, and segment (e.g., manually) additional hotspots within medical images, thereby allowing a medical professional to identify additional potential lesions that he/she believes the automated detection process may have missed. Once identified, lesion index values and/or anatomical labeling may also be determined for these manually identified and segmented lesions. For example, as indicated in FIG. 3, the user may review locations determined for each hotspot, as well as anatomical labeling, such as a (e.g., automatically determined) miTNM classification. The miTNM classification scheme is described in further detail, for example, in Eiber et al., "Prostate Cancer Molecular Imaging Standardized Evaluation (PROMISE): Proposed miTNM Classification for the Interpretation of PSMA-Ligand PET/CT," *J. Nucl. Med.*, vol. 59, pg. 469-78 (2018), the content of which is hereby incorporated by reference in its entirety. Once a user is satisfied with the set of detected hotspots and information computed therefrom, they may confirm their approval and generate a final, signed report that can be reviewed and used to discuss outcomes and diagnosis with a patient, and assess prognosis and treatment options.

Figure 5A:
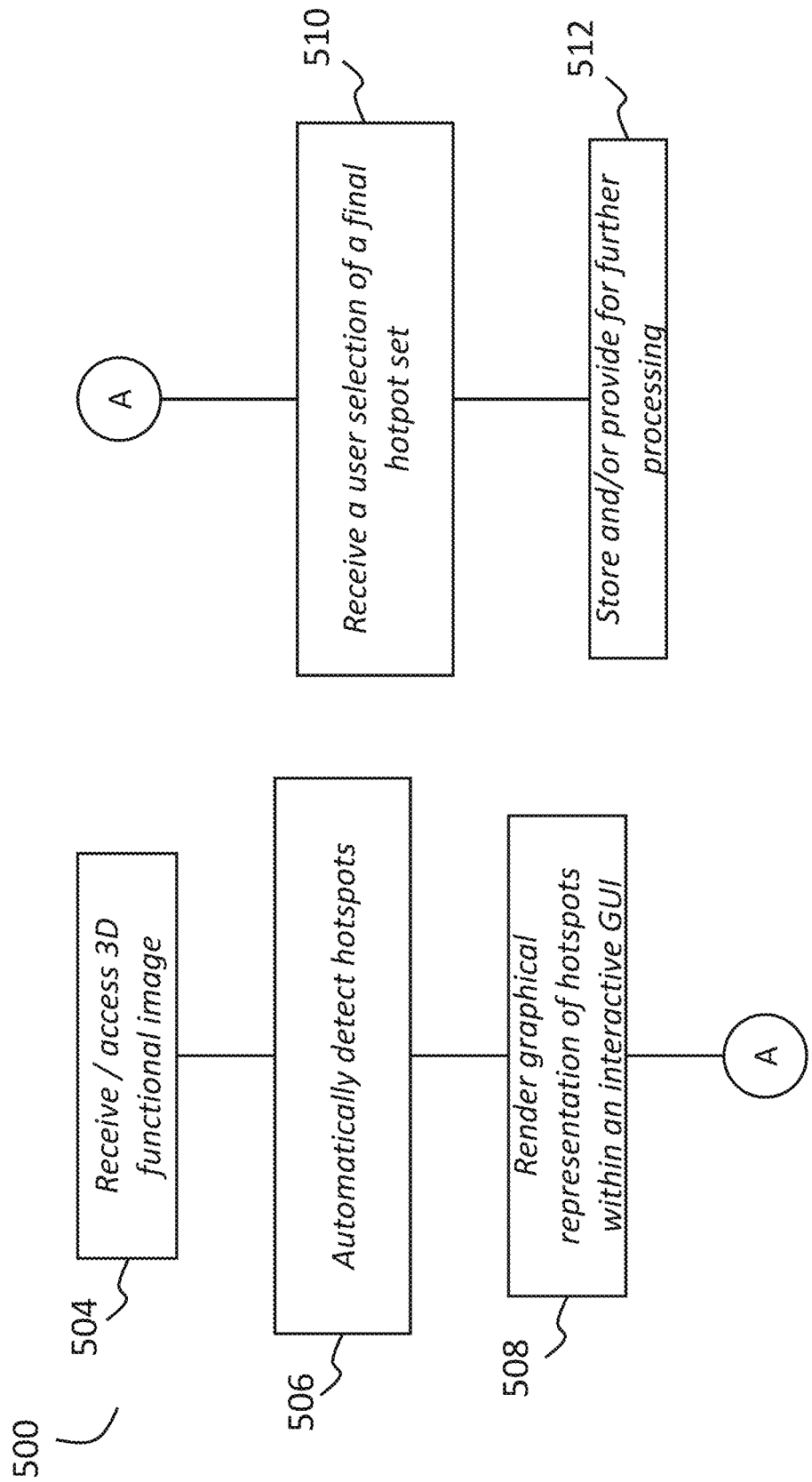
FIG. 5A is a block flow diagram of an example process for interactive lesion detection, allowing for user feedback and review via a graphical user interface (GUI), according to an illustrative embodiment.

For example, as shown in FIG. 5A, in an example process 500 for interactive hotspot review and detection, a 3D functional image is received 504 and hotspots are automatically detected 506, for example using any of the automated detection approaches described herein. The set of automated hotspots is represented and rendered graphically within an interactive GUI 508 for user review. The user may select at least a portion (e.g., up to all) of the automatically determined hotspots for inclusion in a final hotspot set 510, which may then be used for further calculations 512, e.g., to determine risk index values for the patient.

Figure 5B:
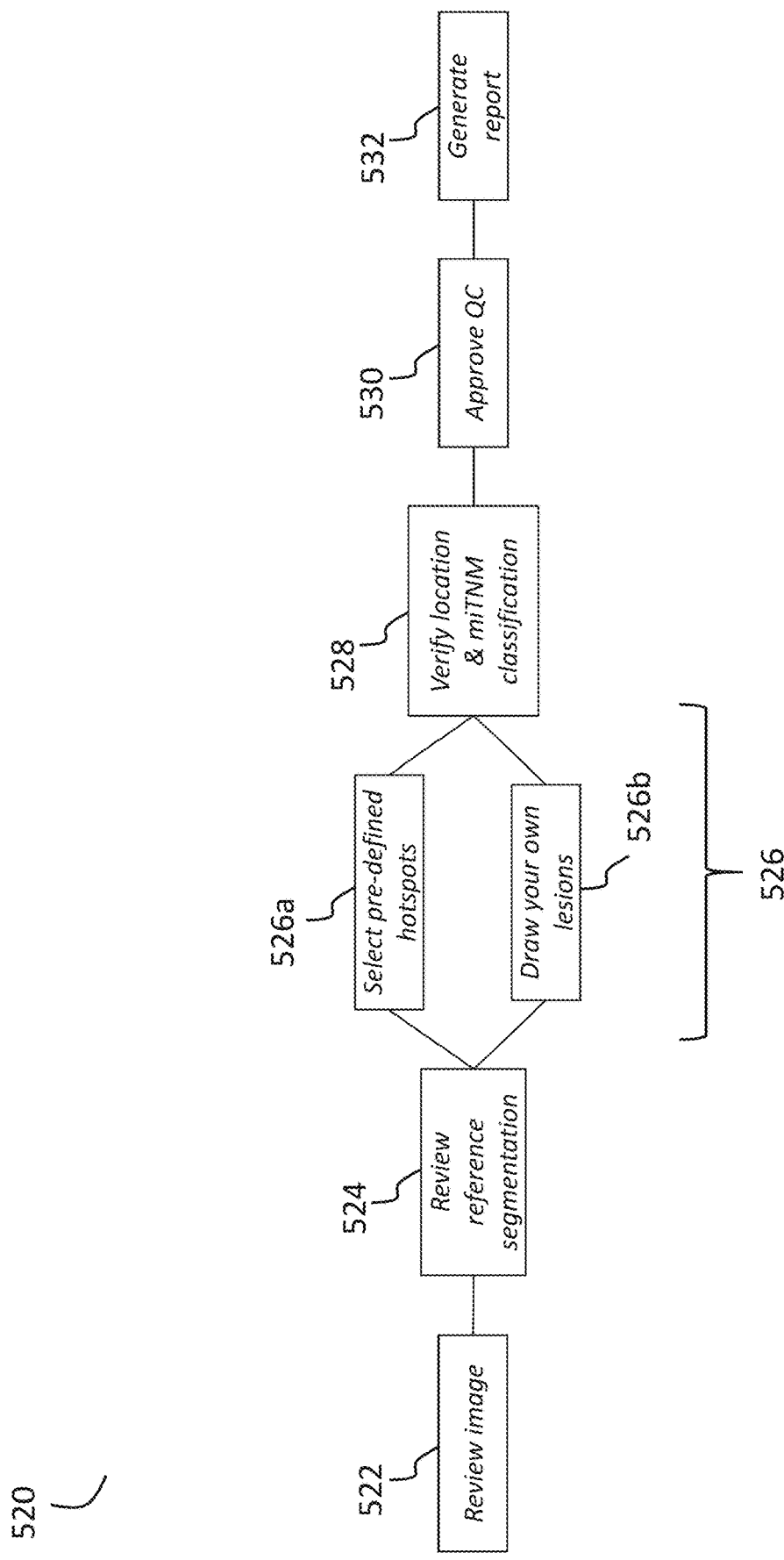
FIG. 5B is an example process for user review, quality control, and reporting of automatically detected lesions, according to an illustrative embodiment.
Figure 6A:
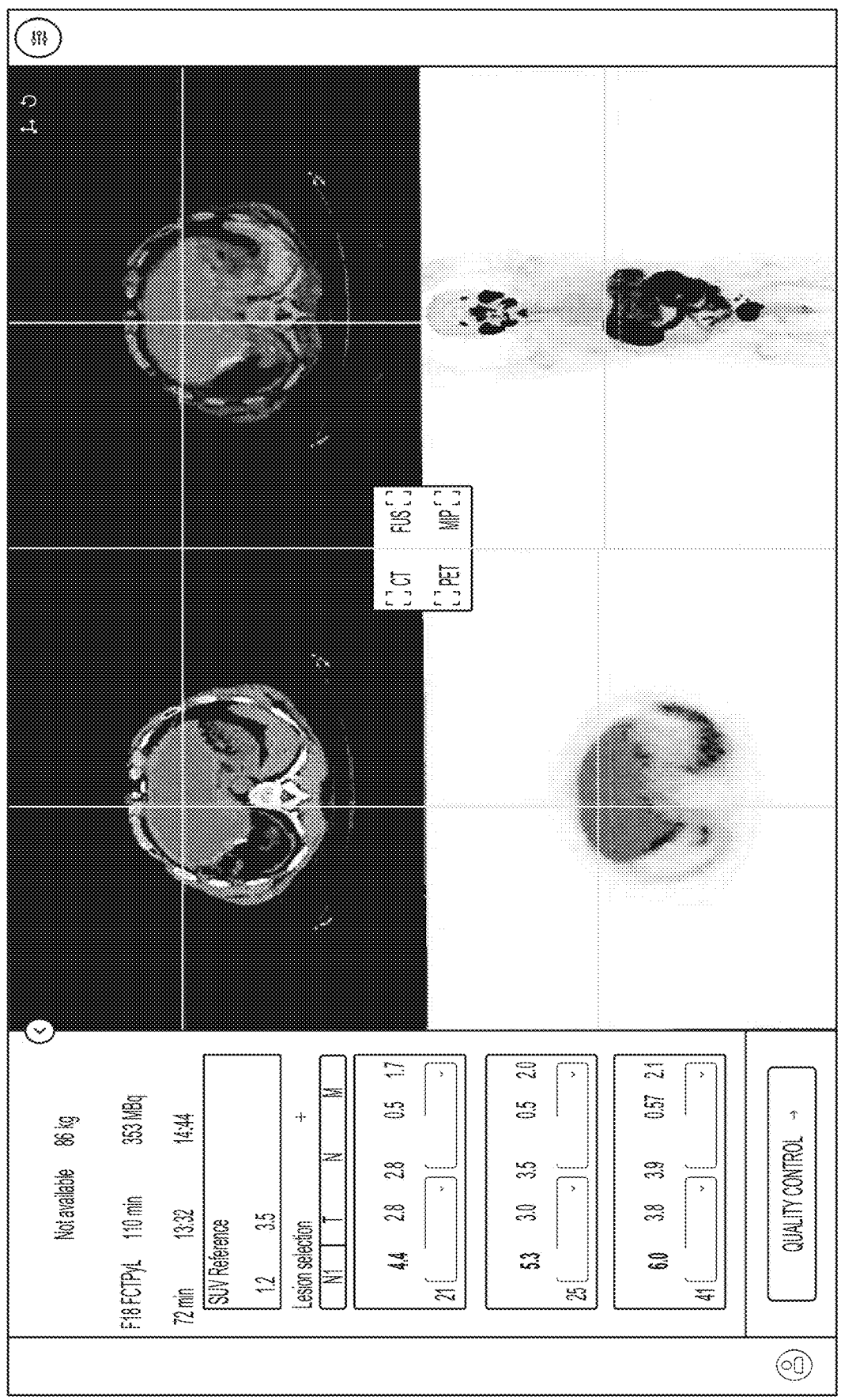
FIG. 6A is a screenshot of a GUI used for confirming accurate segmentation of a liver reference volume, according to an illustrative embodiment.
Figure 6B:
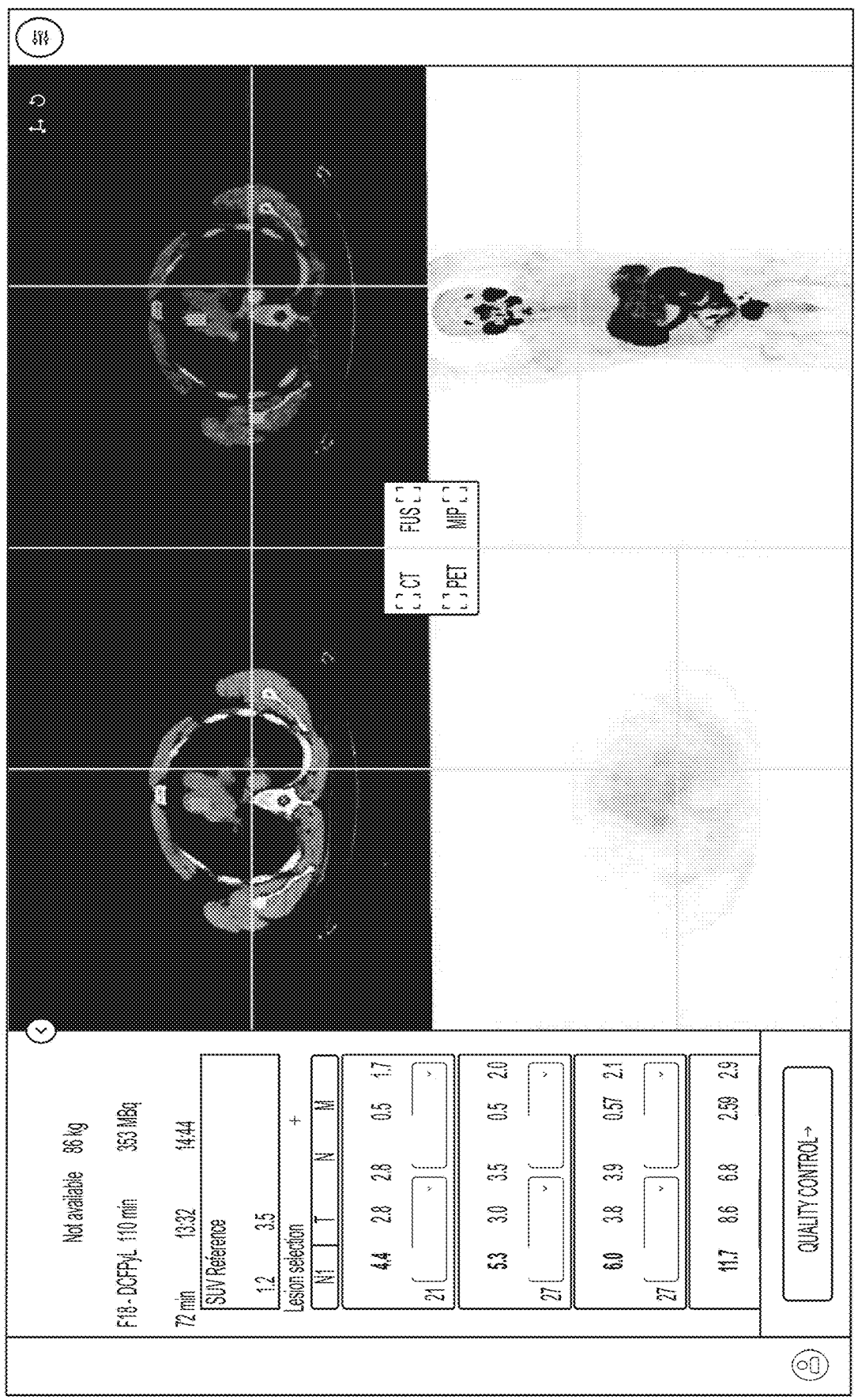
FIG. 6B is a screenshot of a GUI used for confirming accurate segmentation of an aorta portion (blood pool) reference volume, according to an illustrative embodiment.

FIG. 5B shows an example workflow 520 for user review of detected lesions and lesion index values for quality control and reporting. The example workflow allows for user review of segmented lesions as well as liver and aorta segmentation used for calculation of lesion index values as described herein. For example, in a first step, a user reviews images (e.g., a CT image) for quality 522 and accuracy of automated segmentation used to obtain liver and blood pool (e.g., aorta) reference values 524. As shown in FIGS. 6A, and 6B the GUI allows a user evaluates images and overlaid segmentation to ensure that the automated segmentation of the liver (purple color in FIG. 6A) is within healthy liver tissue and that automated segmentation of blood pool (aorta portion, shown as salmon color in FIG. 6B is within the aorta and left ventricle.

Figure 6C:
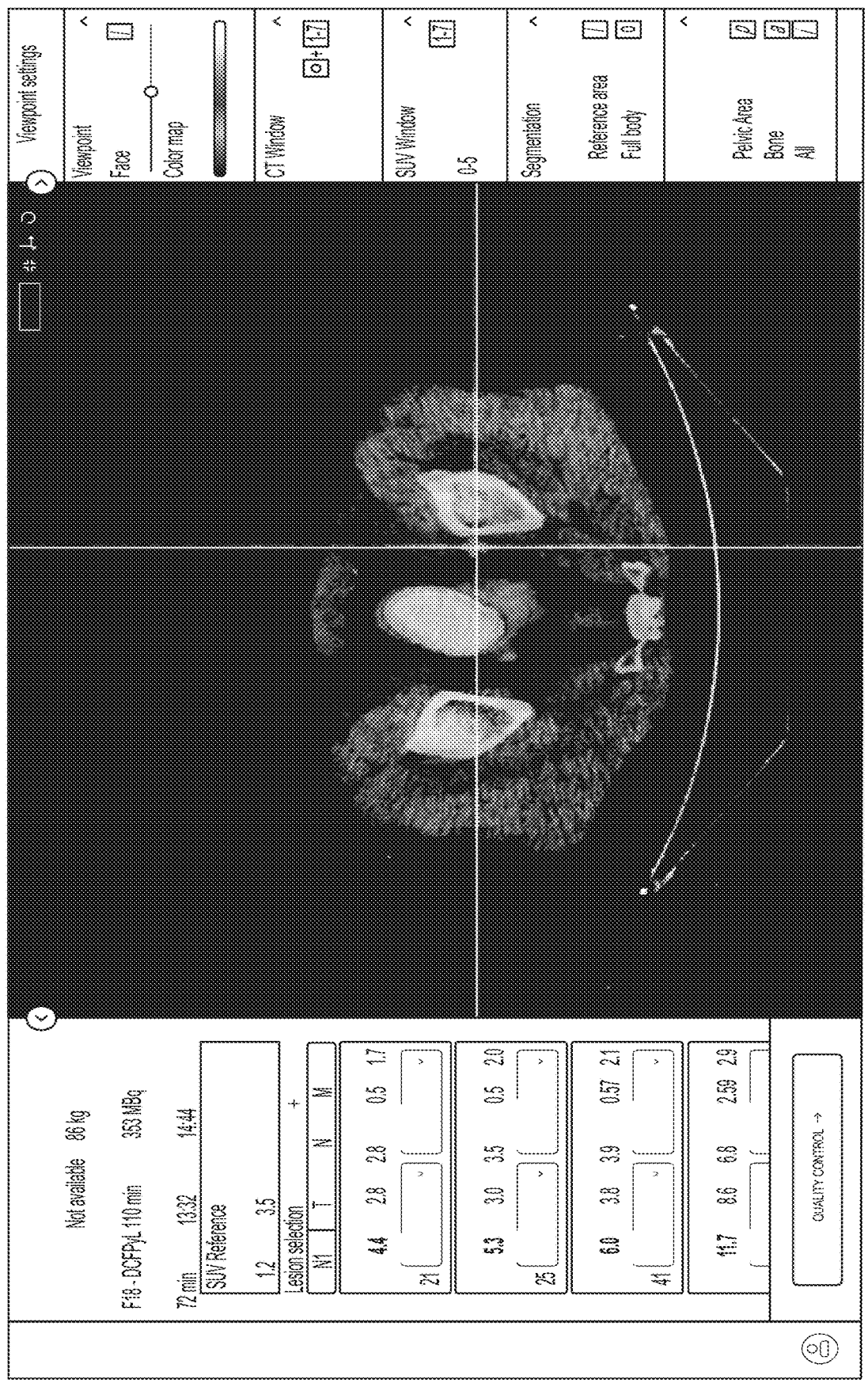
FIG. 6C is a screenshot of a GUI used for user selection and/or validation of automatically segmented hotspots corresponding to detected lesions within a subject, according to an illustrative embodiment.

In another step 526, a user validates automatically detected hotspots and/or identifies additional hotspots, e.g., to create a final set of hotspots corresponding to lesions, for inclusion in a generated report. As shown in FIG. 6C, a user may select an automatically identified hotspot by hovering over a graphical representation of the hotspot displayed within the GUI (e.g., as an overlay and/or marked region on a PET and/or CT image). To facilitate hotspot selection, the particular hotspot selected may be indicated to the user, via a color change (e.g., turning green). The user may then click on the hotspot to select it, which may be visually confirmed to the user via another color change. For example, as shown in FIG. 4C, upon selection the hotspot turns pink. Upon user selection, quantitatively determined values, such as a lesion index and/or anatomical labeling may be displayed to the user, allowing them to verify the automatically determined values 528.

In certain embodiments, the GUI allows a user to select hotspots from the set of (automatically) pre-identified hotspots to confirm they indeed represent lesions 526a and also to identify additional hotspots 562b corresponding to lesions, not having been automatically detected.

Figure 6E:
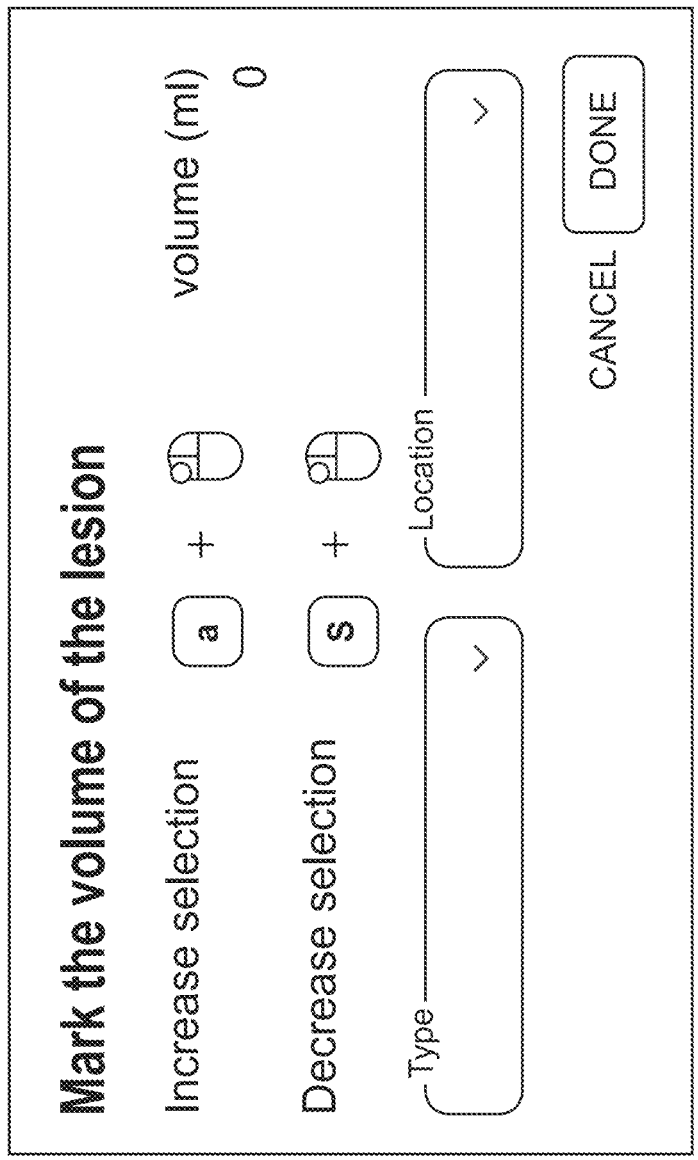
FIG. 6E is a screenshot of another portion of a GUI allowing a user to manually identify lesions within an image, according to an illustrative embodiment.
Figure 6D:
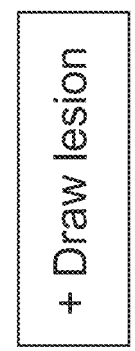
FIG. 6D is a screenshot of a portion of a GUI allowing a user to manually identify lesions within an image, according to an illustrative embodiment.

As shown in FIG. 6D and FIG. 6E, the user may use GUI tools to draw on slices of images (e.g., PET images and/or CT images; e.g., a PET image overlaid on a CT image) to mark regions corresponding to a new, manually identified lesion. Quantitative information, such as a lesion index and/or anatomical labeling may be determined for the manually identified lesion automatically, or may be manually entered by the user.

Figure 6G:
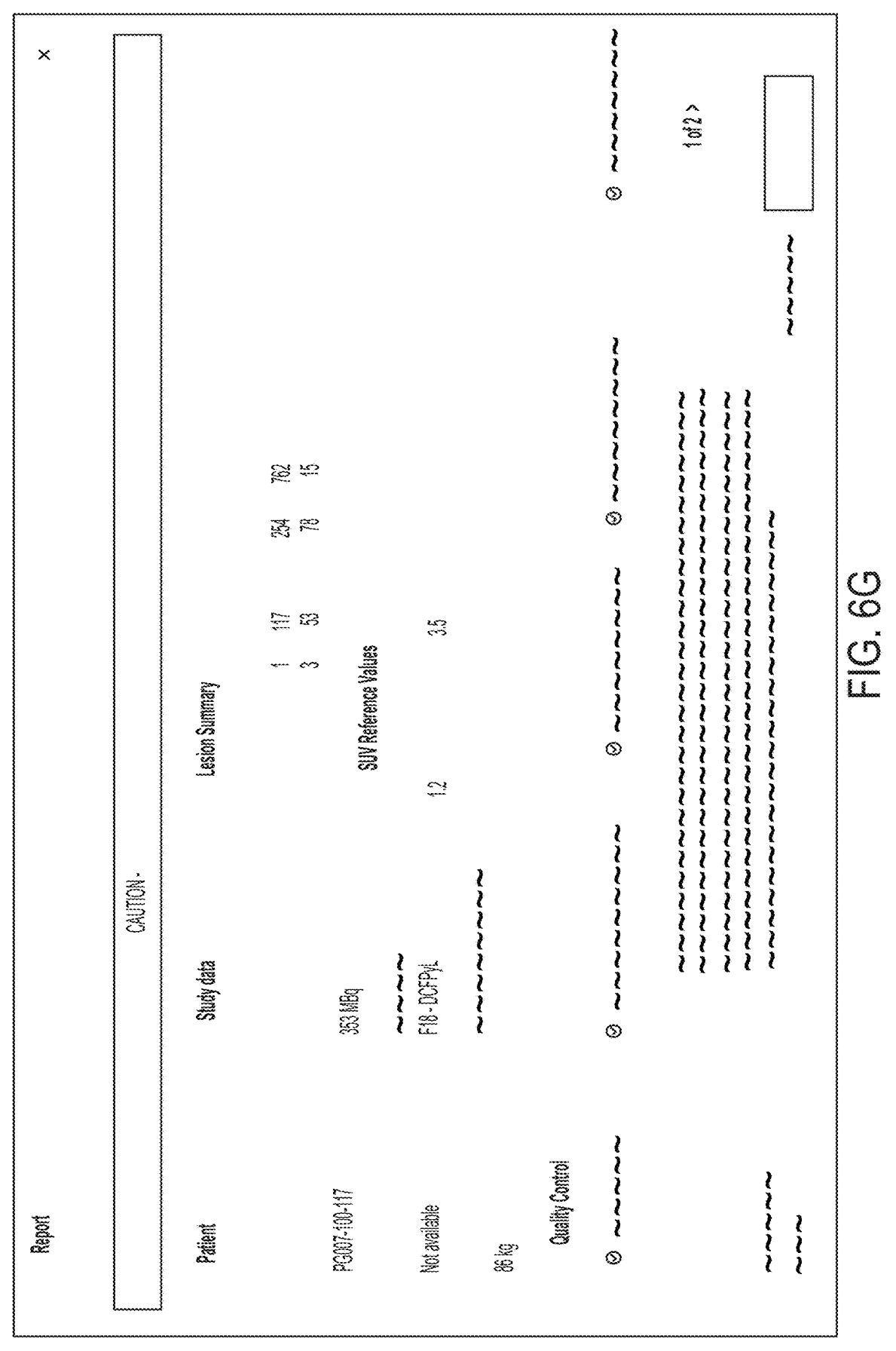

In another step, e.g., once the user has selected and/or manually identified all lesions, the GUI displays a quality control checklist for the user to review 530, as shown in FIG. 6F. Once the user reviews and completes the checklist, they may click "Create Report" to sign and generate a final report 532. An example of a generated report is shown in FIG. 6G.

C. Imaging Agents i. PET Imaging Radionuclide Labelled PSMA Binding Agents

In certain embodiments, the radionuclide labelled PSMA binding agent is a radionuclide labelled PSMA binding agent appropriate for PET imaging.

In certain embodiments, the radionuclide labelled PSMA binding agent comprises [18F]DCFPyL (also referred to as PyL™; also referred to as DCFPyL-18F):

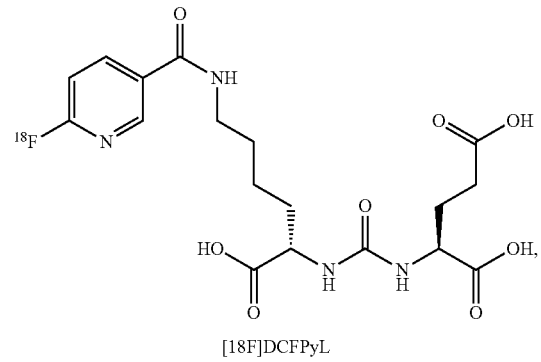 [SMILES: O=C(O)CC[C@H](NC(=O)N[C@@H](CCCCNC(=O)c1ccc([18F])nc1)C(=O)O)C(=O)O]

[18F]DCFPyL or a pharmaceutically acceptable salt thereof.

In certain embodiments, the radionuclide labelled PSMA binding agent comprises [18F]DCFBC:

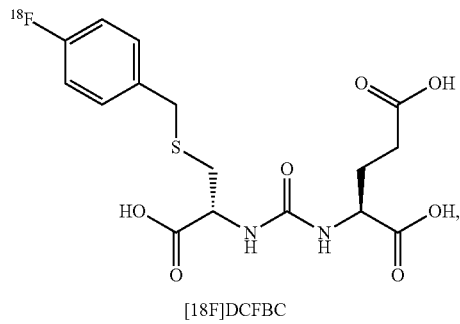 [SMILES: O=C(O)CC[C@H](NC(=O)N[C@@H](CSCc1ccc([18F])cc1)C(=O)O)C(=O)O]

[18F]DCFBC or a pharmaceutically acceptable salt thereof.

In certain embodiments, the radionuclide labelled PSMA binding agent comprises $^{68}$Ga-PSMA-HBED-CC (also referred to as $^{68}$Ga-PSMA-11):

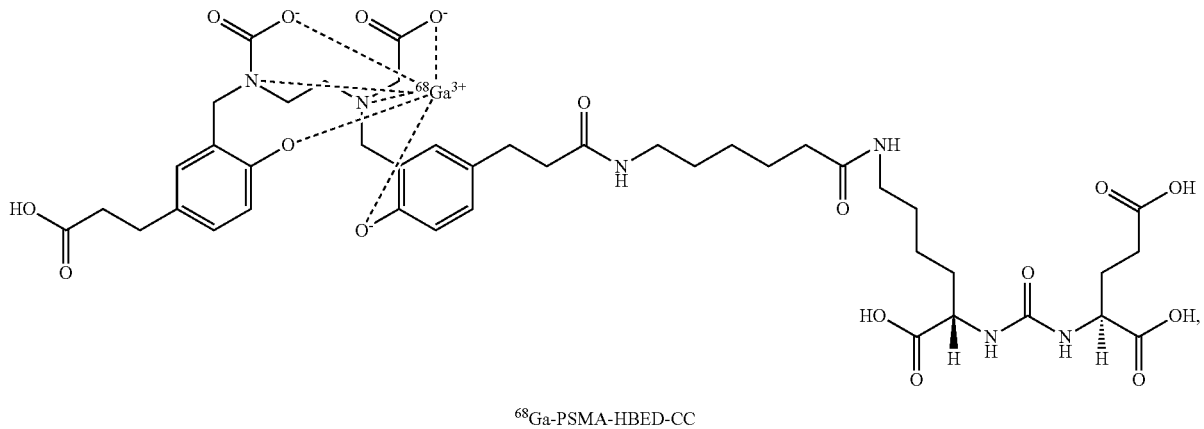

$^{68}$Ga-PSMA-HBED-CC or a pharmaceutically acceptable salt thereof.

In certain embodiments, the radionuclide labelled PSMA binding agent comprises PSMA-617:

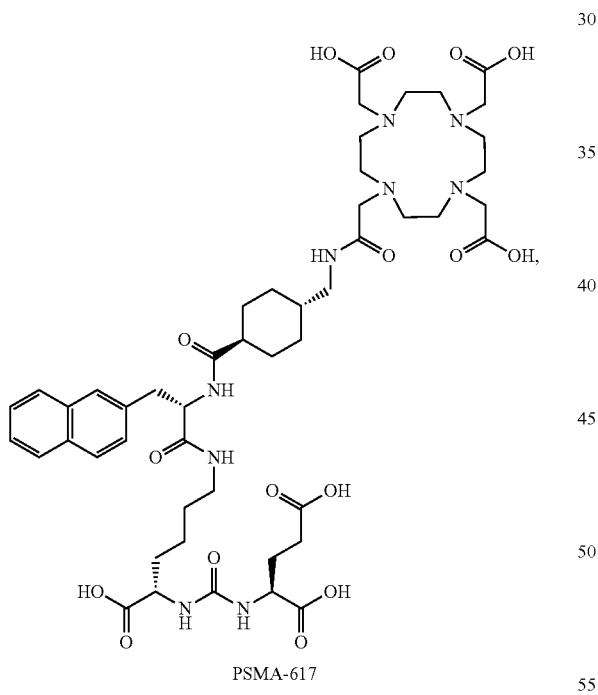

PSMA-617 or a pharmaceutically acceptable salt thereof. In certain embodiments, the radionuclide labelled PSMA binding agent comprises $^{68}$Ga-PSMA-617, which is PSMA-617 labelled with $^{68}$Ga, or a pharmaceutically acceptable salt thereof. In certain embodiments, the radionuclide labelled PSMA binding agent comprises $^{177}$Lu-PSMA-617, which is PSMA-617 labelled with $^{177}$Lu, or a pharmaceutically acceptable salt thereof.

In certain embodiments, the radionuclide labelled PSMA binding agent comprises PSMA-I&T:

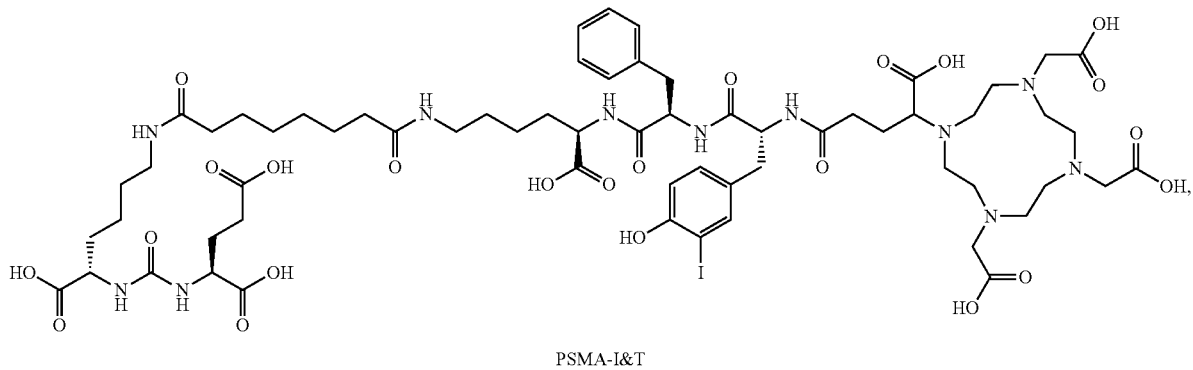 [SMILES: O=C(O)CC[C@H](NC(=O)N[C@@H](CCCCNC(=O)CCCCCCC(=O)NCCCC[C@@H](NC(=O)[C@@H](Cc1ccccc1)NC(=O)[C@@H](Cc1ccc(O)c(I)c1)NC(=O)CCC(C(=O)O)N1CCN(CC(=O)O)CCN(CC(=O)O)CCN(CC(=O)O)CC1)C(=O)O)C(=O)O)C(=O)O]

PSMA-I&T or a pharmaceutically acceptable salt thereof. In certain embodiments, the radionuclide labelled PSMA binding agent comprises $^{68}$Ga-PSMA-I&T, which is PSMA-I&T labelled with $^{68}$Ga, or a pharmaceutically acceptable salt thereof.

In certain embodiments, the radionuclide labelled PSMA binding agent comprises PSMA-1007:

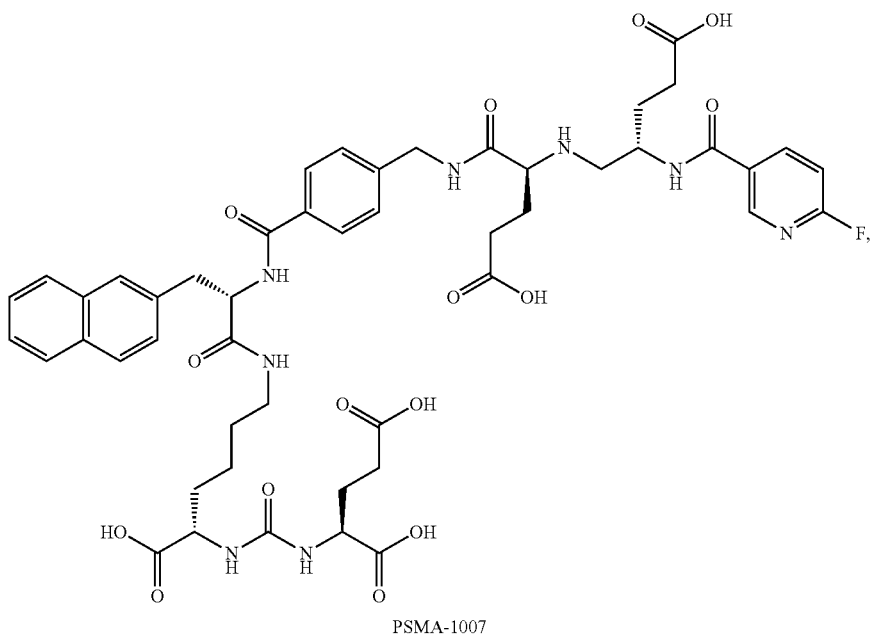

PSMA-1007 or a pharmaceutically acceptable salt thereof. In certain embodiments, the radionuclide labelled PSMA binding agent comprises $^{18}$F-PSMA-1007, which is PSMA-1007 labelled with $^{18}$F, or a pharmaceutically acceptable salt thereof.

ii. SPECT Imaging Radionuclide Labelled PSMA Binding Agents

In certain embodiments, the radionuclide labelled PSMA binding agent is a radionuclide labelled PSMA binding agent appropriate for SPECT imaging.

In certain embodiments, the radionuclide labelled PSMA binding agent comprises 1404 (also referred to as MIP-1404):

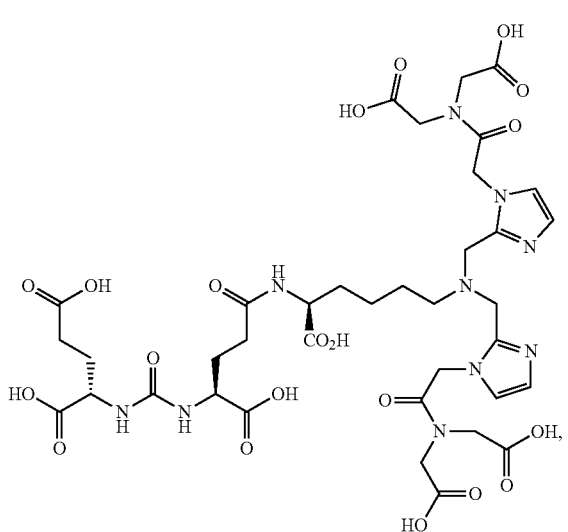

or a pharmaceutically acceptable salt thereof.

In certain embodiments, the radionuclide labelled PSMA binding agent comprises 1405 (also referred to as MIP-1405):

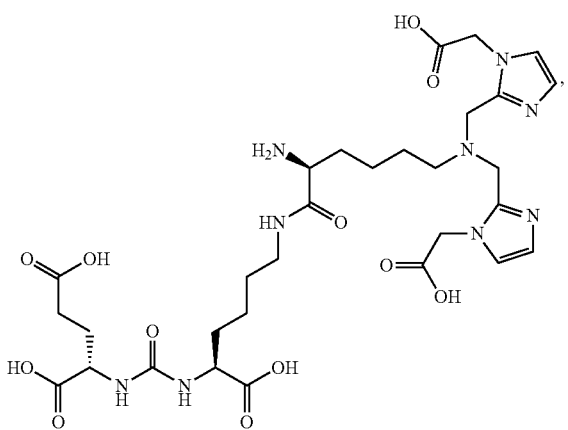

or a pharmaceutically acceptable salt thereof.

In certain embodiments, the radionuclide labelled PSMA binding agent comprises 1427 (also referred to as MIP-1427):

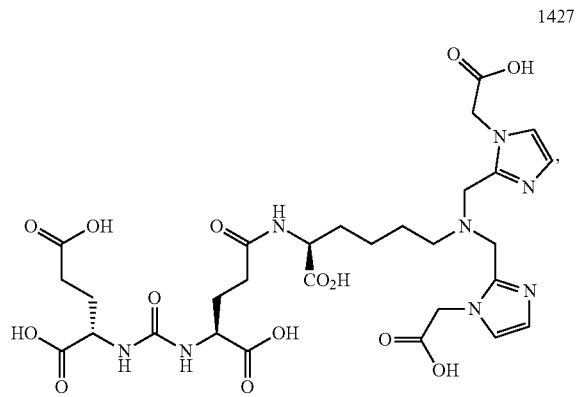 [SMILES: O=C(O)CC[C@H](NC(=O)N[C@@H](CCC(=O)N[C@@H](CCCCN(Cc1nccn1CC(=O)O)Cc1nccn1CC(=O)O)C(=O)O)C(=O)O)C(=O)O]

or a pharmaceutically acceptable salt thereof.

In certain embodiments, the radionuclide labelled PSMA binding agent comprises 1428 (also referred to as MIP-1428):

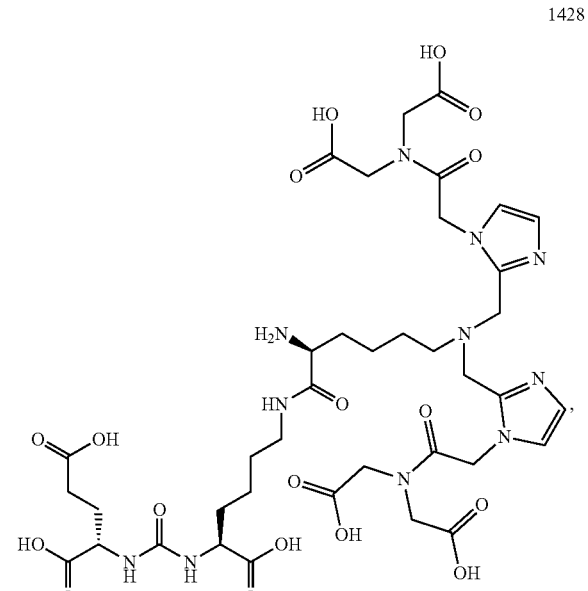

or a pharmaceutically acceptable salt thereof.

In certain embodiments, the PSMA binding agent is labelled with a radionuclide by chelating it to a radioisotope of a metal [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)].

In certain embodiments, 1404 is labelled with a radionuclide (e.g., chelated to a radioisotope of a metal). In certain embodiments, the radionuclide labelled PSMA binding agent comprises $^{99m}$Tc-MIP-1404, which is 1404 labelled with (e.g., chelated to) $^{99m}$Tc:

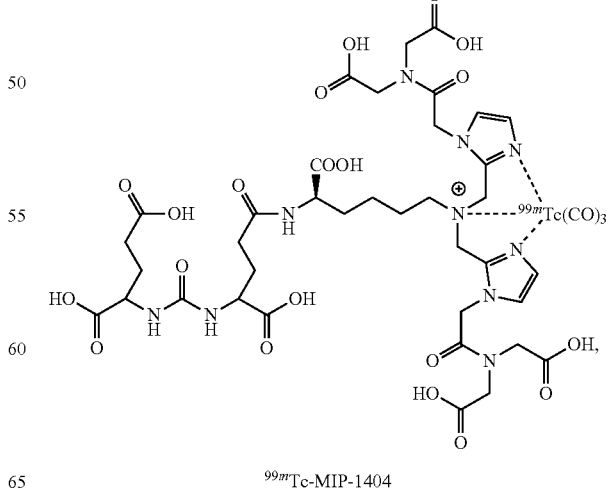

or a pharmaceutically acceptable salt thereof. In certain embodiments, 1404 may be chelated to other metal radioisotopes [e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] to form a compound having a structure similar to the structure shown above for $^{99m}$Tc-MIP-1404, with the other metal radioisotope substituted for $^{99m}$Tc.

In certain embodiments, 1405 is labelled with a radionuclide (e.g., chelated to a radioisotope of a metal). In certain embodiments, the radionuclide labelled PSMA binding agent comprises $^{99m}$Tc-MIP-1405, which is 1405 labelled with (e.g., chelated to)$^{99m}$Tc:

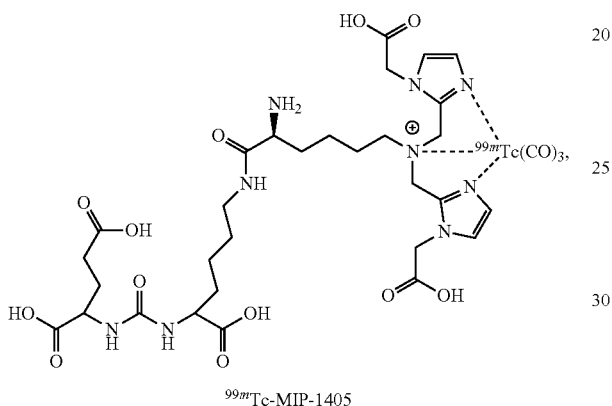

$^{99m}$Tc-MIP-1405 or a pharmaceutically acceptable salt thereof. In certain embodiments, 1405 may be chelated to other metal radioisotopes [e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] to form a compound having a structure similar to the structure shown above for $^{99m}$Tc-MIP-1405, with the other metal radioisotope substituted for $^{99m}$Tc.

In certain embodiments, 1427 is labelled with (e.g., chelated to) a radioisotope of a metal, to form a compound according to the formula below:

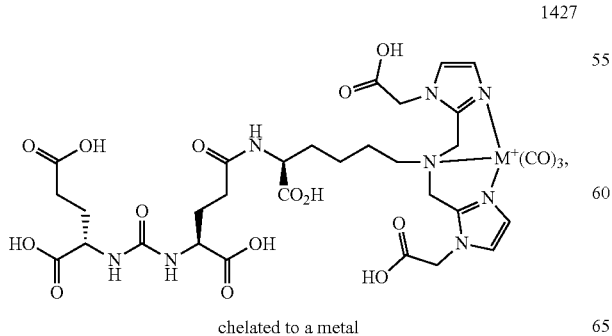

1427 chelated to a metal or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] with which 1427 is labelled.

In certain embodiments, 1428 is labelled with (e.g., chelated to) a radioisotope of a metal, to form a compound according to the formula below:

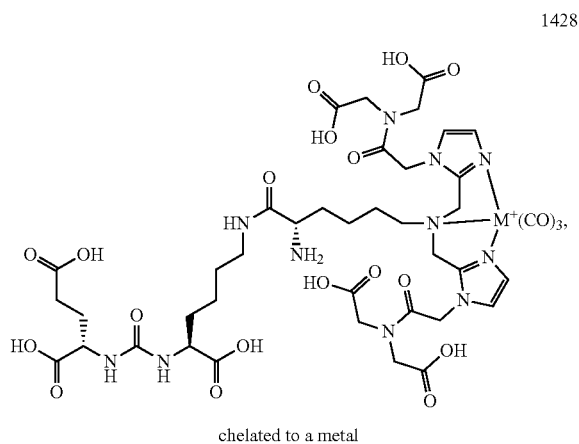

1428 chelated to a metal or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., $^{177}$Lu); e.g., a radioisotope of gallium (Ga) (e.g., $^{68}$Ga; e.g., $^{67}$Ga); e.g., a radioisotope of indium (e.g., $^{111}$In); e.g., a radioisotope of copper (Cu) (e.g., $^{67}$Cu)] with which 1428 is labelled.

In certain embodiments, the radionuclide labelled PSMA binding agent comprises PSMA I&S:

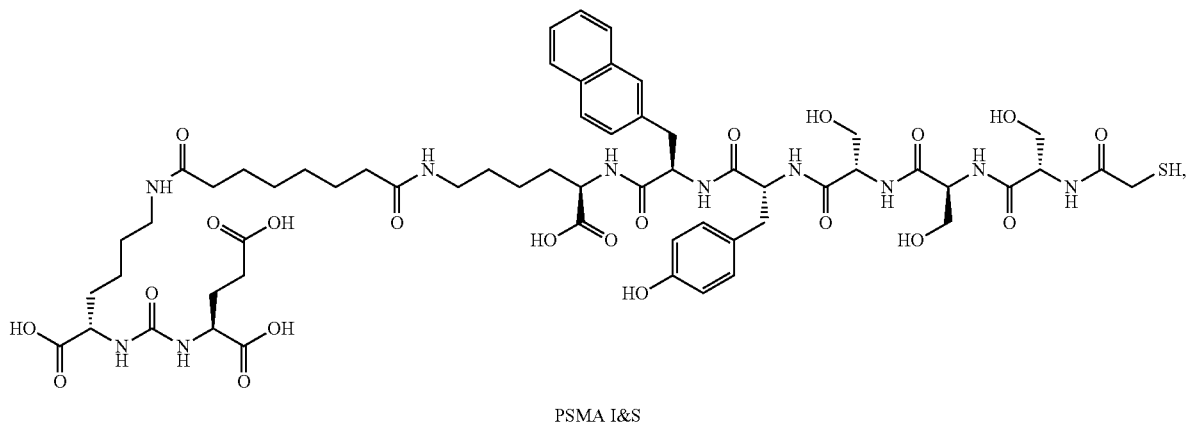 [SMILES: O=C(O)CC[C@H](NC(=O)N[C@@H](CCCCNC(=O)CCCCCCC(=O)NCCCC[C@@H](NC(=O)[C@@H](Cc1ccc2ccccc2c1)NC(=O)[C@@H](Cc1ccc(O)cc1)NC(=O)[C@H](CO)NC(=O)[C@H](CO)NC(=O)[C@H](CO)NC(=O)CS)C(=O)O)C(=O)O)C(=O)O]

PSMA I&S or a pharmaceutically acceptable salt thereof. In certain embodiments, the radionuclide labelled PSMA binding agent comprises $^{99m}$Tc-PSMA I&S, which is PSMA I&S labelled with $^{99m}$Tc, or a pharmaceutically acceptable salt thereof.

D. Computer System and Network Architecture

Figure 7:
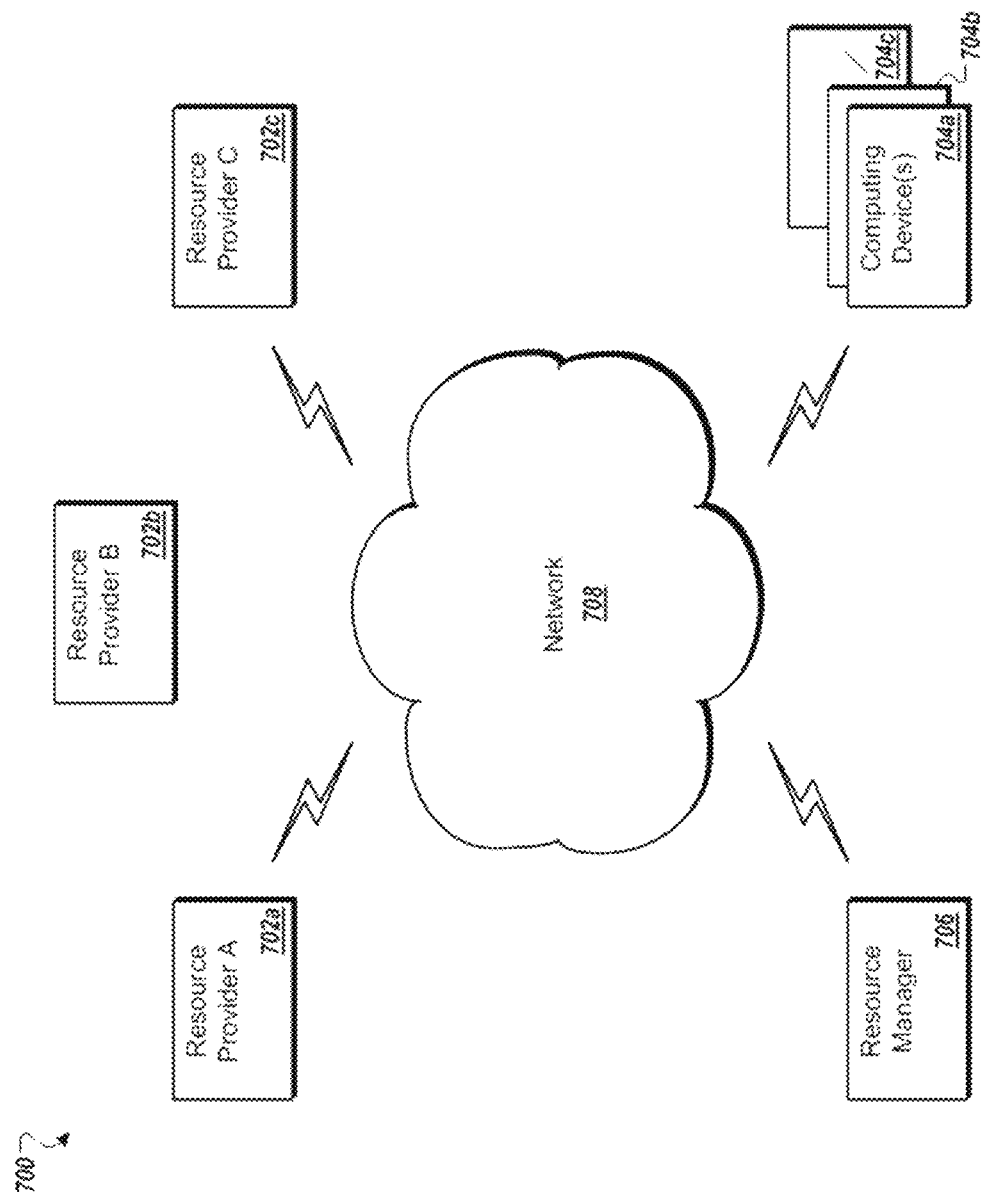
FIG. 7 is a block diagram of an exemplary cloud computing environment, used in certain embodiments.

As shown in FIG. 7, an implementation of a network environment 700 for use in providing systems, methods, and architectures described herein is shown and described. In brief overview, referring now to FIG. 7, a block diagram of an exemplary cloud computing environment 700 is shown and described. The cloud computing environment 700 may include one or more resource providers 702a, 702b, 702c (collectively, 702). Each resource provider 702 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 702 may be connected to any other resource provider 702 in the cloud computing environment 700. In some implementations, the resource providers 702 may be connected over a computer network 708. Each resource provider 702 may be connected to one or more computing device 704a, 704b, 704c (collectively, 704), over the computer network 708.

The cloud computing environment 700 may include a resource manager 706. The resource manager 706 may be connected to the resource providers 702 and the computing devices 704 over the computer network 708. In some implementations, the resource manager 706 may facilitate the provision of computing resources by one or more resource providers 702 to one or more computing devices 704. The resource manager 706 may receive a request for a computing resource from a particular computing device 704. The resource manager 706 may identify one or more resource providers 702 capable of providing the computing resource requested by the computing device 704. The resource manager 706 may select a resource provider 702 to provide the computing resource. The resource manager 706 may facilitate a connection between the resource provider 702 and a particular computing device 704. In some implementations, the resource manager 706 may establish a connection between a particular resource provider 702 and a particular computing device 704. In some implementations, the resource manager 706 may redirect a particular computing device 704 to a particular resource provider 702 with the requested computing resource.

Figure 8:
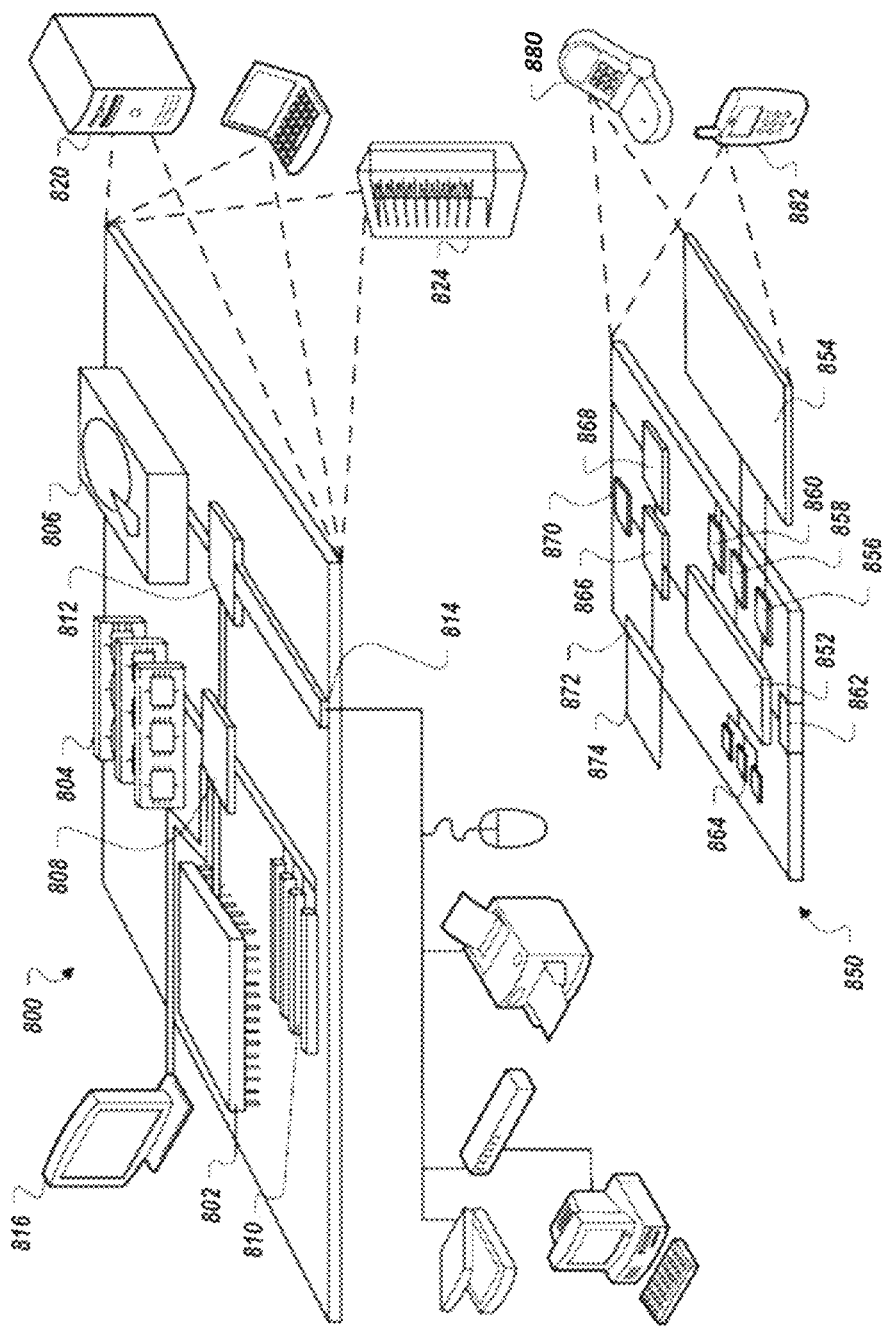
FIG. 8 is a block diagram of an example computing device and an example mobile computing device used in certain embodiments The features and advantages of the present disclosure will become more apparent from the detailed description set forth below when taken in conjunction with the drawings, in which like reference characters identify corresponding ele-

FIG. 8 shows an example of a computing device 800 and a mobile computing device 850 that can be used to implement the techniques described in this disclosure. The computing device 800 is intended to represent various forms of digital computers, such as laptops, desktops, workstations, personal digital assistants, servers, blade servers, mainframes, and other appropriate computers. The mobile computing device 850 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 800 includes a processor 802, a memory 804, a storage device 806, a high-speed interface 808 connecting to the memory 804 and multiple high-speed expansion ports 810, and a low-speed interface 812 connecting to a low-speed expansion port 814 and the storage device 806. Each of the processor 802, the memory 804, the storage device 806, the high-speed interface 808, the high-speed expansion ports 810, and the low-speed interface 812, are interconnected using various busses, and may be mounted on a common motherboard or in other manners as appropriate. The processor 802 can process instructions for execution within the computing device 800, including instructions stored in the memory 804 or on the storage device 806 to display graphical information for a GUI on an external input/output device, such as a display 816 coupled to the high-speed interface 808. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 804 stores information within the computing device 800. In some implementations, the memory 804 is a volatile memory unit or units. In some implementations, the memory 804 is a non-volatile memory unit or units. The memory 804 may also be another form of computer-readable medium, such as a magnetic or optical disk.

The storage device 806 is capable of providing mass storage for the computing device 800. In some implementations, the storage device 806 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 802), perform one or more methods, such as those described above. The instructions can also be stored by one or more storage devices such as computer- or machine-readable mediums (for example, the memory 804, the storage device 806, or memory on the processor 802).

The high-speed interface 808 manages bandwidth-intensive operations for the computing device 800, while the low-speed interface 812 manages lower bandwidth-intensive operations. Such allocation of functions is an example only. In some implementations, the high-speed interface 808 is coupled to the memory 804, the display 816 (e.g., through a graphics processor or accelerator), and to the high-speed expansion ports 810, which may accept various expansion cards (not shown). In the implementation, the low-speed interface 812 is coupled to the storage device 806 and the low-speed expansion port 814. The low-speed expansion port 814, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 800 may be implemented in a number of different forms, as shown in the figure. For example, it may be implemented as a standard server 820, or multiple times in a group of such servers. In addition, it may be implemented in a personal computer such as a laptop computer 822. It may also be implemented as part of a rack server system 824. Alternatively, components from the computing device 800 may be combined with other components in a mobile device (not shown), such as a mobile computing device 850. Each of such devices may contain one or more of the computing device 800 and the mobile computing device 850, and an entire system may be made up of multiple computing devices communicating with each other.

The mobile computing device 850 includes a processor 852, a memory 864, an input/output device such as a display 854, a communication interface 866, and a transceiver 868, among other components. The mobile computing device 850 may also be provided with a storage device, such as a micro-drive or other device, to provide additional storage. Each of the processor 852, the memory 864, the display 854, the communication interface 866, and the transceiver 868, are interconnected using various buses, and several of the components may be mounted on a common motherboard or in other manners as appropriate.

The processor 852 can execute instructions within the mobile computing device 850, including instructions stored in the memory 864. The processor 852 may be implemented as a chipset of chips that include separate and multiple analog and digital processors. The processor 852 may provide, for example, for coordination of the other components of the mobile computing device 850, such as control of user interfaces, applications run by the mobile computing device 850, and wireless communication by the mobile computing device 850.

The processor 852 may communicate with a user through a control interface 858 and a display interface 856 coupled to the display 854. The display 854 may be, for example, a TFT (Thin-Film-Transistor Liquid Crystal Display) display or an OLED (Organic Light Emitting Diode) display, or other appropriate display technology. The display interface 856 may comprise appropriate circuitry for driving the display 854 to present graphical and other information to a user. The control interface 858 may receive commands from a user and convert them for submission to the processor 852. In addition, an external interface 862 may provide communication with the processor 852, so as to enable near area communication of the mobile computing device 850 with other devices. The external interface 862 may provide, for example, for wired communication in some implementations, or for wireless communication in other implementations, and multiple interfaces may also be used.

The memory 864 stores information within the mobile computing device 850. The memory 864 can be implemented as one or more of a computer-readable medium or media, a volatile memory unit or units, or a non-volatile memory unit or units. An expansion memory 874 may also be provided and connected to the mobile computing device 850 through an expansion interface 872, which may include, for example, a SIMM (Single In Line Memory Module) card interface. The expansion memory 874 may provide extra storage space for the mobile computing device 850, or may also store applications or other information for the mobile computing device 850. Specifically, the expansion memory 874 may include instructions to carry out or supplement the processes described above, and may include secure information also. Thus, for example, the expansion memory 874 may be provide as a security module for the mobile computing device 850, and may be programmed with instructions that permit secure use of the mobile computing device 850. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 852), perform one or more methods, such as those described above. The instructions can also be stored by one or more storage devices, such as one or more computer- or machine-readable mediums (for example, the memory 864, the expansion memory 874, or memory on the processor 852). In some implementations, the instructions can be received in a propagated signal, for example, over the transceiver 868 or the external interface 862.

The mobile computing device 850 may communicate wirelessly through the communication interface 866, which may include digital signal processing circuitry where necessary. The communication interface 866 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 868 using a radio-frequency. In addition, short-range communication may occur, such as using a Bluetooth®, Wi-Fi™, or other such transceiver (not shown). In addition, a GPS (Global Positioning System) receiver module 870 may provide additional navigation- and location-related wireless data to the mobile computing device 850, which may be used as appropriate by applications running on the mobile computing device 850.

The mobile computing device 850 may also communicate audibly using an audio codec 860, which may receive spoken information from a user and convert it to usable digital information. The audio codec 860 may likewise generate audible sound for a user, such as through a speaker, e.g., in a handset of the mobile computing device 850. Such sound may include sound from voice telephone calls, may include recorded sound (e.g., voice messages, music files, etc.) and may also include sound generated by applications operating on the mobile computing device 850.

The mobile computing device 850 may be implemented in a number of different forms, as shown in the figure. For example, it may be implemented as a cellular telephone 880. It may also be implemented as part of a smart-phone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the various modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for automatically processing 3D images of a subject to identify and/or characterize cancerous lesions within the subject, the method comprising:
   (a) receiving, by a processor of a computing device, a 3D functional image of the subject obtained using a functional imaging modality;
   (b) automatically detecting, by the processor, using a machine learning module, one or more hotspots within the 3D functional image, each hotspot corresponding to a local region of elevated intensity with respect to its surrounding and representing a potential cancerous lesion within the subject, thereby creating a 3D hotspot map, identifying, for each hotspot, a corresponding 3D hotspot volume within the 3D functional image, wherein the machine learning module receives, as input, at least a portion of the 3D functional image and generates the 3D hotspot map as output; and (c) storing and/or providing, for display and/or further processing, the 3D hotspot map, wherein the 3D functional image comprises a positron emission tomography (PET) or a single-photon emission computed tomography (SPECT) image obtained following administration of an agent to the subject.

2. The method of claim 1, wherein the machine learning module receives, as input, a 3D segmentation map that identifies one or more volumes of interest (VOIs) within the 3D functional image, each VOI corresponding to a particular target tissue region and/or a particular anatomical region within the subject.

3. The method of claim 1,
comprising receiving, by the processor, a 3D anatomical image of the subject obtained using an anatomical imaging modality, wherein the 3D anatomical image comprises a graphical representation of tissue within the subject, and wherein the machine learning module receives at least two channels of input, said input channels comprising a first input channel corresponding to at least a portion of the 3D anatomical image and a second input channel corresponding to the portion of the 3D functional image.

4. The method of claim 3, wherein the machine learning module receives, as input, a 3D segmentation map that identifies, within the 3D functional image and/or the 3D anatomical image, one or more volumes of interest (VOIs), each VOI corresponding to a particular target tissue region and/or a particular anatomical region.

5. The method of claim 4, comprising automatically segmenting, by the processor, the 3D anatomical image, thereby creating the 3D segmentation map.

6. The method of claim 1, wherein the machine learning module is a region-specific machine learning module that receives, as input, a specific portion of the 3D functional image corresponding to one or more specific tissue regions and/or anatomical regions of the subject.

7. The method of claim 1, comprising:
(d) determining, by the processor, for each hotspot of at least a portion of the hotspots, a lesion likelihood classification corresponding to a likelihood of the hotspot representing a lesion within the subject.

8. The method of claim 7, wherein step (d) comprises using the machine learning module to determine, for each hotspot of the portion, the lesion likelihood classification.

9. The method of claim 7, wherein step (d) comprises using a second machine learning module to determine the lesion likelihood classification for each hotspot.

10. The method of claim 9, comprising determining, by the processor, for each hotspot, a set of one or more hotspot features and using the set of the one or more hotspot features as input to the second machine learning module.

11. The method of claim 7, comprising:
(e) selecting, by the processor, based at least in part on the lesion likelihood classifications for the hotspots, a subset of the one or more hotspots corresponding to hotspots having a high likelihood of corresponding to cancerous lesions.

12. The method of claim 1, comprising:
(f) adjusting intensities of voxels of the 3D functional image, by the processor, to correct for intensity bleed from one or more high-intensity volumes of the 3D functional image, each of the one or more high-intensity volumes corresponding to a high-uptake tissue region within the subject associated with high radiopharmaceutical uptake under normal circumstances.

13. The method of claim 12, wherein step (f) comprises correcting for intensity bleed from a plurality of high-intensity volumes one at a time, in a sequential fashion.

14. The method of claim 12, wherein the one or more high-intensity volumes correspond to one or more high-uptake tissue regions selected from the group consisting of a kidney, a liver, and a bladder.

15. The method of claim 1, comprising:
(g) determining, by the processor, for each of at least a portion of the one or more hotspots, a corresponding lesion index indicative of a level of radiopharmaceutical uptake within and/or size of an underlying lesion to which the hotspot corresponds.

16. The method of claim 15, wherein step (g) comprises comparing an intensity intensities) of one or more voxels associated with the hotspot with one or more reference values, each reference value associated with a particular reference tissue region of a reference volume corresponding to the reference tissue region.

17. The method of claim 16, wherein the one or more reference values comprise one or more members selected from the group consisting of an aorta reference value associated with an aorta portion of the subject and a liver reference value associated with a liver of the subject.

18. The method of claim 15, comprising using the determined lesion index values compute an overall risk index for the subject, indicative of a cancer status and/or risk for the subject.

19. The method of claim 1, comprising determining, by the processor, for each hotspot, an anatomical classification corresponding to a particular anatomical region and/or group of anatomical regions within the subject in which the potential cancerous lesion that the hotspot represents is determined to be located.

20. The method of claim 1, comprising:
(h) causing, by the processor, for display within a graphical user interface (GUI), rendering of a graphical representation of at least a portion of the one or more hotspots for review by a user.

21. The method of claim 20, comprising:
(i) receiving, by the processor, via the GUI, a user selection of a subset of the one or more hotspots confirmed via user review as likely to represent underlying cancerous lesions within the subject.

22. The method of claim 1, wherein the agent comprises a PSMA binding agent.

23. The method of claim 22, wherein the agent comprises [18F]DCFPyL.

24. The method of claim 1, wherein the machine learning module implements a neural network.

25. The method of claim 1, wherein the processor is a processor of a cloud-based system.

26. The method of claim 1, wherein the machine learning module comprises a convolutional neural network (CNN).

27. A method for automatically processing 3D images of a subject to identify and/or characterize cancerous lesions within the subject, the method comprising:

(a) receiving, by a processor of a computing device, a 3D functional image of the subject obtained using a functional imaging modality;

(b) receiving, by the processor, a 3D anatomical image of the subject obtained using an anatomical imaging modality, wherein the 3D anatomical image comprises a graphical representation of tissue within the subject;

(c) automatically detecting, by the processor, using a machine learning module, one or more hotspots within the 3D functional image, each hotspot corresponding to a local region of elevated intensity with respect to its surrounding and representing a potential cancerous lesion within the subject, thereby creating a 3D hotspot map, identifying, for each hotspot, a corresponding 3D hotspot volume within the 3D functional image, wherein the machine learning module receives at least two channels of input, said input channels comprising a first input channel corresponding to at least a portion of the 3D functional image and a second input channel corresponding to at least a portion of the 3D anatomical image and/or anatomical information derived therefrom, and generates the 3D hotspot map as output; and (d) storing and/or providing, for display and/or further processing, the 3D hotspot map, wherein the 3D functional image comprises a positron emission tomography (PET) or a single-photon emission computed tomography (SPECT) image obtained following administration of an agent to the subject.

28. The method of claim 27, wherein the machine learning module comprises a convolutional neural network (CNN).

29. A system for automatically processing 3D images of a subject to identify and/or characterize cancerous lesions within the subject, the system comprising:

a processor of a computing device; and a memory having instructions stored thereon, wherein the instructions, when executed by the processor, cause the processor to:

(a) receive a 3D functional image of the subject obtained using a functional imaging modality;

(b) automatically detect, using a machine learning module, one or more hotspots within the 3D functional image, each hotspot corresponding to a local region of elevated intensity with respect to its surrounding and representing a potential cancerous lesion within the subject, thereby creating a 3D hotspot map, identifying, for each hotspot, a corresponding 3D hotspot volume within the 3D functional image, wherein the machine learning module receives, as input, at least a portion of the 3D functional image and generates the 3D hotspot map as output; and (c) store and/or provide, for display and/or further processing, the 3D hotspot map, wherein the 3D functional image comprises a positron emission tomography (PET) or single-photon emission computed tomography (SPECT) image obtained following administration of an agent to the subject.

30. The system of claim 29, wherein the machine learning module comprises a convolutional neural network (CNN).

31. A system for automatically processing 3D images of a subject to identify and/or characterize cancerous lesions within the subject, the system comprising:

a processor of a computing device; and a memory having instructions stored thereon, wherein the instructions, when executed by the processor, cause the processor to:

(a) receive a 3D functional image of the subject obtained using a functional imaging modality;

(b) receive a 3D anatomical image of the subject obtained using an anatomical imaging modality, wherein the 3D anatomical image comprises a graphical representation of tissue within the subject;

(c) automatically detect, using a machine learning module, one or more hotspots within the 3D functional image, each hotspot corresponding to a local region of elevated intensity with respect to its surrounding and representing a potential cancerous lesion within the subject, thereby creating a 3D hotspot map, identifying, for each hotspot, a corresponding 3D hotspot volume within the 3D functional image, wherein the machine learning module receives at least two channels of input, said input channels comprising a first input channel corresponding to at least a portion of the 3D functional image and a second input channel corresponding to at least a portion of the 3D anatomical image and/or anatomical information derived therefrom, and generates the 3D hotspot map as output; and (d) store and/or provide, for display and/or further processing, the 3D hotspot map, wherein the 3D functional image comprises a positron emission tomography (PET) or single-photon emission computed tomography (SPECT) image obtained following administration of an agent to the subject.

32. The system of claim 31, wherein the machine learning module comprises a convolutional neural network (CNN).

* * * * *